US010768157B2

(12) United States Patent
Kabir et al.

(10) Patent No.: US 10,768,157 B2
(45) Date of Patent: *Sep. 8, 2020

(54) MATERIALS AND METHODS FOR THE DETECTION OF TRACE AMOUNTS OF SUBSTANCES IN BIOLOGICAL AND ENVIRONMENTAL SAMPLES

(71) Applicants: Abuzar Kabir, Miami, FL (US); Kenneth G. Furton, Homestead, FL (US)

(72) Inventors: Abuzar Kabir, Miami, FL (US); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 105 days.

This patent is subject to a terminal disclaimer.

(21) Appl. No.: 15/714,349

(22) Filed: Sep. 25, 2017

(65) Prior Publication Data

US 2018/0059082 A1 Mar. 1, 2018

Related U.S. Application Data

(63) Continuation-in-part of application No. 15/298,776, filed on Oct. 20, 2016, now Pat. No. 9,772,338.

(60) Provisional application No. 62/243,977, filed on Oct. 20, 2015.

(51) Int. Cl.
| | |
|---|---|
| *G01N 33/04* | (2006.01) |
| *B01J 20/26* | (2006.01) |
| *G01N 33/94* | (2006.01) |
| *C08G 77/06* | (2006.01) |
| *C08G 77/26* | (2006.01) |
| *C08J 9/26* | (2006.01) |
| *B01J 20/30* | (2006.01) |
| *B01J 20/291* | (2006.01) |
| *B01J 20/28* | (2006.01) |
| *C08G 77/00* | (2006.01) |

(52) U.S. Cl.
CPC ............ *G01N 33/04* (2013.01); *B01J 20/268* (2013.01); *B01J 20/28047* (2013.01); *B01J 20/291* (2013.01); *B01J 20/3085* (2013.01); *C08G 77/06* (2013.01); *C08G 77/26* (2013.01); *C08G 77/80* (2013.01); *C08J 9/26* (2013.01); *G01N 33/94* (2013.01); *G01N 33/9446* (2013.01); *B01J 2220/54* (2013.01); *C08J 2201/0462* (2013.01); *C08J 2205/02* (2013.01); *C08J 2383/08* (2013.01); *G01N 2600/00* (2013.01)

(58) Field of Classification Search
CPC .............. G01N 33/9446; G01N 33/04; G01N 2600/00; C08G 77/06; B01J 20/268
See application file for complete search history.

(56) References Cited

U.S. PATENT DOCUMENTS

2012/0070879 A1 3/2012 Sallitt

FOREIGN PATENT DOCUMENTS

| WO | 2014062632 A1 | 4/2014 | |
|---|---|---|---|
| WO | 2014102209 A1 | 7/2014 | |
| WO | WO-2014102209 A1 * | 7/2014 | ............ C08G 77/26 |

OTHER PUBLICATIONS

Lee, Sung-Chuan et al. "Studies on the preparation and properties of sol-gel molecularly imprinte polymer based on tetramethoxysilane and methyltrimethoxysilane for recognized sulfonamides." Polymer Journal (2009) 41 1092-1097. (Year: 2009).*
Alizadeh, T. et al., "Selective determination of chloramphenicol at trace level in milk samples by the electrode modified with molecularly imprinted polymer." Food Chemistry, Feb. 15, 2012, 130(4): Abstract.
Boyd, B. et al., "Development of an improved method for trace analysis of chloramphenicol using molecularly imprinted polymers." Journal of Chromatography A., Dec. 7, 2007, 1174(1-2): 63-71.
Buszewski, B., Szultka, M., "Past, Present, and Future of Solid Phase Extraction: A Review." Critical Reviews in Analytical Chemistry, Jun. 13, 2012, 42(3): Abstract.
Chen, L. et al., "Magnetic molecularly imprinted polymer extraction of chloramphenicol from honey." Analytical Methods, Nov. 2013, 141(1): 23-28.
Chen, L. et al., "Recent advances in molecular imprinting technology: current status, challenges and highlighted applications." Chem. Soc. Rev., 2011, 40: 2922-2942.
Cheong, W. J. et al., "Molecular imprinted polymers for separation science: A review of reviews." J. Sep. Sci., Feb. 2013, 36: 609-628.
Commission, "Commission Decision of Mar. 13, 2003 amending Decision 2002/657/EC as regards the setting of minimum required performance limits (MRPLs) for certain residues in food of animal origin." Official Journal of the European Union, 2003, 17-18.

(Continued)

*Primary Examiner* — Christopher Adam Hixson
(74) *Attorney, Agent, or Firm* — Saliwanchik, Lloyd & Eisenschenk

(57) ABSTRACT

The subject invention provides chemical compositions and synthesis strategies to create molecularly imprinted polymers (MIPs) via sol-gel processes. In a specific embodiment, the subject invention utilizes a(n) organic, inorganic, or metallic template analyte to create a hybrid organic-inorganic or inorganic three-dimensional network possessing cavities complementary to the shape, size, and functional orientation of the template molecule or ions. The subject invention further pertains to the use of the novel MIPs as selective solid phase extraction (SPE) sorbents for pre-concentration and clean-up of trace substances in biological and environmental samples. Synthesis of other molecularly imprinted polymers with environmental, pharmaceutical, chemical, clinical, toxicological, and national security implications can be conducted in accordance with the teachings of the subject invention.

20 Claims, 17 Drawing Sheets

(56) References Cited

OTHER PUBLICATIONS

Falagas, M. E. et al., "Potential of old-generation antibiotics to address current need for new antibiotics." Expert Rev. Anti Infect. Ther., 2008, 6(5): 593-600.

Farré, M. et al., "Green analytical chemistry in the determination of organic pollutants in the aquatic environment." Trends in Analytical Chemistry, 2010, 29(11): 1347-1362.

Hu, J. et al., "Surface molecularly imprinted polymers with synthetic dummy template for simultaneously selective recognition of nine phthalate esters." Journal of Chromatography A., Feb. 21, 2014, 1330: 6-13.

Karageorgou, E. et al., "Development and validation according to European Union Decision 2002/657/EC of an HPLC-DAD method for milk multi-residue analysis of penicillins and amphenicols based on dispersive extraction by QuEChERS in MSPD format" J Sep Sci., Aug. 2011, 34(15): Abstract.

Karageorgou, E. et al., "Multiresidue LC-MS/MS analysis of cephalosporins and quinolones in milk following ultrasound-assisted matrix solid-phase dispersive extraction combined with the quick, easy, cheap, effective, rugged, and safe methodology." J. Sep. Sci., Jun. 2013, 36(12): Abstract.

Karageorgou, E. et al., "Ultrasound-assisted dispersive extraction for the high pressure liquid chromatographic determination of tetracyclines residues in milk with diode array detection." Analytical Methods, May 2014, 150: 328-334.

Karageorgou, E. et al., "Ultrasound-assisted matrix solid phase dispersive extraction for the simultaneous analysis of β-lactams (four penicillins and eight cephalosporins) in milk by high performance liquid chromatography with photodiode array detection." J. Sep. Sci., Oct. 2012, 35(19): Abstract.

Li, Junjie et al., "Molecularly imprinted polymers on the surface of silica microspheres via sol-gel method for the selective extraction of streptomycin in aqueous samples." J. Sep. Sci., Mar. 2013, 36(6): 1142-1148.

Liu et al., "Synthesis and characterization of molecularly imprinted polymers for recognition of ciprofloxacin," Front. Chem. China, 2008, 3(4): 378-383.

Liu, G. et al., "Towards the development of a sensitive electrochemical sensor for the determination of chloramphenicol residues in milk." Analytical Methods, 2015, 7(4): Abstract.

Mohamed, R. et al., "Advantages of molecularly imprinted polymers LC-ESI-MS/MS for the selective extraction and quantification of chloramphenicol in milk-based matrixes. Comparison with a classical sample preparation." Anal. Chem., Dec. 15, 2007, 79(24): Abstract.

Nicolich, R. S. et al., "Food safety evaluation: Detection and confirmation of chloramphenicol in milk by high performance liquid chromatography-tandem mass spectrometry." Analytica Chimica Acta, Apr. 13, 2006, 565(1): Abstract.

Ramos, M. et al., "Chloramphenicol Residues in Food Samples: Their Analysis and Stability During Storage." Journal of Chromatography A., 2003, 26(15): Abstract.

Rejtharová, M., Rejthar, L., "Determination of chloramphenicol in urine, feed water, milk and honey samples using molecular imprinted polymer clean-up." Journal of Chromatography A., Nov. 13, 2009, 1216(46): Abstract.

Rezende, D. R. et al., "Simultaneous determination of chloramphenicol and florfenicol in liquid milk, milk powder and bovine muscle by LC-MS/MS." Food Addit Contam Part A Chem Anal Control Expo Risk Assess., 2012, 29(4): Abstract.

Samanidou, V. et al., "Fast extraction of amphenicols residues from raw milk using novel fabric phase sorptive extraction followed by high-performance liquid chromatography-diode array detection." Analytica Chimica Acta, Jan. 2015, 855: 41-50.

Schirmer, C. et al., "Synthesis of a molecularly imprinted polymer for the selective solid-phase extraction of chloramphenicol from honey." Journal of Chromatography A., Nov. 3, 2006, 1132(1-2): Abstract.

Shi, X. et al., "Molecularly imprinted polymer microspheres for solid-phase extraction of chloramphenicol residues in foods." J Chromatogr B Analyt Technol Biomed Life Sci., May 1, 2007, 850(1-2): Abstract.

Shimelis, O. et al., "Detection of Low Level of Chloramphenicol in Milk and Honey with MIP SPE and LC-MS-MS." Supelco Presentation, 2007.

Tolika, E P. et al., "Development and validation of an HPLC method for the determination of ten sulfonamide residues in milk according to 2002/657/EC." J Sep Sci., Jul. 2011, 34(14): Abstract.

Turton, J. A. et al., "Studies on the haemotoxicity of chloramphenicol succinate in the Dunkin Hartley guinea pig." Int. J. Exp. Path., 2002, 83: 225-238.

Yin, Y. M. et al., "Dummy molecularly imprinted polymers on silica particles for selective solid-phase extraction of tetrabromobisphenol A from water samples." Journal of Chromatography A, Jan. 13, 2012, 1220: Abstract.

\* cited by examiner

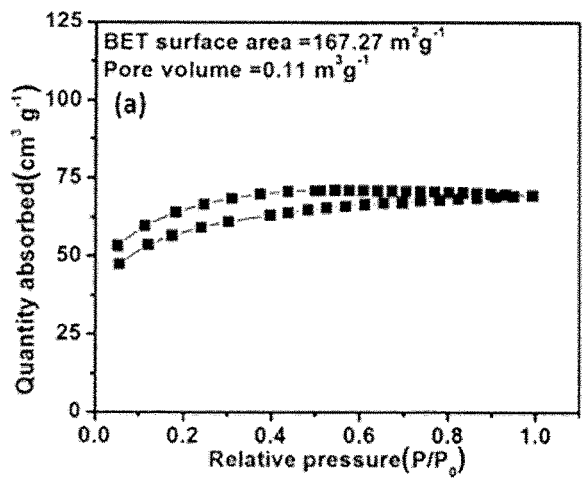 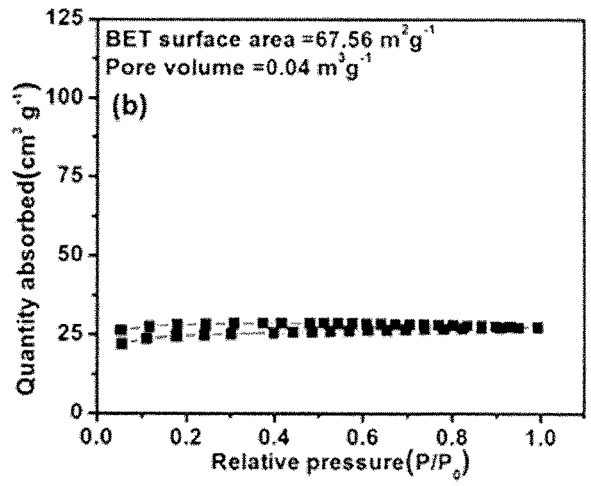
FIG. 4A  FIG. 4B
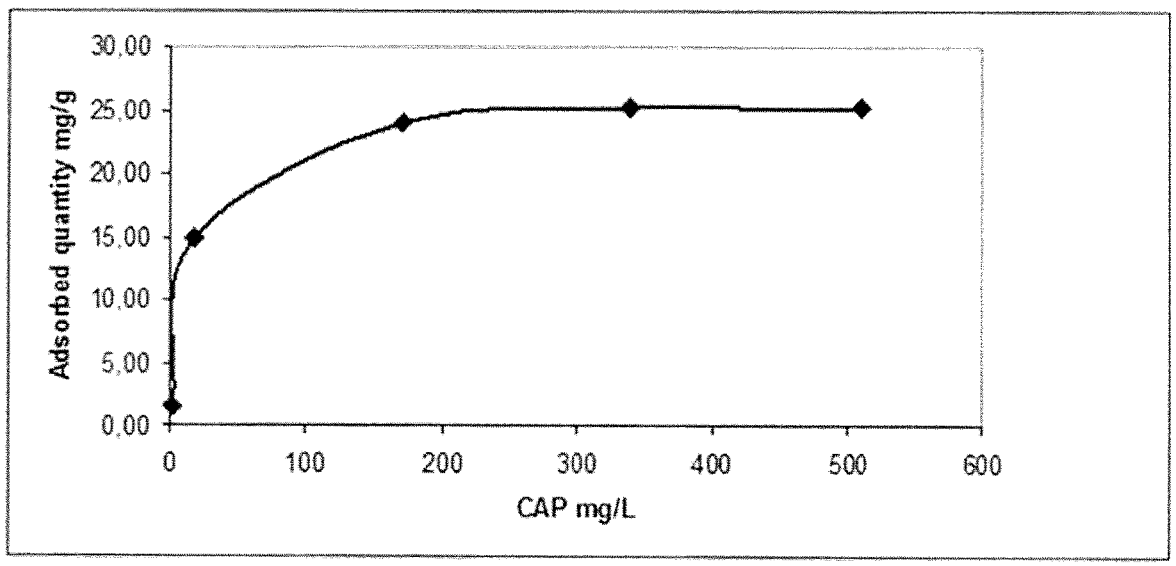
FIG. 5

MATERIALS AND METHODS FOR THE DETECTION OF TRACE AMOUNTS OF SUBSTANCES IN BIOLOGICAL AND ENVIRONMENTAL SAMPLES

CROSS-REFERENCE TO A RELATED APPLICATION

This application is a continuation-in-part application of U.S. Ser. No. 15/298,776, filed Oct. 20, 2016; which claims the benefit of U.S. provisional application Ser. No. 62/243,977, filed Oct. 20, 2015, both of which are incorporated herein by reference in their entirety.

BACKGROUND OF INVENTION

It is often necessary, for health and safety reasons, to detect small amounts of substances in biological and environmental samples. The detection of such substances would ideally be done with good sensitivity and specificity, easily, and at low cost. Such detection is often difficult, however, due to a variety of reasons, including the complexity of the samples that are being tested.

In the early twentieth century, the discovery of the antibiotics was indeed revolutionary for the public health and safety. The benefits of their use in human beings were obvious soon after their discovery that subsequently propelled the administration of antibiotics in livestock during 1950s. The most widespread veterinary antibiotic drugs include tetracyclines, β-lactams and sulfonamides. These well-known drugs are administered to livestock as therapy, disease prolepsis and growth promotion. The prevalent use of these antibiotic drugs in livestock leads to their presence as residues at trace and ultra-trace level concentrations in dairy products and in milk.

Milk is a liquid consisting of water, lactose, protein, fat, minerals, and vitamins. Due to the high nutritional benefit, it is one of the most consumed foods. The presence of antibiotic drug residues in milk samples could put the consumer's health in danger. As such, their presence in milk and related food products has to be avoided and controlled. Consequently, the detection of antibiotic drug residues in milk and milk-based products is of utmost necessity in order to safeguard human health and safety.

The sulfonamide drugs or sulfa drugs are a common category of antibacterial drugs. The sulfachrysoidine (with the trade name Prontosil), was first reported by Domagk, because of its use against murine streptococcal infections. Sulfachrysoidine exerted its antibacterial activity through the release in vivo of para-aminobenzenesulfonamide (sulfanilamide). This represents the first antibacterial agent used in the United States in July 1935 in an unsuccessful attempt to protect a girl from meningitis. The sulfonamide drugs are derivatives of sulfanilamide, which is similar in structure to para-aminobenzoic acid (PABA), a factor required by bacteria for folic acid synthesis. Nowadays, only 40 of the 10,000 sulfanilamide derivatives that have been synthesized are used in medical and veterinary practice. Sulfonamides as antibacterial agents are useful for the treatment of urinary tract infections and infections caused by *Nocardia* species, a typical mycobacteria, and *Toxoplasma gondii*. There are numerous sulfonamides with the same basic structure. The sulfonamides, however, differ from each other primarily by virtue of the different substituents in its R' position.

Chloramphenicol (CAP) is an antibiotic used for the treatment of bacterial infections, and it is often administered to animals for disease prevention. CAP is a protein synthesis inhibitor that acts primarily by binding reversibly to the 50S ribosomal subunit and also can inhibit mitochondrial protein synthesis in mammalian cells. Therefore, despite its role in disease prevention and nonproliferation of bacterial growth, CAP is also associated with potentially serious toxic effects in humans, including bone marrow depression.

Moreover, antibiotic residues in animal milk may cause allergic reactions or lead to antimicrobial resistance. The use of CAP in food animals is, therefore, illegal in most countries, including the USA, Canada, China, and members of the European Union. However, the illicit use of CAP in cows to control mastitis and other animal diseases continues because of its low cost and easy availability (G. Y. Liu, C. Y. Chai, Towards the development of a sensitive electrochemical sensor for the determination of chloramphenicol residues in milk, Analytical Methods, 7 (2015) 1572-1577).

Analysis of ultra-trace level of contaminants, including CAP, in complex biological sample matrices is a daunting challenge due to the presence of numerous potential interferents in these samples.

Solid-phase extraction (SPE) is considered the gold standard among conventional sample preparation techniques, routinely used for the pre-concentration and clean-up of the target analyte(s) from complex sample matrices for subsequent analysis (B. Buszewski, M. Szultka, Past, Present, and Future of Solid Phase Extraction: A Review, Critical Reviews in Analytical Chemistry, 42 (2012) 198-213). However, conventional silica-based sorbents (e.g., C8, C18, etc.) do not offer adequate selectivity and specificity because the target analytes are predominantly retained on these sorbents by non-specific hydrophobic interactions, leading to simultaneous co-extraction of numerous endogenous interfering substances from the sample, thereby complicating the subsequent chromatographic analysis.

Molecularly imprinted polymers (MIPs) are synthetic polymeric materials that possess specific cavities complimentary to the shape, size, and functional groups of a template molecule used in the imprinting process (Techniques and Instrumentation in Analytical Chemistry, in: S. Börje (Ed.) Techniques and Instrumentation in Analytical Chemistry, Elsevier2001, pp. ii; P. Manesiotis, L. Fitzhenry, G. Theodoridis, P. Jandera, 4.20—Applications of SPE-MIP in the Field of Food Analysis, in: J. Pawliszyn (Ed.) Comprehensive Sampling and Sample Preparation, Academic Press, Oxford, 2012, pp. 457-471; L. Chen, S. Xu, J. Li, Recent advances in molecular imprinting technology: current status, challenges and highlighted applications, Chemical Society Reviews, 40 (2011) 2922-2942).

Among many different synthesis pathways that can be used to create MIPs, the organic synthesis route appears to be the most popular (W. J. Cheong, S. H. Yang, F. Ali, Molecular imprinted polymers for separation science: A review of reviews, Journal of Separation Science, 36 (2013) 609-628). However, despite the advantages of organically synthesized MIPs, these materials often suffer from significant shortcomings, which include: (a) slow mass transfer kinetics; (b) heterogeneity of the binding sites; (c) low population of high-affinity binding sites; (d) irreversible shrinking and/or swelling when exposed to organic solvents, leading to considerable deformation of the imprinted cavities, and subsequent loss in template recognition capacity; (e) poor extraction performance when the sample matrices are aqueous or biological in nature and the target analytes are polar; (f) lack of ability to imprint thermal- and photosensitive template molecules due to the relatively high synthesis reaction temperature; (g) limited template removal option due to low thermal stability of organic polymers; and (h) low imprinting factor (IF) due to relatively high non-specific adsorption.

Some of these shortcomings of organic MIPs have been addressed by sol-gel synthesis approaches. Sol-gel synthesis of MIPs is versatile and possesses advantages including, for example, mild room temperature synthesis conditions, controllable pore size; high surface area, and tunable polarity of the matrix via manipulations in the sol-gel processing conditions such as, for example, the type and concentration of the precursors, catalysts, porogenic agents, and water content. The rigid, highly cross-linked structure of sol-gel MIPs possesses delicately imprinted sites with a high degree of selectivity compared to more flexible organic polymer MIPs.

Despite the potential of sol-gel organic-inorganic hybrid polymers as a host for efficient molecular imprinting, the advantages of these unique material systems have not been fully exploited. This is, in part, due to the lack of thorough understanding of sol-gel chemistry and the involvement of a large numbers of independent variables that eventually determine the ultimate physicochemical characteristics of the sol-gel materials. Irrational optimization of these variables often leads to sol-gel materials with poor accessibility to interaction sites, slow mass transfer rate, ineffective removal of the template, and low adsorption capacity.

Some researchers have proposed surface molecularly imprinted polymers (SMIP) using preformed silica particles as the imprinting host; however, due to the presence of a large number of residual surface silanol groups left on the silica substrate following the molecular imprinting, this approach often leads to high non-specific adsorption and results in low IF (J. Li, M. Yang, D. Huo, C. Hou, X. Li, G. Wang, D. Feng, Molecularly imprinted polymers on the surface of silica microspheres via sol-gel method for the selective extraction of streptomycin in aqueous samples, Journal of Separation Science, 36 (2013) 1142-1148; Y.-M. Yin, Y.-P. Chen, X.-F. Wang, Y. Liu, H.-L. Liu, M.-X. Xie, Dummy molecularly imprinted polymers on silica particles for selective solid-phase extraction of tetrabromobisphenol A from water samples, Journal of Chromatography A, 1220 (2012) 7-13; J.-H. Hu, T. Feng, W.-L. Li, H. Zhai, Y. Liu, L.-Y. Wang, C.-L. Hu, M.-X. Xie, Surface molecularly imprinted polymers with synthetic dummy template for simultaneously selective recognition of nine phthalate esters. Journal of Chromatography A. 1330 (2014) 6-13). As such, surface imprinting is not a viable solution for molecular imprinting if high IF, fast mass transfer kinetic, and high template adsorption capacity are desired.

Milk is a complicated sample matrix that requires multi-step sample preparation procedures. For the isolation of CAP in milk, various techniques have been proposed including liquid-liquid extraction (LLE) (X. Z. Shi, A. B. Wu, S. L. Zheng, R. X. Li, D. B. Zhang, Molecularly imprinted polymer microspheres for solid-phase extraction of chloramphenicol residues in foods, Journal of Chromatography B-Analytical Technologies in the Biomedical and Life Sciences, 850 (2007) 24-30), solid phase extraction (SPE) (R. S. Nicolich, E. Werneck-Barroso, M. A. S. Marques, Food safety evaluation: Detection and confirmation of chloramphenicol in milk by high performance liquid chromatography-tandem mass spectrometry, Analytica Chimica Acta, 565 (2006) 97-102; E. G. Karageorgou, V. F. Samanidou, Development and validation according to European Union Decision 2002/657/EC of an HPLC-DAD method for milk multi-residue analysis of penicillins and amphenicols based on dispersive extraction by QuEChERS in MSPD format, Journal of Separation Science, 34 (2011) 1893-1901; M. Ramos, A. Aranda, M. M. de Pozuelo, T. Reuvers, Chloramphenicol residues in food samples: Their analysis and stability during storage, Journal of Liquid Chromatography & Related Technologies, 26 (2003) 2535-2549), and fabric phase sorptive extraction (FPSE) (V. Samanidou, L. D. Galanopoulos, A. Kabir, K. G. Furton, Fast extraction of amphenicols residues from raw milk using novel fabric phase sorptive extraction followed by high-performance liquid chromatography-diode array detection, Analytica Chimica Acta, 855 (2015) 41-50). Deproteinization of milk is generally used prior to sample enrichment and clean-up by continuous solid phase extraction (D. R. Rezende, N. Fleury Filho, G. L. Rocha, Simultaneous determination of chloramphenicol and florfenicol in liquid milk, milk powder and bovine muscle by LC-MS/MS, Food Additives and Contaminants Part a-Chemistry Analysis Control Exposure & Risk Assessment, 29 (2012) 559-570).

The use of MIPs for the extraction and quantification of CAP in milk-based matrices has been suggested by Mohamed et al. in 2007 (R. Mohamed, J. Richoz-Payot, E. Gremaud, P. Mottier, E. Yilmaz, J. C. Tabet, P. A. Guy, Advantages of molecularly imprinted polymers LC-ESI-MS/MS for the selective extraction and quantification of chloramphenicol in milk-based matrixes. Comparison with a classical sample preparation, Analytical Chemistry, 79 (2007) 9557-9565). An improved method for trace analysis of CAP in honey, urine, milk and plasma using MIPs was proposed by Boyd et al., 2007 (B. Boyd, H. Bjork, J. Billing, O. Shimelis, S. Axelsson, M. Leonora, E. Yilmaz, Development of an improved method for trace analysis of chloramphenicol using molecularly imprinted polymers, Journal of Chromatography A, 1174 (2007) 63-71). The selective determination of CAP at trace levels in milk samples by an electrode modified with molecularly imprinted polymer has also been reported (T. Alizadeh, M. R. Ganjali, M. Zare, P. Norouzi, Selective determination of chloramphenicol at trace level in milk samples by the electrode modified with molecularly imprinted polymer, Food Chemistry, 130 (2012) 1108-1114). CAP was also identified in urine, feed water, milk and honey samples using molecular imprinted polymer clean-up by a commercially available MIPSPE column (Supel MIP) prior to GC/MS analysis after silylation of the antibiotic (M. Rejtharova, L. Rejthar, Determination of chloramphenicol in urine, feed water, milk, and honey samples using MIP clean-up, Journal of Chromatography A, 1216 (2009) 8246-8253). Although Supel MIP columns, presumably synthesized via an organic polymer approach, have demonstrated clear advantages over C18 SPE cartridges in extracting and pre-concentrating CAP from milk and other aqueous samples, due to the simultaneous extraction of non-specific matrix interferents from complex sample matrices, a series of washing steps had to be incorporated into the sample preparation regime followed by vacuum drying of the sorbent and subsequent elution of the analyte with larger volume of eluent.

As such, despite the inherent advantages over C18 SPE sorbent, the CAP imprinted Supel MIP method is labor-intensive, time-consuming and, contradictory to the principle of green analytical chemistry (GAC) (M. Farre, S. Perez, C. Goncalves, M. F. Alpendurada, D. Barcelo, Green analytical chemistry in the determination of organic pollutants in the aquatic environment, Trac-Trends in Analytical Chemistry, 29 (2010) 1347-1362; M. de la Guardia, Green analytical chemistry, Trac-Trends in Analytical Chemistry, 29 (2010) 577-577). Unavoidable application of solvent evaporation followed by sample reconstitution as an integral part of this sample preparation strategy often leads to irreversible analyte loss, poor data quality and low sample throughput.

No sol-gel derived CAP-imprinted sorbent material system has been reported for the separation and detection of this important analyte from milk or other biological samples.

BRIEF SUMMARY

The subject invention provides chemical compositions and synthesis strategies to create molecularly imprinted polymers (MIPs) via sol-gel processes. In a specific embodiment, the subject invention utilizes an organic, inorganic, or metallic target analyte to create a hybrid organic-inorganic or inorganic three-dimensional network possessing cavities complementary to the shape, size, and functional orientation of a target analyte. In some embodiments, the compositions of MIPs are obtained via a molarity-based approach. Advantageously, these cavities exhibit high affinity towards the target analyte, and its structural analogs, and remain indifferent to other molecules or species present in the same sample matrix.

In one embodiment, the subject invention provides a synthesis and post-synthesis processing strategy to effectively create cavities of a target analyte (e.g., molecules or ions) in a network comprising silica, zirconia, titania, germania, or a mixture thereof that demonstrate high affinity towards the template analyte, similar to antibody-antigen interactions. Advantageously, the sol-gel inorganic and/or hybrid organic-inorganic polymeric networks provided herein possess advanced material properties such as, for example, adjustable porosity, tunable selectivity, high thermal and solvent stability, and stability over a wide range of pH.

In exemplary embodiments, the formulations, the synthesis, and post-synthesis processing strategies provided herein were rigorously tested using chloramphenicol (CAP), a veterinary antibiotic as a model target analyte. The CAP-imprinted sol-gel inorganic-organic hybrid polymeric sorbents were found to be highly selective towards trace amounts of CAP and indifferent towards matrix interferents present in biological samples such as milk. Synthesis of other MIPs with environmental, pharmaceutical, chemical, clinical, toxicological, and national security implications can be conducted in accordance with teachings of the subject invention. Many such examples are provided herein.

Advantageously, exemplary embodiments provide advanced sorbent material systems with predesigned cavities in a sol-gel hybrid organic-inorganic polymeric substrates for efficient extraction and/or pre-concentration of a variety of target analytes such as, for example, organic/inorganic molecules, organic/inorganic ions, and heavy metals from different sample matrices including, for example, forensic specimens; trace organic pollutants from environmental, food, beverage, pharmaceutical, and chemical samples; and drug or poison residues and metabolites thereof from biological samples.

BRIEF DESCRIPTION OF DRAWINGS

FIGS. 4A-4B show the BET adsorption isotherm graphs for (4A) sol-gel MIP and (4B) sol-gel NIP, respectively.

FIG. 5 shows the retention capacity of the sol-gel MIPSPE sorbent material.

DETAILED DISCLOSURE

Figure 1:
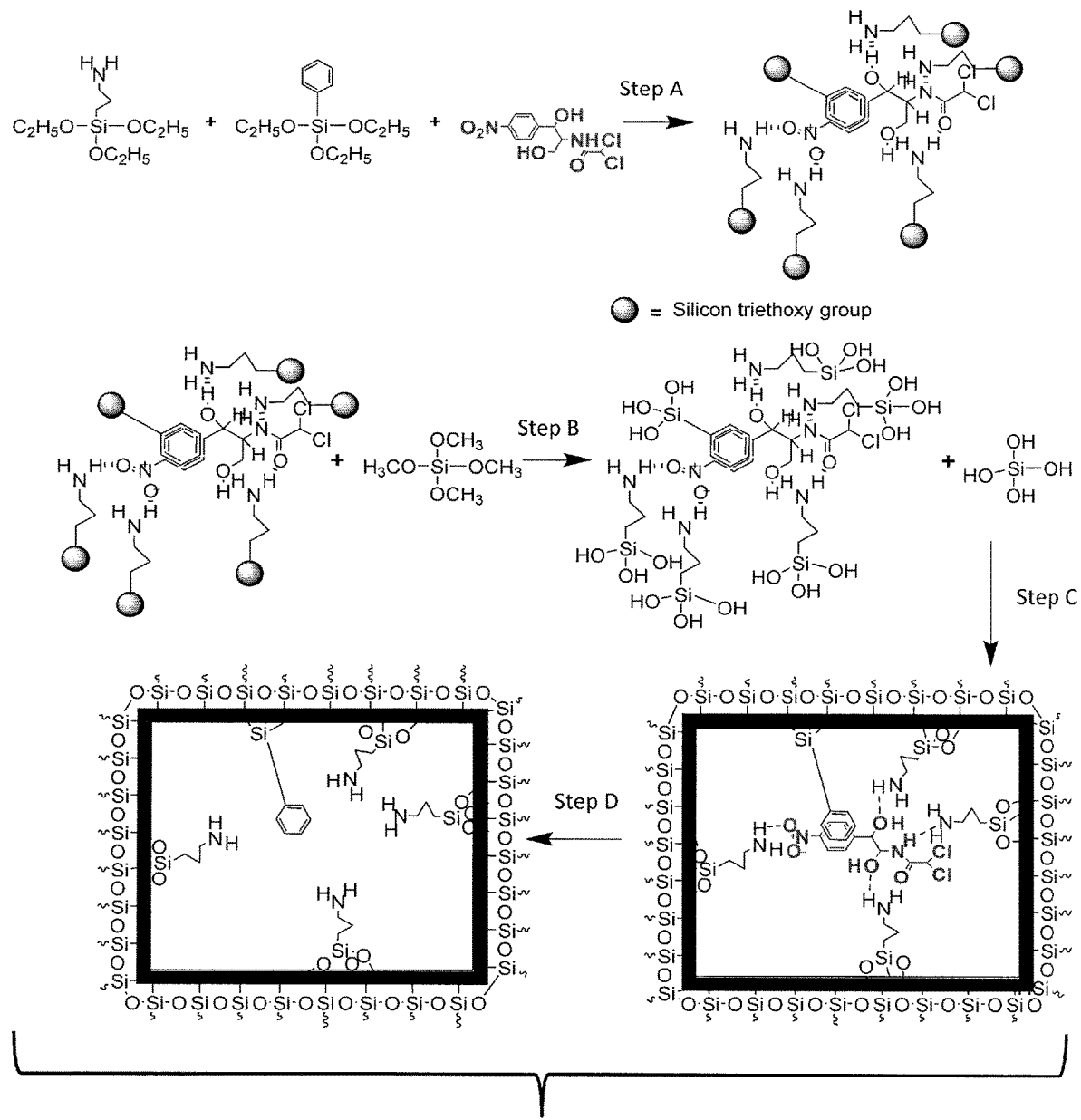
FIG. 1 shows the synthesis scheme of a chloramphenicol (CAP)-imprinted sol-gel MIP comprising the following steps: (Step A) complexation of 3-APTES and triethoxyphenylsilane with the CAP template; (Step B) acid-catalyzed hydrolysis of the sol-gel precursors; (Step C) condensation of hydrolyzed precursors to form a 3D sol-gel networks with the encapsulated templates; and (Step D) removal of the template from sol-gel 3D polymeric networks.
Figure 2A:
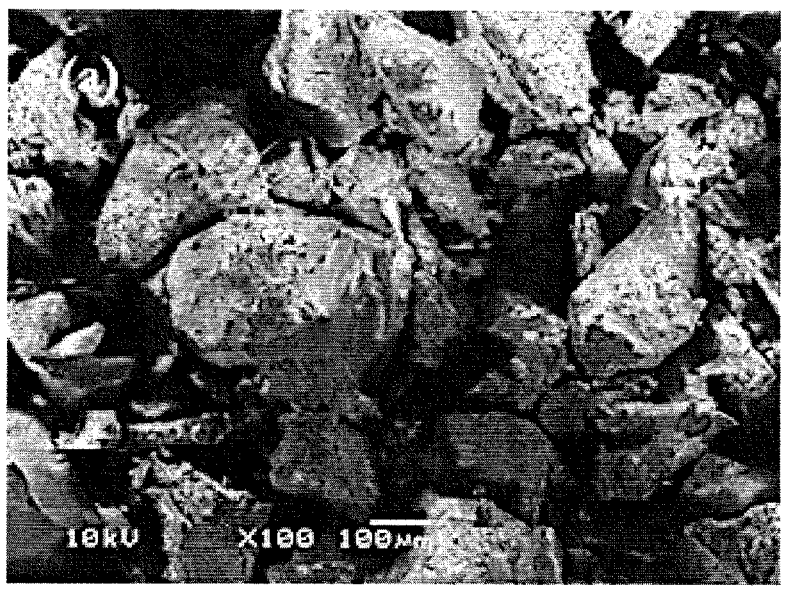
FIGS. 2A-2D show SEM images of CAP-imprinted sol-gel (MIP) at (2A) 100× and (2B) 500× magnification, and non-imprinted sol-gel (NIP) at (2C) 100× and (2D) 500× magnification.
Figure 2B:
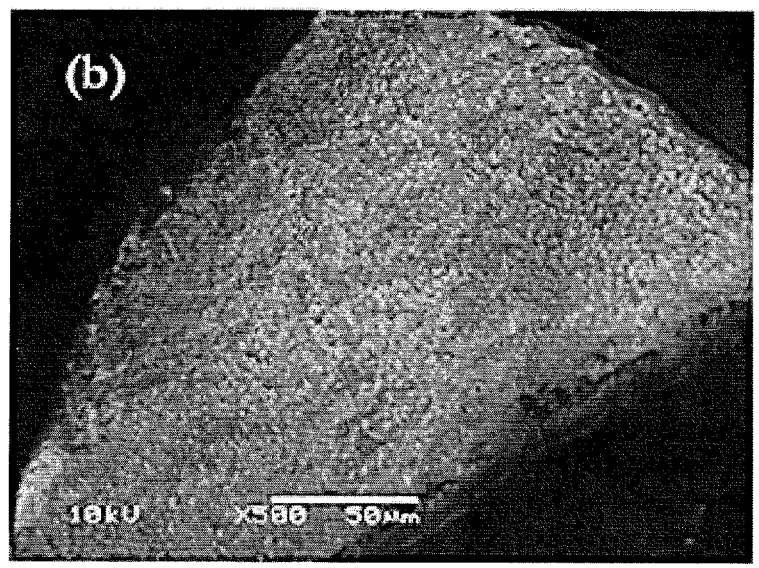
Figure 2C:
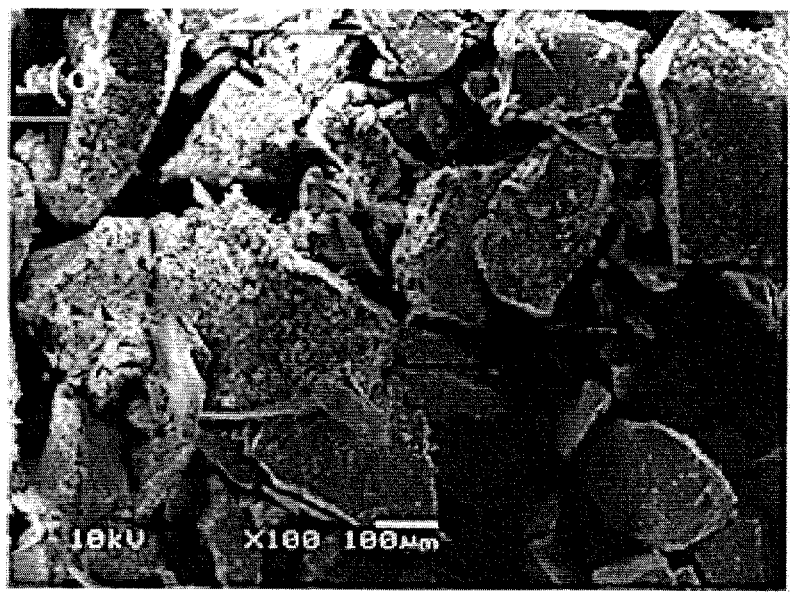
Figure 2D:
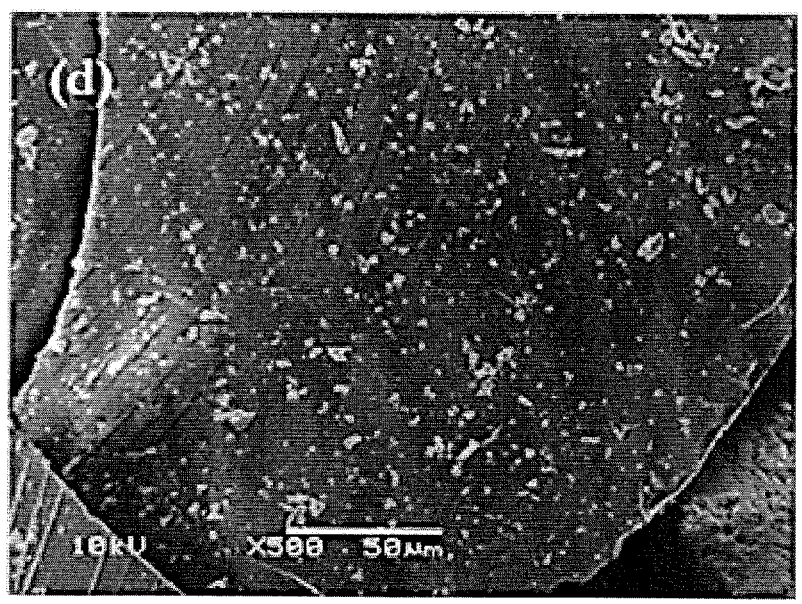

The subject invention provides chemical compositions and synthesis strategies to create molecularly imprinted polymers (MIPs) via sol-gel processes. In a specific embodiment, the subject invention utilizes an organic, inorganic, or metallic template analyte to create a hybrid organic-inorganic or inorganic three-dimensional network possessing cavities complementary to the shape, size, and functional orientation of the template molecule or ions. The subject invention further pertains to the use of the novel MIPs as selective solid phase extraction (SPE) sorbents for pre-concentration and clean-up of trace substances in biological and environmental samples. Synthesis of other molecularly imprinted polymers with environmental, pharmaceutical, chemical, clinical, toxicological, and national security implications can be conducted in accordance with the teachings of the subject invention.

The term "complementary" as used herein indicates that each molecular cavity left behind in the MIP matrix has a size matching that of the target analyte as well as binding site(s) with affinity towards chemical functional groups present in the analyte. In some embodiments, the target analyte can be eluted or extracted from the polymer matrix using a number of methods. In certain embodiments, the extraction can be done using an appropriate solvent such as, for example, methanol, ethanol, isopropanol, acetonitrile, formic acid, acetone, and combinations thereof. In further embodiments, the binding between the target analyte and its complementary molecular cavities is reversible.

In some embodiments, non-limiting examples of target analytes that can be imprinted in sol-gel MIP matrix provided herein include drugs, biological molecules (e.g., cells, proteins, carbohydrates, and amino acids), toxins, viruses, and structural analogues thereof.

In some embodiments, the target analyte is an antibiotic selected from chloramphenicol (CAP), thiamphnicol, florfenicol, ceftiofur, cefaclor, oxytetracycline, tetracycline, sulfamethazine, sulfadimethoxine. amoxicillin, ampicillin, ciprofloxacin, enrofloxacin, and structural analogues thereof. In an exemplary embodiment, the target analyte is CAP. Many more target analytes are provided in Example 14.

In some embodiments, the subject invention provides facile synthesis and post-synthesis processing strategies to create cavities of a template molecule or template ion on a network comprising silica, zirconia, titania, and/or germania, or a mixture thereof that demonstrates high affinity towards the target analyte. Advantageously, the sol-gel inorganic and/or hybrid organic-inorganic polymeric networks provided herein possess advanced material properties such as, for example, adjustable porosity, tunable selectivity, high thermal and solvent stability, and stability over a wide range of pH.

Specifically exemplified herein is the detection of CAP from milk samples and the subsequent separation and quantification thereof using high-performance liquid chromatography (HPLC) equipped with ultra-violet (UV) and/or mass spectrometry (MS) detection. Non-limiting examples of other samples that may comprise CAP include blood, plasma, serum, and urine.

In a specific embodiment, an MIP imprinted with CAP is synthesized via a sol-gel matrix imprinting approach by employing triethoxyphenylsilane (TEPS) and 3-aminopropyltriethoxysilane (3-APTES) as sol-gel functional precursors, tetramethyl orthosilicate (TMOS) as the cross-linking precursor, water as the hydrolytic agent, HCl as the catalyst, and isopropanol as the polymerization solvent, resulting in a hybrid inorganic-organic 3D network.

As described herein, both the sol-gel MIP and sol-gel non-imprinted polymer (NIP) have been synthesized and characterized using different techniques such as, for example, scanning electron microscopy (SEM), Fourier-transform infra-red spectroscopy (FT-IR), and nitrogen adsorption porosimetry. Those skilled in the art would recognize that other characterization techniques now known or hereafter developed can also be used to analyze the MIPs and NIPs networks provided herein.

The MIPs synthesized using compositions and methods provided by the subject invention have many advantages. For example, simultaneous exploitation of two functional precursors in the molecular imprinting process results in a high imprinting factor (IF). In an exemplary embodiment, the IF for CAP-imprinted MIP is approximately 9.7. Relatively low IFs for other analogous compounds indicate a high degree of selectivity of molecular cavities for CAP. Advantageously, these cavities exhibit high affinity towards the target analyte, or its structural analogs, and simultaneously remain indifferent, or chemically inert and unreactive, toward other molecules or species present in the same sample matrix.

In an exemplary embodiment, the sol-gel MIP sorbent provided herein demonstrates good extraction and pre-concentration performance for isolating CAP from milk and can be used up to, for example, two, three, four. five, or six times without significantly losing its extraction capacity. The synthesized sol-gel MIP also exhibited low cross reactivity with antibiotics of other classes. The method was validated according to the EU criteria for confirmatory analytical methods. Advantageously, this highly efficient sol-gel MIP can be routinely used in testing laboratories to ensure food quality and consumer safety for the trace analysis of CAP in milk samples. It is an advantageous feature of the subject invention that the CAP-imprinted MIP is indifferent towards other matrix interferents present in samples such as, for example, milk, highlighting the sensitivity and selectivity of the sol-gel MIP matrix provided herein.

In the sol-gel matrix imprinting process exemplified herein, CAP was used as the template molecule, 3-aminopropyltriethoxysilane and triethoxyphenylsilane as the functional precursors, tetramethyl orthosilicate as the cross-linker, isopropanol as the solvent/porogen, and HCl as the sol-gel catalyst. By comparison, sol-gel NIP was also synthesized under identical conditions in the absence of the template molecules. Both the sol-gel MIP and sol-gel NIP were subjected to physicochemical characterization by scanning electron microscopy (SEM), Fourier transform infrared spectroscopy (FT-IR), and nitrogen adsorption porosimetry. Characterization results demonstrated significant structural and morphological differences between sol-gel MIP and sol-gel NIP sorbents, thus confirming the effectiveness of the sol-gel MIP matrix and the synthesis methods thereof as provided herein.

In some embodiments, the synthesized sol-gel MIP and sol-gel NIP were evaluated as sorbents for molecularly imprinted solid-phase extraction (MISPE) of CAP in milk samples. The effect of critical solid-phase extraction parameters such as flow rate, nature of the eluent, sample and eluent volume, selectivity coefficient, and retention capacity were studied with regards to the retention and desorption of CAP to the CAP-imprinted sol-gel MIP sorbent.

In some embodiments, the subject invention provides an apparatus in which a sol-gel sorbent material (e.g., the CAP-imprinted sol-gel MIP) can be stored and a sample of interest (e.g., milk) can be subsequently passed through to allow the extraction of a target analyte. In an exemplary embodiment. the apparatus is a syringe equipped with, for example, a barrel for storing the sorbent material and a plunger to push a sample through the sorbent. Alternatively, the apparatus can be a solid-phase extraction cartridge.

Competition and cross reactivity tests demonstrated that the sol-gel MIP sorbent possesses significantly higher specific retention and enrichment capacity for CAP compared to its non-imprinted analogue. The maximum imprinting factor (IF) was found to be 9.7, and the highest adsorption capacity of CAP by the sol-gel MIP was determined to be 23 mg/g. The sol-gel MIP was found to be sufficiently selective towards CAP to provide the necessary maximum required performance limit (MRPL) of 0.3 µg/kg for CAP as set forth by European Commission when LC-MS was deployed as the analytical instrument.

Advantageously, exemplary embodiments of the subject invention provide advanced sorbent material systems with predesigned cavities in sol-gel hybrid organic-inorganic polymeric substrates for efficient extraction and/or pre-concentration of a variety of target analytes such as, for example, organic/inorganic molecules, organic/inorganic ions, and heavy metals from different sample matrices including, for example, forensic specimens; trace organic pollutants from environmental, food, beverage, pharmaceutical, and chemical samples; and drug or poison residues and metabolites thereof from biological samples.

EXAMPLES

Following are examples which illustrate procedures for practicing the invention. These examples should not be construed as limiting. All percentages are by weight and all solvent mixture proportions are by volume unless otherwise noted.

Chloramphenicol (CAP) was purchased from Alfa-Aesar (Karlsruhe, Germany). thiamphenicol (TAP) and florfenicol (FFC) were purchased from Sigma-Aldrich (St. Louis, Mo., USA). HPLC grade methanol and acetonitrile were obtained from Fisher Scientific (Steinheim, UK), isopropanol (2-propanol) was supplied by Panreac (Barcelona, Spain). Acetone (p.a.) was supplied by Chem-Lab NV (Zedelgem, Belgium). HPLC grade water by Merck (Darmstadt, Germany) was used in mobile phase preparation, while high purity water, obtained by a Milli-Q purification system (Millipore, Bedford, Mass., USA), was used throughout the following examples. Formic acid (99-100%) was obtained from Chem-Lab and acetic acid glacial (100%) was purchased from Merck.

Additional antibiotics used for cross reactivity studies included sulfamethazine, sulfadimethoxine, cefaclor, ceftiofur, amoxicillin, ampicillin and ciprofloxacin, which were purchased from Sigma-Aldrich (St. Louis, Mo., USA). Enrofloxacin, tetracycline and oxytetracycline were purchased from Fluka Chemie (Buchs, Belgium).

Milk samples were collected from local food stores. Different varieties of fresh milk were analysed: (a) skim milk (0% fat), (b) semi-skim milk (1.5% fat), and (c) full-fat milk (3.5% fat). All milk samples were refrigerated at 4° C.

Example 1—Preparation of Sol-Gel MIP and Sol-Gel NIP

Preparation of Chloramphenicol Complex with Functional Precursors

The synthesis scheme of CAP imprinted sol-gel MIP is shown in FIG. 1. The self-assembled complex between the CAP template and the sol-gel precursors, 3-APTES and TEPS were obtained by vigorously mixing 250 mg of CAP, 0.8 g of 3-APTES, 0.8 g of TEPS, and 4 mL of isopropanol together followed by sonication for 30 min. The mixture was incubated at room temperature for 6 hr so that a 3D complex with distinct stereo-chemical orientation between the template and the sol-gel precursors forms via hydrogen bonding.

The schematic process presented in FIG. 1 comprises four steps, including (Step A) complexation of sol-gel functional precursors (e.g., 3-APTES and TEPS) with CAP template; (Step B) acid-catalyzed hydrolysis of crosslinking sol-gel precursor; (Step C) simultaneous hydrolysis of functional precursors and condensation of hydrolyzed precursors to form a 3D sol-gel network with encapsulated template analyte; and (Step D) removal of the template from the sol-gel 3D polymeric network.

Due to the presence of a benzene ring as well as a large number of hydrogen bond donors and acceptors in CAP, TEPS (to provide µ-µ interaction), and 3-APTES (to provide hydrogen bonding interaction) were chosen.

During the complexation, both of the sol-gel precursors positioned themselves around the template utilizing their specific interaction capability. As such, a template-precursors complex was formed with a distinct 3D stereo-chemical orientation of the participating entities. To ensure uninterrupted interactions between the template and precursors, isopropanol, a relatively nonpolar solvent, was used as the reaction medium.

Another important task in sol-gel MIP synthesis is to obtain complete hydrolysis of the crosslinking sol-gel precursors in order to ensure successful integration of the template complex into the 3D sol-gel network. Complete hydrolysis of the methoxy functional groups into hydroxyl functional groups was ensured by dissolving TMOS in an appropriate volume of solvent/porogen isopropanol and reacting with water in the presence of HCl as a catalyst for a prolonged period of time under elevated temperature.

Hydrolysis of the Crosslinking Agent

To initiate the hydrolysis of the crosslinking agent, 2.5 mL of TMOS was added to 20 mL of isopropanol and the mixture was thoroughly mixed by vortexing for 5 min. Subsequently, 750 µL of 0.1 M HCl was added to the mixture and kept in a silicone oil bath at 50° C. for 12 hr to ensure complete hydrolysis of the sol-gel precursor.

Sol-Gel Condensation to Form 3D Molecularly Imprinted Polymer (MIP) Network

The complex mixture containing the template was then added to the hydrolyzed solution of the cross-linking reagent and was vortexed for another 5 min. The sol solution comprising the CAP template was kept at 50° C. in the silicone oil bath for 4 hr to form a transparent gel mixture, followed by another 24 hr at the same temperature for aging and ripening of the network.

When the template-precursors complex is added to the sol solution containing the hydrolyzed crosslinking agent, simultaneous hydrolysis and condensation of the functional precursors as well as the condensation of the hydrolyzed crosslinking agent began in the presence of the acid catalyst HCl and at an elevated reaction temperature. Soon, a 3D network of sol-gel polymeric network with entrapped template and solvent/porogen self-assembled.

Removal of the Template from Sol-Gel MIP Sorbent

Following the preparation of sol-gel MIP sorbent, the template (CAP) was removed from the polymer networks so that the imprinted cavities complimentary to the size, shape, and functionality of the template molecules were left behind throughout the matrix. Experiments showed that methanol (MeOH) was suitable for the removal of CAP from the sol-gel MIP sorbent after 10 cycles of sonication with 10 mL of MeOH for 30 min. Alternatively, 10 times of centrifugation for 30 min with 10 mL MeOH at 1900 g may be used for the exhaustive removal of the template. Solvent mediated template removal continued until the washing solution became free of CAP, which was confirmed by HPLC analysis.

The template-free particulates were then dried in an oven at 50° C. for 30 min. Non-imprinted sol-gel polymer sorbent (sol-gel NIP) was prepared following the same procedures established herein in the absence of the CAP template.

Aging and ripening of the sol-gel network for a prolonged period of time ensures that condensation has completed and as a result, the subsequent removal of the solvent and the template analyte from the sol-gel network would not disturb its structural and morphological integrity.

Example 2—Characterization of Sol-Gel MIP and Sol-Gel NIP: SEM

The CAP-imprinted sol-gel MIP sorbent as well as the NIP control sample were characterized using scanning electron microscopy (SEM). The SEM images are presented in FIGS. 2A-2D.

The surface morphology of both the imprinted and non-imprinted particulates appeared to be identical at lower magnification (100×); however, at higher magnification (500×), the imprinted surface demonstrates a sponge-like, porous, and roughened surface morphology, while the non-imprinted control shows a smooth, glassy surface at the same magnification.

Example 3—Characterization of Sol-Gel MIP and Sol-Gel NIP: FT-IR

Figure 3A:
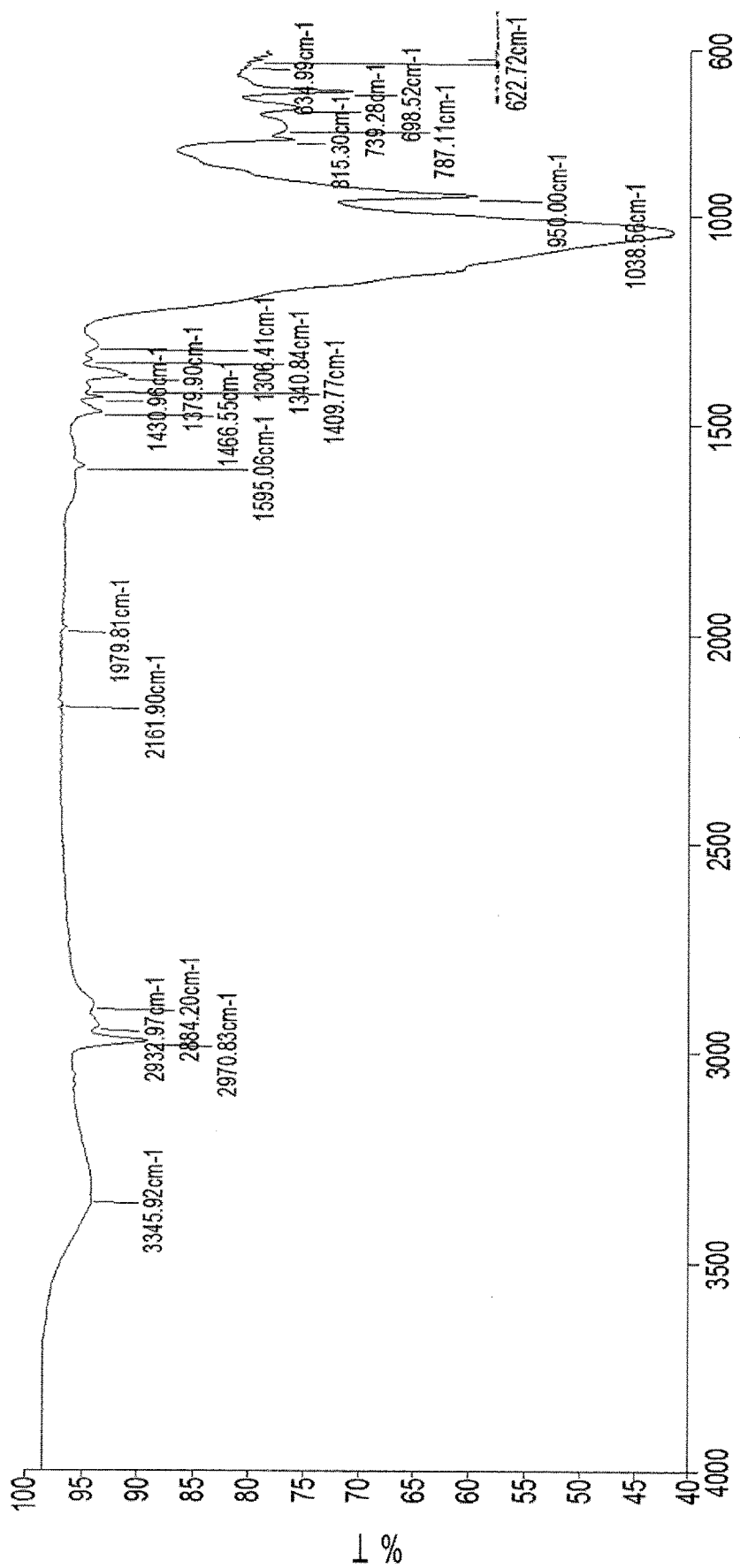
FIGS. 3A-3C show the FT-IR spectrum of (3A) sol-gel MIP, (3B) sol-gel NIP, and (3C) a CAP template molecule, respectively.
Figure 3B:
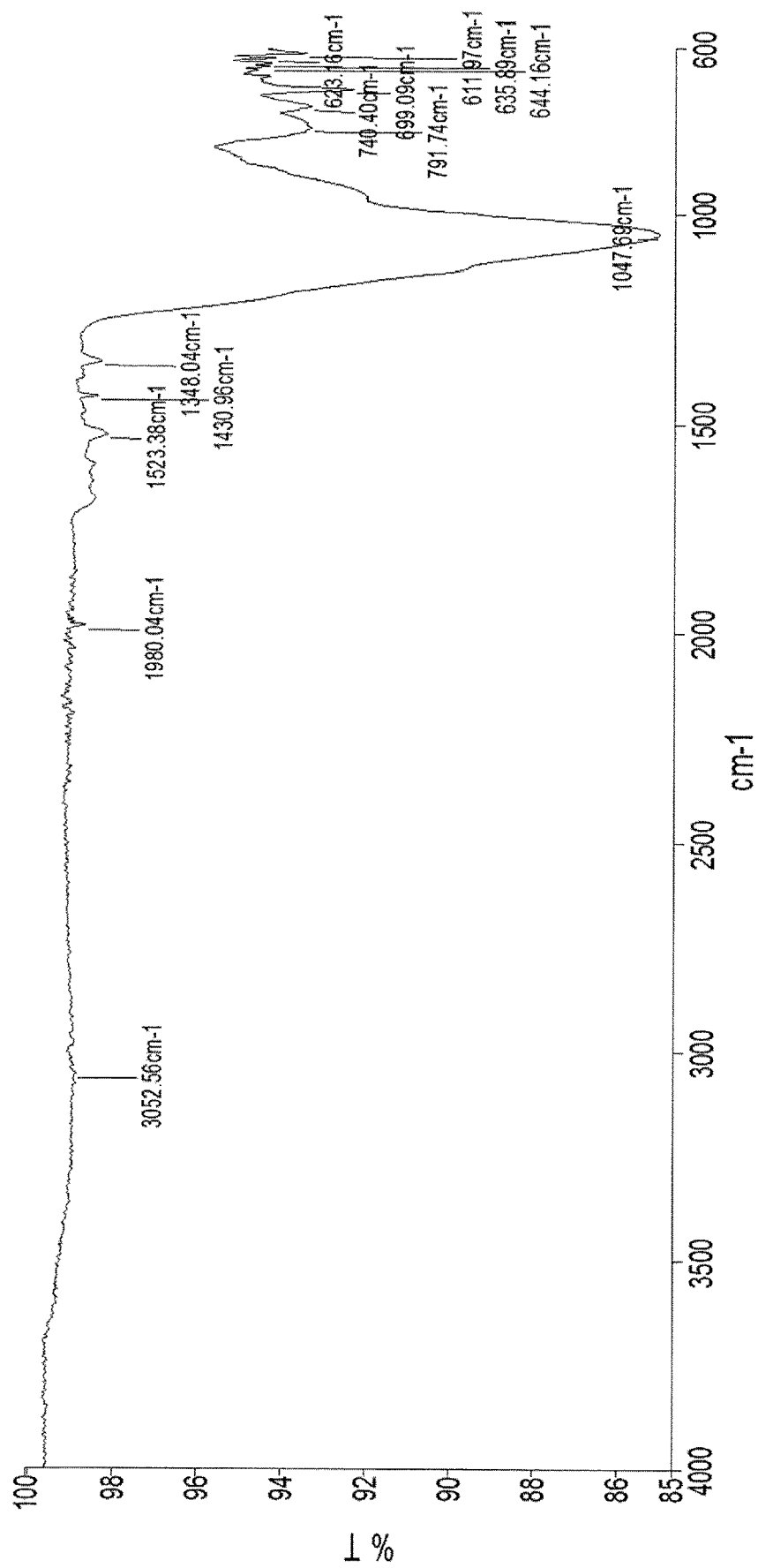
Figure 3C:
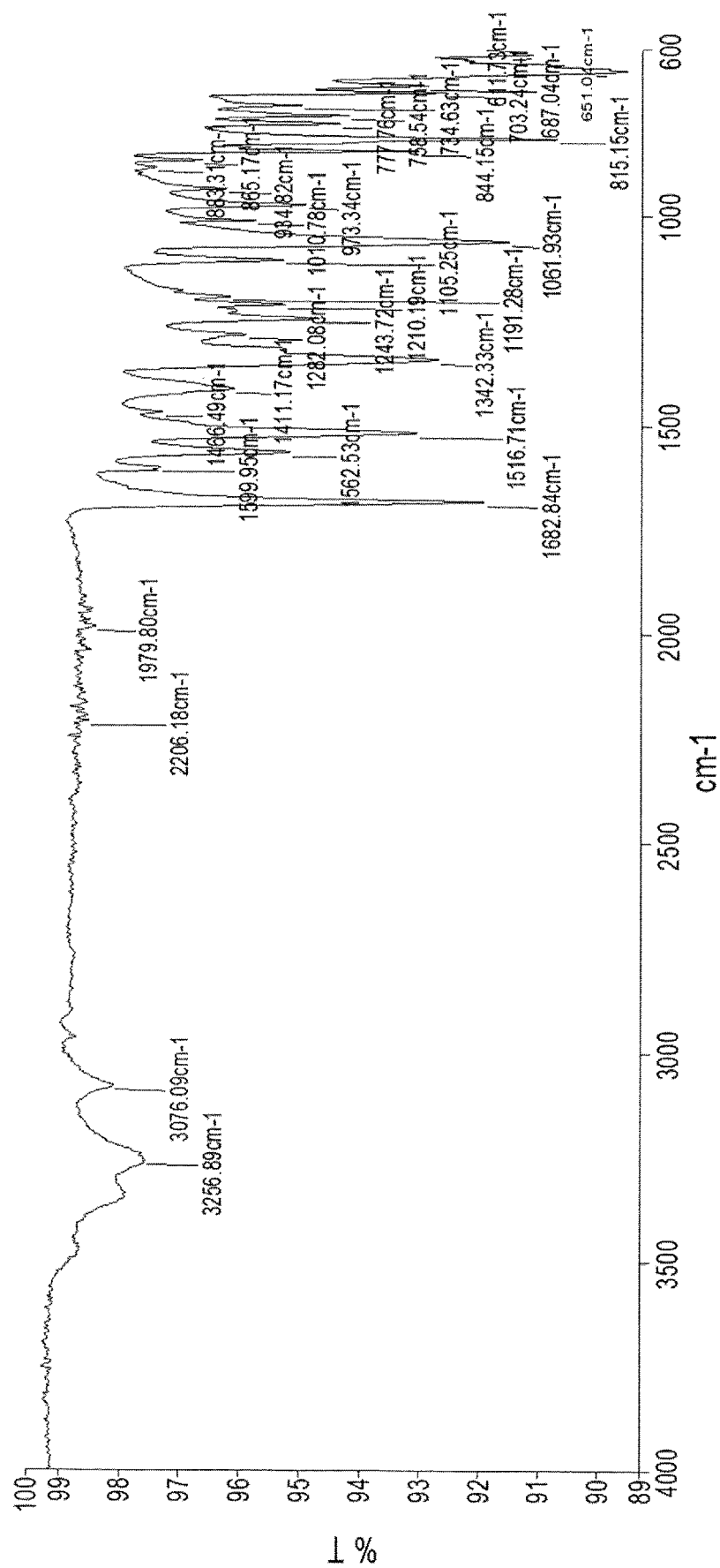

To study the presence of various functional groups and the chemical linkages within the sol-gel MIP and sol-gel NMIP sorbents, Fourier transform infra-red spectroscopy (FT-IR) was employed. FIGS. 3A-3C show the FT-IR spectrum of (a) the sol-gel MIP, (b) the sol-gel NIP, and (c) the CAP template, respectively.

The spectral features observed in FIGS. 3A and 3B around 1038-1047 $cm^{-1}$ were attributed to Si—O—Si stretching vibrations. The bands around 787-792 $cm^{-1}$ represent Si—O vibrations. The bands around 1595 $cm^{-1}$ are resulted from nitro phenyl group of the sol-gel precursor, 3-APTES. Bands at 698 $cm^{-1}$ and 739 $cm^{-1}$ were attributed to another sol-gel precursor, TEPS.

The absence of any features of CAP as shown in FIG. 3C in both the sol-gel MIP and sol-gel NIP strongly suggests the successful quantitative removal of the template molecules from the sol-gel MIP.

Example 4—Characterization of Sol-Gel MIP and Sol-Gel NIP: HPLC-UV

An LC-10AD pump by Shimadzu (Kyoto, Japan) was used to deliver the mobile phase to the analytical column. The sample was injected via a Rheodyne 7125 injection valve (Rheodyne, Cotati, Calif., USA). UV Detection was achieved at a sensitivity setting of 0.0005 AUFS using an SSI 500 UV-vis detector (SSI, State College, Pa., USA).

Milli-Q water, included in the mobile phase, was filtered using a glass vacuum-filtration apparatus obtained from Alltech Associates, (Deerfield, Ill., USA) and Whatman Cellulose Nitrate 0.2 mm—WCN Type (47 mm DIA) membrane filters (Whatman Laboratory Division, Maidstone, England). Degassing of solvents was achieved by helium sparging prior to use.

Sonication was performed by an ultrasonic bath Transonic 460/H (35 kHz, 170 W, Elma, Germany) and centrifugations were carried out using a Hermle centrifuge, model Z-230 (B. Hermle, Gosheim, Germany). A Visiprep™ SPE vacuum manifold by Supelco (Bellefonte, Pa., U.S.A.), a nine port Reacti-Vap™ (model 18780) by PIERCE (Rockford, Ill., USA) were used.

A PerfectSil 120 ODS-2 analytical column (250 mm×4.0 mm, 5 μm) by MZAnalysenTecnhik (Mainz, Germany) was used for the separation at ambient temperature. The mobile phase consisted of acetonitrile-water (30:70%, v/v) and was delivered isocratically at a flow rate of 1.0 mL/min. Aliquots of 20 μL were injected. Monitoring and quantitation of CAP was performed at 280 nm.

Example 5—Characterization of Sol-Gel MIP and Sol-Gel NIP: LC-MS

LC-MS analysis was performed using a Shimadzu LCMS-2020 (Kyoto, Japan) mass spectrometer. Standard LC-20AD dual pistons and pumps with high-pressure mixing provided flow (0.5 mL/min) for the interface and the detector. Samples were injected (50 μL volume) by a Shimadzu SIL-20AC HT autosampler, which operated for both flow and column injection analysis. The LC-MS-2020 was operating in the negative ionization SCAN and the selected ion monitoring (SIM) modes. Scans were made from 50-500 at 0.5-s intervals (scan speed=1500 amu/s). Initially, the main (−) m/z ion for each analyte in the scan method was chosen and then the analysis was repeated at the SIM mode and its response ions was measured. The results were verified by triplicate measurements.

The sample solution was drawn into a capillary pipe with a high voltage of −3.5 kV applied. Nebulizer gas was blown out around the outside of the capillary pipe, spraying the solution and generating fine droplets electrostatically charged with the same sign as the applied voltage. Interface temperature was maintained at 350° C. After being sprayed and ionized by the ionization probe, the sample passed through the sample introduction line (Desolvation Line-DL) oriented at 250° to the spray, into the first stage primary vacuum chamber (lens system). Excess solvent was expelled through the drainage port.

The temperature and voltage of the curved desolvation line (the inlet for the high vacuum region) were set at 250° C. and 0 V, while the nitrogen nebulizer gas flow remained constant at 1.5 L/min, respectively. Drying gas flow was set at 15 L/min. CAP was identified in negative scan mode at m/z=321. Mobile phase in LC-MS analysis was MeOH—$H_2O$ (at v/v of 40:60). Methanol was chosen as the mobile phase due to its ability to provide higher signal than acetonitrile-water mixture.

Example 6—Characterization of Sol-Gel MIP and Sol-Gel NIP: Nitrogen Adsorption Porosimetry The textural characteristics of sol-gel MIP and sol-gel NIP particles were investigated using nitrogen adsorption/desorption isotherm.

The BET adsorption isotherm graphs for sol-gel MIP and sol-gen NIP are presented in FIGS. 4A and 4B. The adsorption data are presented in Table 1 below.

TABLE 1

BET surface area ($m^2$/g), pore volume, and average pore diameter of CAP-imprinted sol-gel polymer and corresponding sol-gel non-imprinted polymer.

| Polymer | BET surface area ($m^2 \cdot g^{-1}$) | Pore volume ($cm^3 \cdot g^{-1}$) | Average pore diameter (Å) |
|---|---|---|---|
| Sol-gel MIP | 167.3 | 0.1075 | 25.7 |
| Sol-gel NMIP | 67.6 | 0.0424 | 25.1 |

The specific surface area and the pore volume of the sol-gel MIP and the sol-gel NIP were significantly different from each other. The high specific surface area and larger pore volume of sol-gel MIP were good indicators of the relatively open 3D sol-gel network imparted by the presence of the self-assembled complex of the sol-gel precursors around the template molecules in a rigid stereo-chemical orientation. However, the average pore diameter of both imprinted and non-imprinted materials are similar, suggesting that the presence of porogen (e.g., isopropanol), and not the template, in the sol solution contributed primarily to the pores of the sol-gel polymeric network.

The specific surface area of the sol-gel MIP was calculated to be 167. 3 $m^2$/g, which was significantly higher than that of both commercial silica (20 $m^2$/g) (W. Chen, Z. Fan, A. Dhanabalan, C. Chen, C. Wang, Mesoporous Silicon Anodes Prepared by Magnesiothermic Reduction for Lithium Ion Batteries, Journal of The Electrochemical Society, 158 (2011) A1055-A1059) and the sol-gel NIP. Both the sol-gel MIP and sol-gel NIP possess mesopores that allowed fast diffusion of the aqueous sample through the sol-gel sorbent matrix to achieve extraction equilibrium in a relatively short period of time.

Example 7—Evaluation of the Performance of MIPS: Enrichment Factor

The enrichment factor is a vital parameter in evaluating the extraction efficiency. The enrichment factor (EF) is calculated to be:

$$EF = V_{sample}/V_{eluent} = 10 \text{ mL}/0.5 \text{ mL} = 20$$

where $V_{sample}$ is the volume of the sample and $V_{eluent}$ is the volume of eluent solvent. In case of evaporation and reconstitution to 100 µL, the EF was 100.

Example 8—Evaluation of the Performance of MIPS: Retention Capacity of the Cap-Imprinted Sol-Gel Sorbent To determine the retention capacity (or sorption capacity) of the sol-gel derived CAP-imprinted polymer (maximum amount of the template retained by 1 g of MIP), 30 mg of polymer were saturated with CAP by passing several 5.0 mL aliquots of 100 mg/L CAP solution. After measuring the CAP content in elutes by HPLC, the retention capacity of the polymer was calculated to be 23 mg/g, as shown in FIG. 5.

Example 9—Evaluation of the Performance of MIPS: Selectivity of Cap Imprinted Sol-Gel Sorbent To establish the selectivity of a sol-gel MIP for a particular analyte, a non-imprinted polymer (sol-gel NIP) is synthesized in the same way as sol-gel MIP but in the absence of the template.

The IF reflects the tendency of the MIP to selectively recognize and bind the template. Competitive adsorption of MIP and NIP for CAP was investigated in a MIPSPE column system. The IF and the selectivity coefficient (SC) are indicators of the adsorption affinity of recognition sites to the imprinted CAP.

Selectivity Studies

The selectivity of sol-gel MIP particles for CAP was studied. For this purpose, 30 mg of sol-gel MIP or sol-gel NIP particles were packed in SPE cartridges. Aqueous sample solutions containing 10 ng/mL CAP was passed through the SPE cartridges holding imprinted or non-imprinted particles at a flow rate of 1 mL/min by the aid of a vacuum system. Elution of the extracted chloramphenicol was performed using methanol and the concentration of chloramphenicol was determined by the HPLC-UV method.

Imprinting factor (IF) of sol-gel MIP particles was determined by the following equation:

$$IF = K_{mip}/K_{nip}$$

where $K_{mip}$ and $K_{nip}$ are the partition coefficient of analyte for sol-gel MIP and sol-gel NIP, respectively, which are determined by $K = C_b/C_u$ where $C_b$ is the amount of CAP bound by the sol-gel MIP or sol-gel NIP and $C_u$ is the concentration of free chloramphenicol that remained in the solution.

Selectivity coefficient (SC) was calculated by the following equation:

$$SC = IF_{CAP}/IF_{other\_analyte}$$

Cross reactivity of sol-gel MIP towards other antibiotics was studied using several antibiotics of similar structure such as, for example, thiamphnicol and florfenicol, as well as other antibiotics with different structure and functional groups such as, for example, ceftiofur, cefaclor, oxytetracycline, tetracycline, sulfamethazine, sulfadimethoxine, amoxicillin, ampicillin, ciprofloxacin, and enrofloxacin. The binding efficiency was evaluated and was found to be less than 5% for the other antibiotics, thus indicating the high specificity of the prepared sol-gel MIP.

Specifically, Table 2 and Table 3 summarize the IF and SC values for CAP compared to its analogues when extraction was carried out from untreated raw milk and protein precipitated milk, respectively.

TABLE 2

Imprinting factors and selectivity coefficients for CAP and its analogues.

| Analyte | Imprinting Factor (IF) | Selectivity Coefficient (SC) |
|---|---|---|
| CAP | 5 | — |
| THF | 1.9 | 2.6 |
| FFC | 1.8 | 2.8 |

TABLE 3

Effect of protein precipitation agent to the IF of sol-gel MIP

| Protein precipitation agent | Recovery | IF |
|---|---|---|
| Acetonitrile, ACN | 22.8 | 1.83 |
| Formic acid, HCOOH 25% | 9.8 | 9.7 |
| Acetic Acid, CH₃COOH 25% | 2.6 | 1.75 |

An imprinting factor of 9.8 was measured for the CAP-MIP relative to the corresponding NIP when extraction was carried out from protein precipitated milk sample. This signifies a strong selective binding in the imprinted sites of the MIP for CAP. An imprinting factor of 5.0 was obtained when CAP was extracted from untreated milk. The discrepancy in the imprinting factor values can be explained by the fact that untreated milk is a colloidal system containing protein, fat, lipid, and other nano-size particles that may block the imprinted cavities, resulting in lower imprinting factors.

An imprinting factor of 1.9 and 1.8 was noticed for CAP analogues such as other amphenicols, namely thiamphenicol and florfenicol, respectively. The large difference in the IF for the template and its close structural analogs reflects the excellent specificity of the sol-gel MIP towards CAP. The typical imprinting factor reported in organically synthesized MIPs are in the range of 1-2 (J. Li, M. Yang, D. Huo, C. Hou, X. Li, G. Wang, D. Feng, Molecularly imprinted polymers on the surface of silica microspheres via sol-gel method for the selective extraction of streptomycin in aqueous samples, Journal of Separation Science, 36 (2013) 1142-1148; Y.-M. Yin, Y.-P. Chen, X.-F. Wang, Y. Liu, H.-L. Liu, M.-X. Xie, Dummy molecularly imprinted polymers on silica particles for selective solid-phase extraction of tetrabromobisphenol A from water samples, Journal of Chromatography A, 1220 (2012) 7-13; J.-H. Hu, T. Feng, W.-L. Li, H. Zhai, Y. Liu, L.-Y. Wang, C.-L. Hu, M.-X. Xie, Surface molecularly imprinted polymers with synthetic dummy template for simultaneously selective recognition of nine phthalate esters, Journal of Chromatography A, 1330 (2014) 6-13).

Example 10—Evaluation of the Performance of MIPS: Regeneration and Reusability of MIP The reusability is one of the key factors in novel sorbent applications and is favored by green analytical chemistry (GAC).

To show the reusability of CAP imprinted sol-gel MIP adsorbents, the adsorption-desorption cycle of CAP was repeated several times consecutively by using the same sorbent. No substantial decrease in the adsorption capacity of sol-gel MIP was observed up to six repeated usage, while a 12.5% reduction was found after the 7th cycle of consecutive use.

Example 11—Evaluation of the Performance of MIPS: Optimization of Adsorption-Desorption Studies Studies were carried out to investigate the influence of different parameters on the retention and desorption of CAP from MIP sorbent.
Effect of Type, Volume and Flow Rate on the Elution of CAP from MIP Extraction columns using sol-gel-MIP and sol-gel NIP sorbents were prepared by packing the dried sol-gel MIP particles (30 mg) in 5 mL empty syringe barrels. Each barrel was attached with a stop cock and two frits were placed to the bottom and the top end of the MIP packed particles. The fits were obtained from commercial SPE cartridges. The MISPE columns were conditioned with 2 mL methanol and 2 mL of DI water, respectively, before loading the samples.

After loading, the samples were allowed to stay for 15 min before passing through the syringe barrel. Sample holding time was optimized after checking the extraction results by using 5 min, 10 min, 15 min, and 20 min of holding time, respectively.

The effect of the nature of eluent solvent was studied for the desorption of CAP from MIP sorbent. Elution of CAP was performed using seven different eluent systems including: acetonitrile, acetone, ethanol, methanol, 2-propanol, MeOH-ACN at v/v=1:1, and 10% formic acid.

Figure 6:
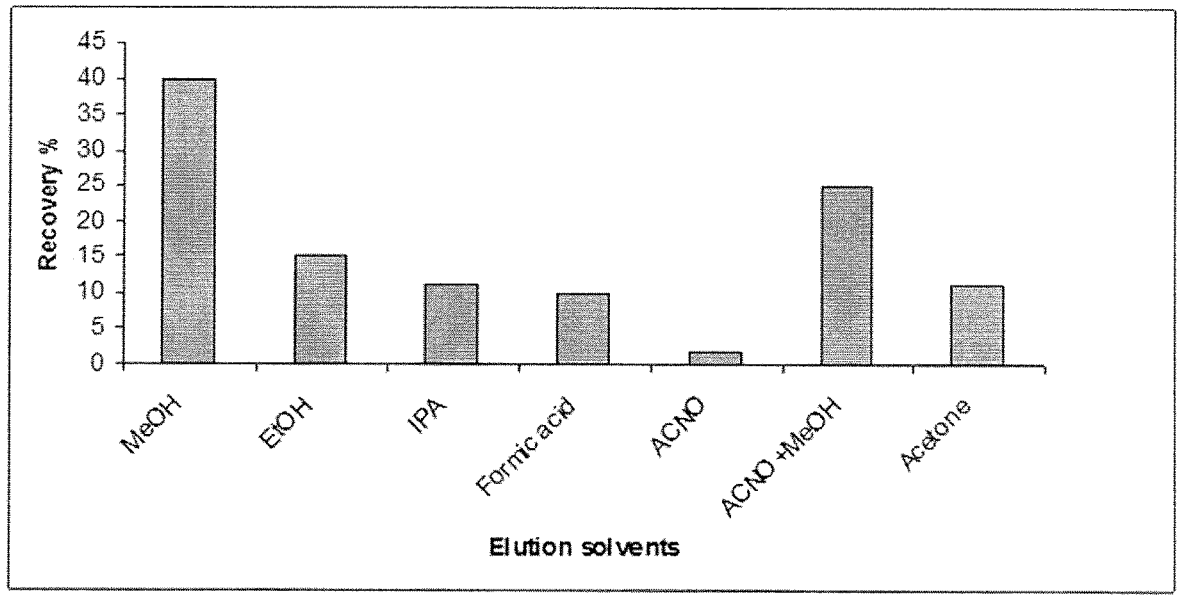
FIG. 6 shows the effect of different elution solvents on the percentage recovery of CAP from its sol-gel MIP.

As shown in FIG. 6, the use of MeOH yielded the highest percentage of recovery. In all solvents examined, the binding of CAP to the MIP was significantly higher than to the NIP, confirming the higher affinity of the imprinted polymer towards CAP.

Flow rate of sample solution and eluent solvent (0.5-2 mL/min) as well as the eluent volume (0.5-2 mL) were studied. The optimum volume of the eluent was 500 μL of methanol at a flow rate of 1 mL/min.

Figure 7:
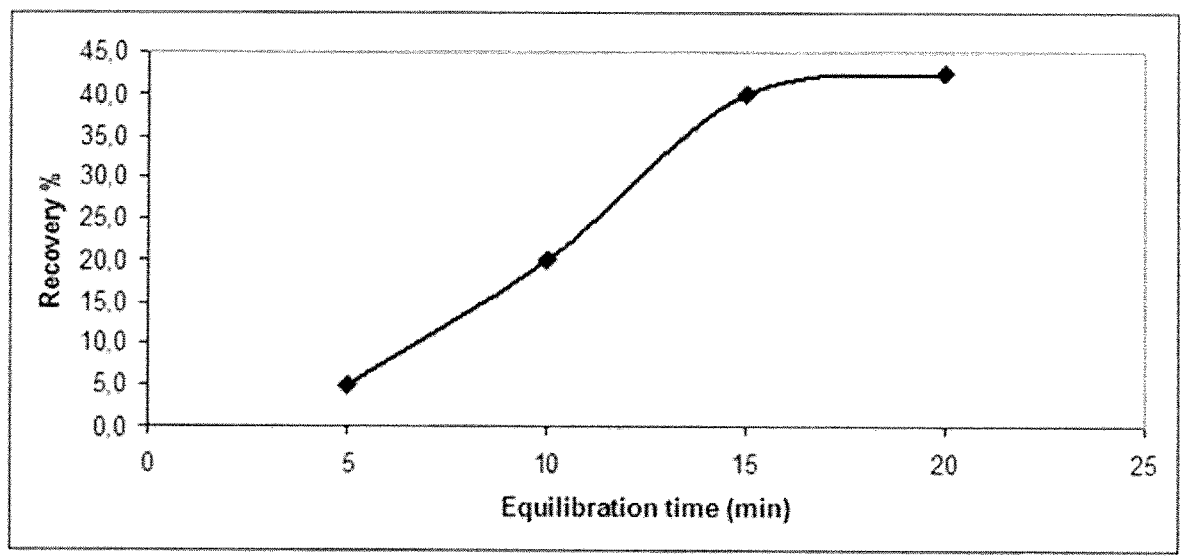
FIG. 7 shows the adsorption kinetic of CAP on the MIPSPE sorbent material.

In order to study the effect of sample volume, aliquots of 0.5 g, 2 g, 5 g, and 10 g of milk, respectively, were studied. No matrix effect was observed in milk samples of up to 10 g.
Effect of Equilibrium Time Each sample was allowed to interact with the sol-gel MIP before passing through the column. Different equilibrium times, e.g., 5 min, 10 min, 15 min, and 20 min were tested and then the sample was passed at a flow rate of 1 mL/min. Fifteen minutes of equilibrium time yielded the highest extent of recovery as shown in FIG. 7.
Fat and Protein Removal from Milk Samples Prior to Solid Phase Extraction (SPE)

Since fat and proteins were expected to interfere with the binding sites and potentially deteriorate the performance of the sol-gel MIP, they were removed from each milk sample prior to being passed through the MIPSPE column.

For fat removal, milk samples were centrifuged while for protein precipitation different agents were investigated. Acetonitrile yielded the highest percentage of recovery, though formic acid gave the best IF as shown in Table 3.

Chromatograms representing extraction from blank matrices showed no interference due to the endogenous milk components, thus proving the superior selectivity of the method towards the target analyte and the absence of non-specific interactions, a common phenomenon that frequently inhibits the performance of organically synthesized MIPs.

Example 12—Method Validation and Analytical Performance

After establishing the optimal conditions for the extraction of CAP from the sol-gel MIP, the method for determining the concentration of CAP in milk samples was validated in terms of linearity, sensitivity, precision, accuracy, and applicability to real samples.
Preparation of Standard Solutions and Treatment of Milk Samples for Fat and Protein Removal Stock solution of CAP (100 mg/L) was prepared in water and, when kept at 4° C., was found stable for at least 3 months. Working standard solutions (0.05-20 ng/μL) were also prepared in water and were stable for the same period of time when refrigerated. Methanolic standard solutions of CAP were used in LC-MS analysis as the signal was seen to have been enhanced. Stock solutions of other antibiotics as well as chromatographic conditions for their analysis were prepared and analyzed following standard procedures recognized in the art (E. G. Karageorgou, V. F. Samanidou, Development and validation according to European Union Decision 2002/657/EC of an HPLC-DAD method for milk multi-residue analysis of penicillins and amphenicols based on dispersive extraction by QuEChERS in MSPD format, Journal of Separation Science. 34 (2011) 1893-1901; E. P. Tolika, V. F. Samanidou, I. N. Papadoyannis, Development and validation of an HPLC method for the determination of ten sulfonamide residues in milk according to 2002/657/EC, Journal of Separation Science, 34 (2011) 1627-1635; E. G. Karageorgou, V. F. Samanidou, I. N. Papadoyannis, Ultrasound-assisted matrix solid phase dispersive extraction for the simultaneous analysis of ss-lactams (four penicillins and eight cephalosporins) in milk by high performance liquid chromatography with photodiode array detection, Journal of Separation Science, 35 (2012) 2599-2607; E. Karageorgou, A. Myridakis, E. G. Stephanou, V. Samanidou, Multiresidue LC-MS/MS analysis of cephalosporins and quinolones in milk following ultrasound-assisted matrix solid-phase dispersive extraction combined with the quick, easy, cheap, effective, rugged, and safe methodology, Journal of Separation Science, 36 (2013) 2020-2027; E. Karageorgou, M. Armeni, I. Moschou, V. Samanidou, Ultrasound-assisted dispersive extraction for the high pressure liquid chromatographic determination of tetracyclines residues in milk with diode array detection, Food Chemistry, 150 (2014) 328-334).

All milk samples were initially tested as blanks to confirm that no CAP was present in the samples. Milk samples (containing 3.5% or 1.5% fat) were spiked with CAP, equilibrated at room temperature for 1 hour and then centrifuged at 1900 g for 15 min. The cream layer of the milk sample was carefully removed from the solution. The supernatant was collected for subsequent protein precipitation. For skim milk, no fat removal exercise was applied prior to protein precipitation.

A 5.0 g aliquot of skim milk and 8 mL of acetonitrile was placed in a 15 mL test tube to promote protein precipitation. The mixture was vortexed for 5 min and then allowed to stand for 10 min at room temperature. The contents were centrifuged at 1900 g for 15 min and the supernatant was collected and subsequently loaded on SPE cartridges comprising the sol-gel MIP or the sol-gel NIP as provided herein.

In order to adopt the most efficient protein precipitation strategy, different protein precipitation agents were evaluated including, for example, acetonitrile, formic acid (25%), and acetic acid (25%). Imprinting factors and extraction recovery values were checked comparatively. Acetonitrile was chosen for further experiments.

Calibration curves based on peak area versus concentration were constructed from five calibration levels. Samples were prepared by spiking blank milk sample matrix with CAP corresponding to concentrations of 50-5000 μg/kg. Lower concentrations (0.1-50 μg/kg) were analysed by LC-MS.

Repeatability, intermediate precision, and accuracy assays were performed at three concentration levels (100, 200 and 300 μg/kg). Blank milk samples were spiked with CAP and the recovery of CAP was calculated using the calibration curves. Five measurements were used for within-day repeatability assay. Intermediate reproducibility (between-day) was studied in a period of three days, by triplicate analysis. Recovery of CAP was calculated using the calibration curves.

Limits of detection and quantitation were based on the S/N ratio. The CCα and CCβ were calculated from ten blank milk samples quantified against the calibration curve from the linearity testing (T. E. Commission, Commission Decision (EU) 657/2002, L 221/8, of 12 Aug. 2002, implementing Council Directive 96/23/EC concerning the performance of analytical methods and the interpretation of results, (notified under document number C (2002) 3044), Official Journal of the European Communities, L 221 (2002) 8-36).

As for the applicability to real samples, five samples of three different types of milk samples, e.g., full-fat (3.5% fat) milk, semi-skim milk (1.5% fat), and skim (0% fat), were analysed using the MIPSPE method developed herein.

The analytical features of the synthesis methods provided herein such as linear range of the calibration curve, limit of detection (LOD), and precision were also examined. The calibration graph was linear in the range of 0.5-20 ng/mL of chloramphenicol. The equation for the calibration curve was: $y=0.0396x+0.0048$, $R^2=0.9981$ for standard solutions ($x=ng/\mu L$) and $y=9.8\times10.6x+0.00472$, $R^2=0.9926$ for milk ($x=\mu g/kg$).

The LOD was calculated based on 3 times the signal-to-noise (S/N) ratio and the limit of quantitation (LOQ) was calculated as 10 times the S/N ratio.

Figure 8A:
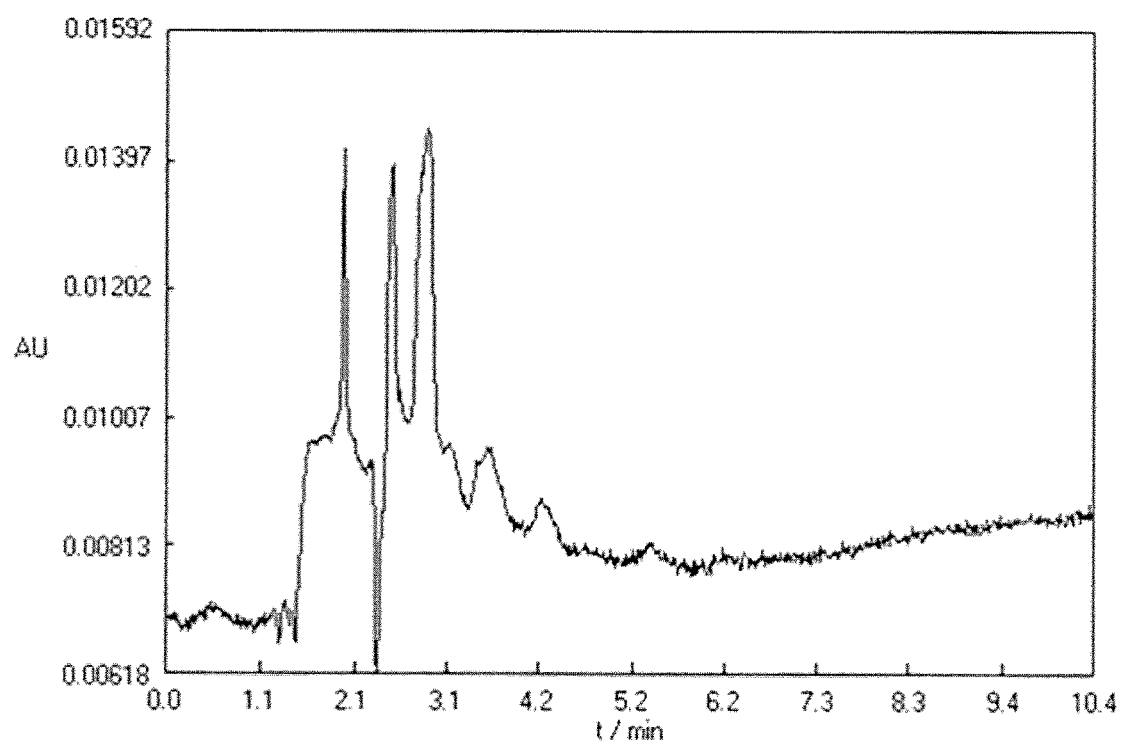
FIGS. 8A-8B illustrate chromatogram of (8A) a blank sample and (8B) a spiked milk sample obtained using the HPLC-UV method.
Figure 8B:
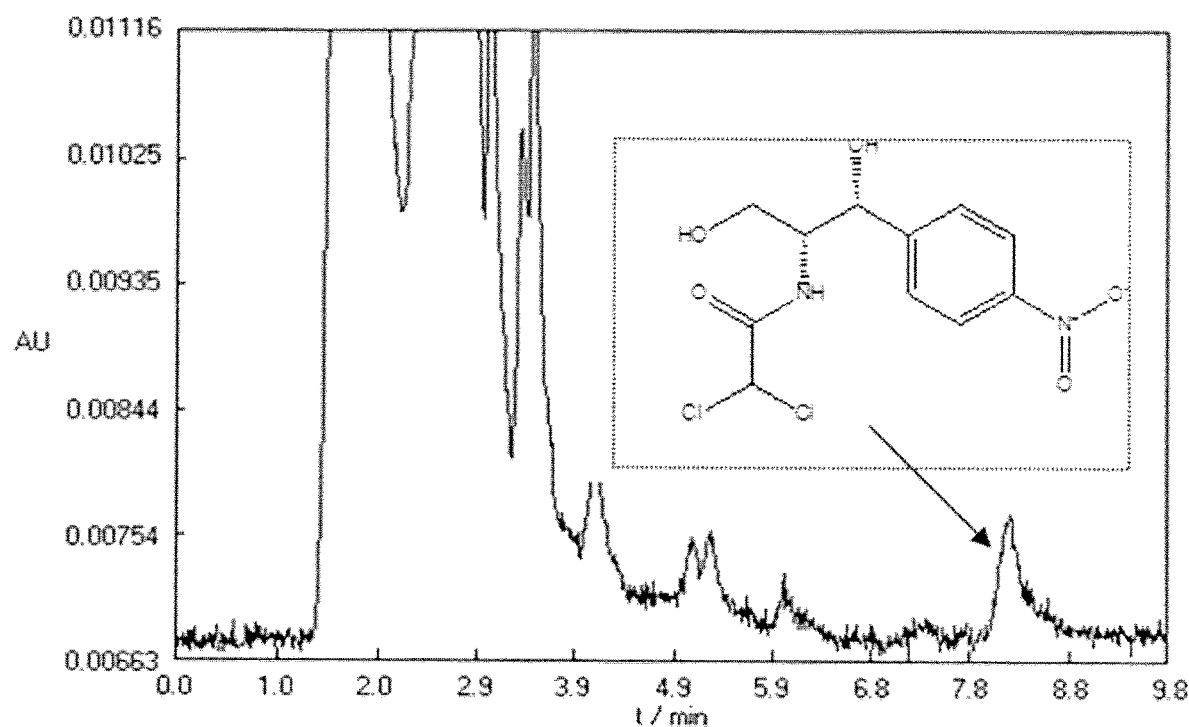
Figure 9A:
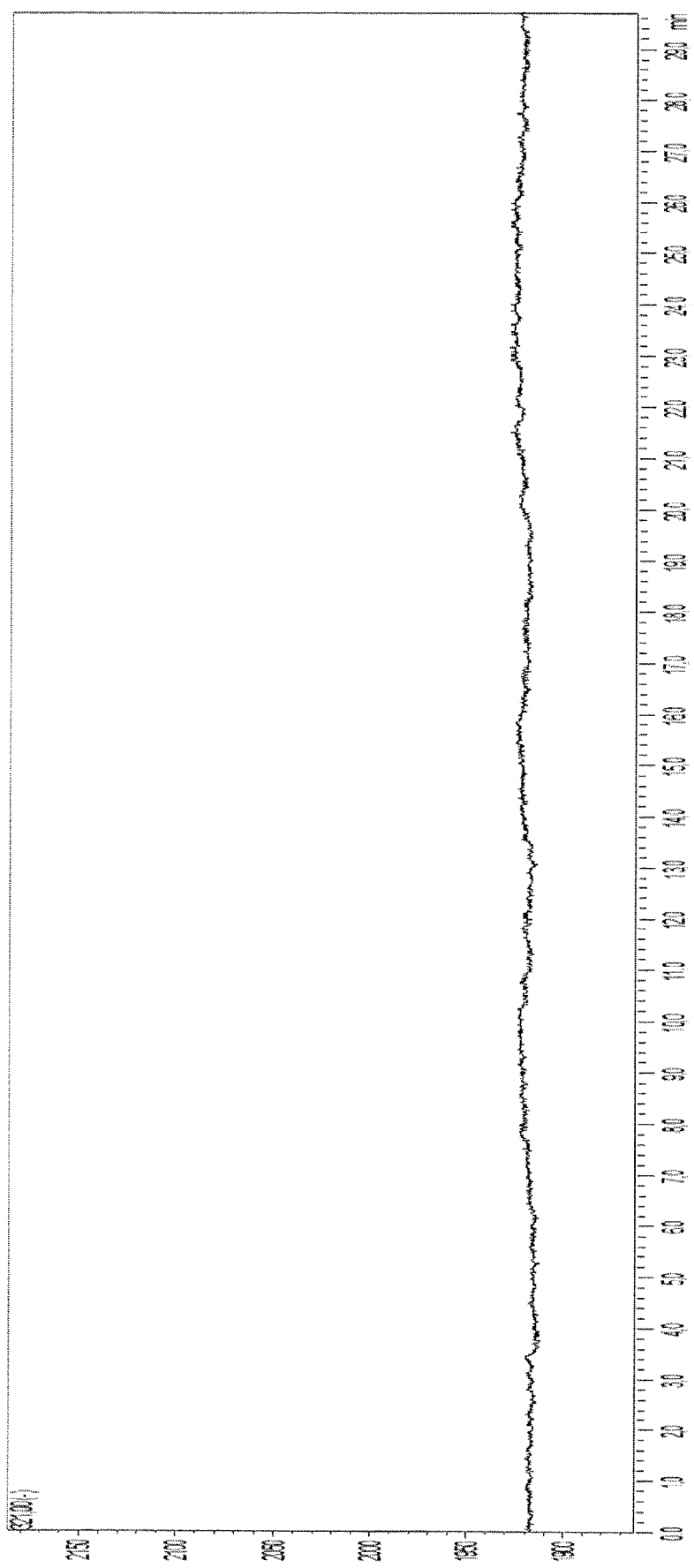
FIGS. 9A-9D illustrate LC-MS chromatogram of (9A) a blank sample, (9B) a spiked milk sample at 50 µg/kg (9C) an SIM spectrum, and (9D) a full-scan spectrum, respectively.
Figure 9B:
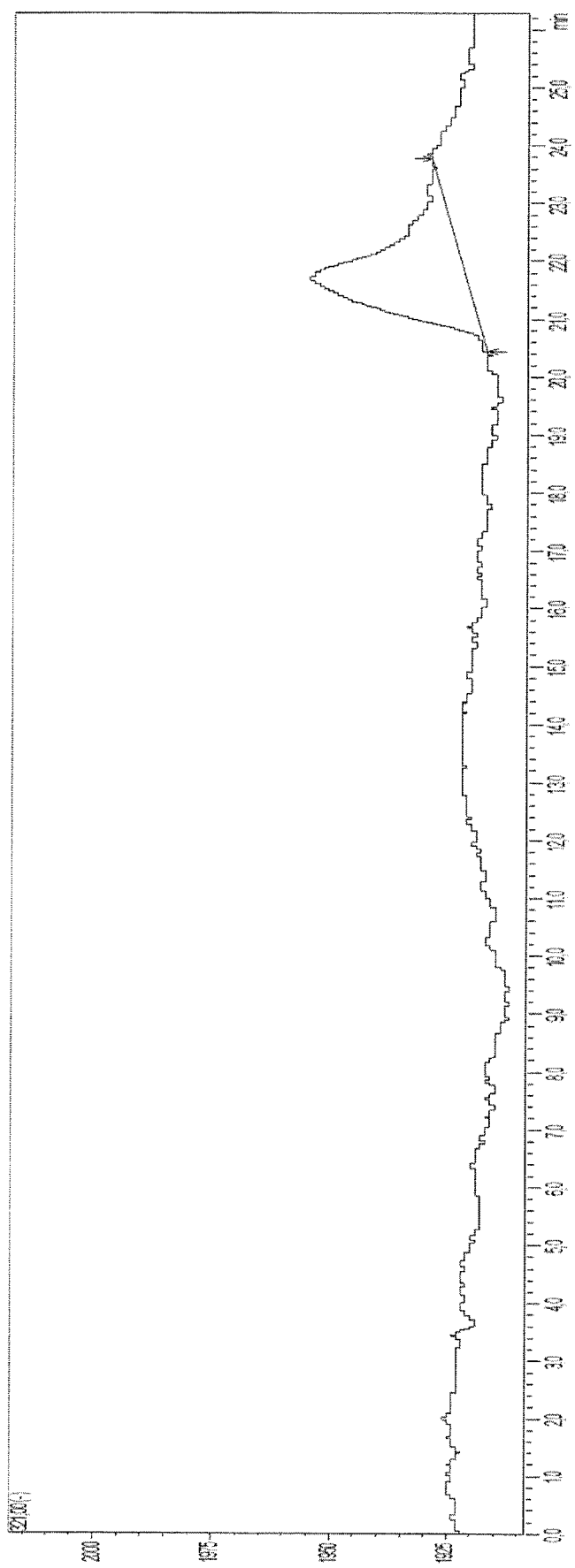
Figure 9C:
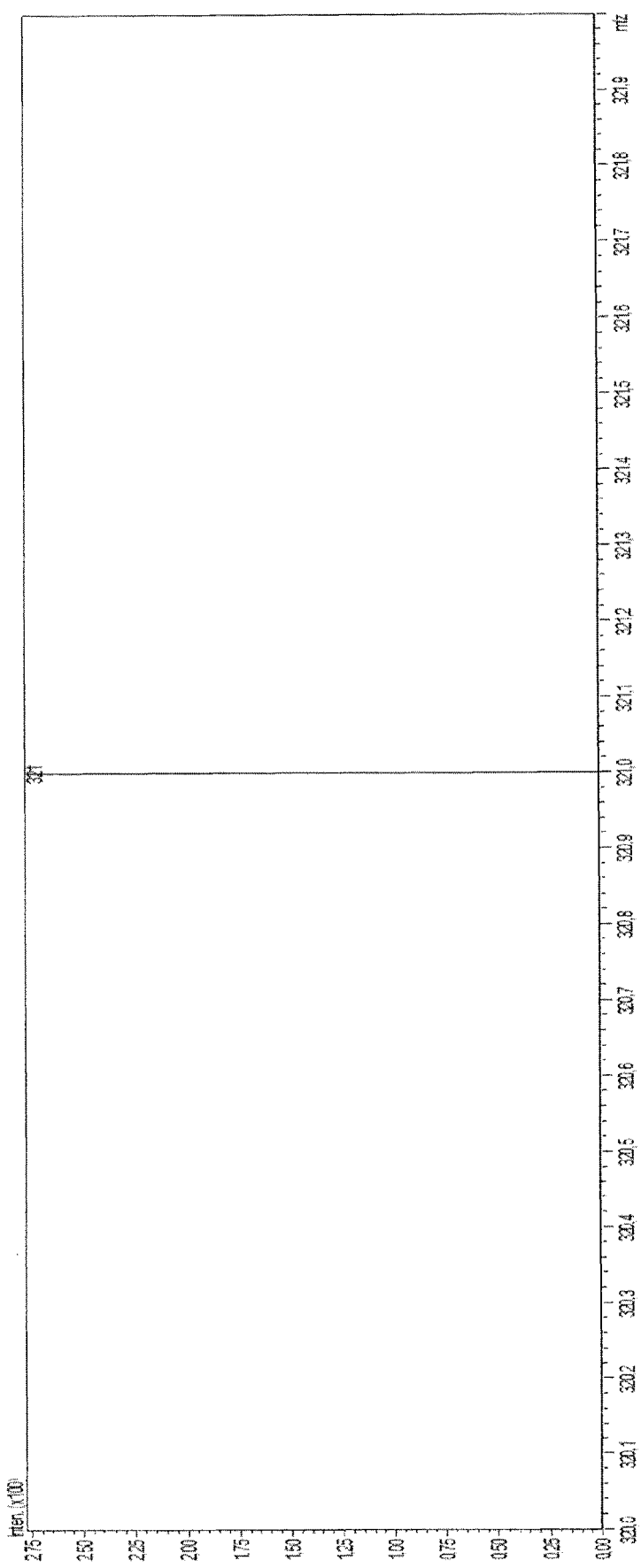
Figure 9D:
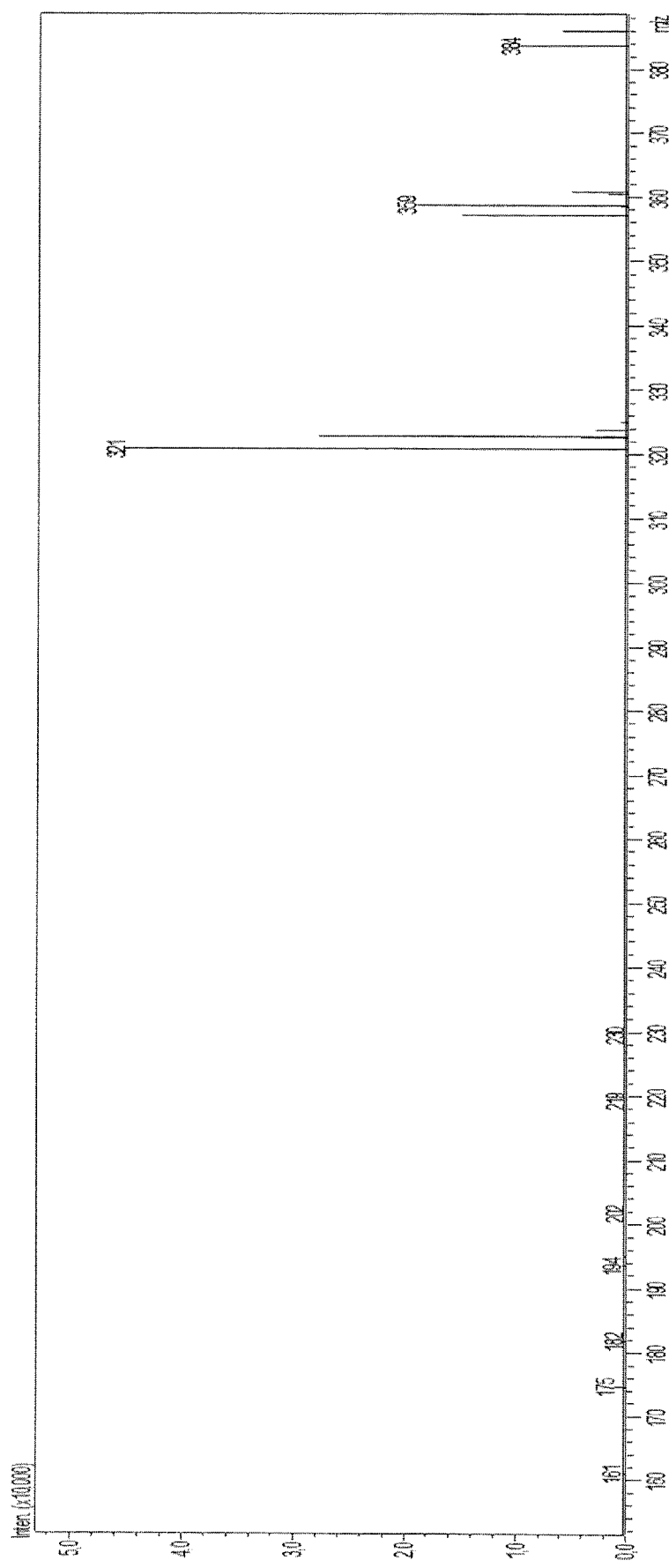

FIGS. 8A-8B illustrate a blank and a spiked milk chromatogram, respectively, obtained by the HPLC-UV method. Since CAP is an illicit substance, there is no maximum required level (MRL). The maximum required performance level (MRPL) of CAP, on the other hand, is 0.3 μg/kg, which can be reached only by using the LC-MS method (FIGS. 9A and 9B).

Decision Limit CCα and Detection Capacity CC/3 Values were Determined

Repeatability, intermediate precision, and accuracy of the synthesis methods provided herein were examined at three levels, namely, at 100 μg/kg, 200 μg/kg, and 300 μg/kg. The relative standard deviation (RSD) of the within-day and between-day assays was lower than 11% and 13% respectively, showing good precision.

Accuracy was calculated by relative recovery and found to be in the range of 89-97% for within-day assay and 85-106% for between-day assay. Table 4 summarizes the analytical performance data.

TABLE 4

Validation parameters of the MISPE method for the determination of CAP in milk.

| Validation parameters | Value |
|---|---|
| Linear range μg/kg | 50-5000 |
| Linearity $R^2$ | 0.9926 |
| Slope | $9.78 \times 10^{-6}$ |
| Intercept | 0.0047 |
| LOD (LC-UV) S/N = 3.3 | 17 μg/kg |
| LOD (LC-MS) S/N = 3.3 | 0.1 μg/kg |

TABLE 4-continued

Validation parameters of the MISPE method for the determination of CAP in milk.

| Validation parameters | Value |
|---|---|
| LOQ (LC-UV) S/N = 10 | 50 μg/kg |
| LOQ (LC-MS) S/N = 10 | 0.3 μg/kg |
| Intra- assay precision n = 5 at 3 concentration levels | 89-97% |
| RSD % | <11% |
| Inter assay precision n = 3 × 3 at 3 concentration levels | 85-106% |
| RSD % | <13% |

Example 13—Performance Comparison with Other Cap-Imprinted Polymers

Considering the importance of monitoring the presence of CAP to ensure food safety, quality, and consumer protection, a large number of CAP-imprinted polymers have been developed over the last couple of years. However, all of these MIPs were prepared using organic synthesis approach and were used in different food and biological sample matrices. Table 5 reveals the important analytical figures of merits of selected MIPs used as extraction sorbent materials compared to the MIP sorbent obtained using the methods of the subject invention by sol-gel synthesis approach.

TABLE 5

Performance comparison of chloramphenicol imprinted molecularly imprinted polymers in different sample matrices.

| Sample Matrix | Analytical Instrument | Extraction Method | Imprinting Factor | Adsorption Capacity (mg/g) | Limit of Detection (ng/g) |
|---|---|---|---|---|---|
| Honey[a] | LC-MS/MS | Magnetic SPE | 1.375 | 5.53 | 0.047 |
| Urine[b] | | MISPE | N/A | N/A | 0.06 |
| Honey | | | | | 0.06 |
| Water | GC-MS | | | | 0.005 |
| Milk | | | | | 0.03 |
| Milk[c] | LC-ESI-MS/MS | MISPE | N/A | N/A | 0.06 |
| Honey[d] | LC-MS/MS | MISPE | 2.43 | N/A | 0.03 |
| Urine | | | | | 0.03 |
| Milk[e] | HPLC-UV | MISPE | 1.38 | 2.22 | |
| Honey[f] | HPLC-UV | MISPE | 2.2 | N/A | 100* |
| Milk[g] | HPLC-UV | MISPE | 9.7 | 23.0 | 7* |
| | LC-MS | | | | 1 |

References in Table 5:
[a] L. G. Chen, B. Li, Magnetic molecularly imprinted polymer extraction of chloramphenicol from honey, Food Chemistry, 141 (2013) 23-28.
[b] M. Rejtharova, L. Rejthar, Determination of chloramphenicol in urine, feed water, milk and honey samples using molecular imprinted polymer clean-up, Journal of Chromatography A, 1216 (2009) 8246-8253.
[c] R. Mohamed, J. Richoz-Payot. E. Gremaud, P. Mottier, E. Yilmaz, J. C. Tabet, P. A. Guy, Advantages of molecularly imprinted polymers LC-ESI-MS/MS for the selective extraction and quantification of chloramphenicol in milk-based matrixes. Comparison with a classical sample preparation, Analytical Chemistry, 79 (2007) 9557-9565.
[d] B. Boyd, H. Bjork, J. Billing, O. Shimelis, S. Axelsson. M. Leonora, E. Yilmaz, Development of an improved method for trace analysis of chloramphenicol using molecularly imprinted polymers, Journal of Chromatography A, 1174 (2007) 63-71.
[e] X. Z. Shi, A. B. Wu, S. L. Zheng, R. X. Li, D. B. Zhang, Molecularly imprinted polymer microspheres for solid-phase extraction of chloramphenicol residues in foods, Journal of Chromatography B-Analytical Technologies in the Biomedical and Life Sciences, 850 (2007) 24-30.
[f] C. Schirmer, H. Meisel, Synthesis of a molecularly imprinted polymer for the selective solid-phase extraction of chloramphenicol from honey, Journal of Chromatography A, 1132 (2006) 325-328.
[g] the subject invention.
*LOD did not meet MRPL of 0.3 ng/g set forth by European Commission Decision 2003 (E. Commission. Commission Decision (EU) 181/2003, L 71/17 of 13 Mar. 2003, Amending Decision 2002/657/EC as regards the setting of minimum required performance limits (MRPLs) for certain residues in food animal origin (notified under document number C(2003) 764, Official Journal European Union, 2003, pp. 17-18).

The comparison data demonstrates the superior performance of CAP imprinted sol-gel MIP sorbent over other reported MIPs and justifies its application in food safety and quality monitoring regimes.

Example 14—Molecularly Imprinted Polymers and their Sol Solution Compositions

| Sl. | Template Name | Chemical Structure | Sol Solution Composition |
|---|---|---|---|
| 1. | Sulfamethazine | 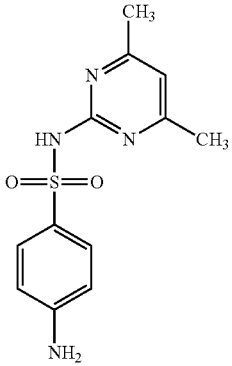 [SMILES: Cc1cc(C)nc(NS(=O)(=O)c2ccc(N)cc2)n1] | A. Complexation solution:<br>Template: 0.1231 g<br>APTES: 855 μL<br>PheTES: 111 μL<br>DMSO: 930 μL<br>B. Sol solution hydrolysis:<br>TEOS: 3690 μL<br>DMSO: 16200 μL<br>TFA (0.1M): 630 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 2. | Ciprofloxacin | 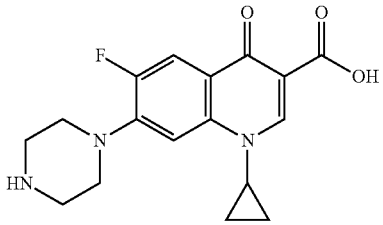 [SMILES: O=C(O)c1cn(C2CC2)c2cc(N3CCNCC3)c(F)cc2c1=O] | A. Complexation solution:<br>Template: 0.1011 g<br>APTES: 637 μL<br>PheTES: 147 μL<br>Isopropanol: 120 μL<br>B. Sol solution hydrolysis:<br>TMOS: 2065 μL<br>Isopropanol: 15740 μL<br>TFA (0.1M): 1035 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 3. | Sulfamerazine | 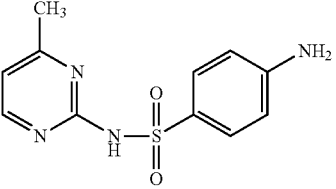 [SMILES: Cc1ccnc(NS(=O)(=O)c2ccc(N)cc2)n1] | A. Complexation solution:<br>Template: 0.1011 g<br>APTES: 637 μL<br>PheTES: 147 μL<br>Isopropanol: 120 μL<br>B. Sol solution hydrolysis:<br>TMOS: 2065 μL<br>Isopropanol: 15740 μL<br>TFA (0.1M): 1035 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

-continued

| Sl. | Template Name | Chemical Structure | Sol Solution Composition |
|---|---|---|---|
| 4. | Mangiferin | 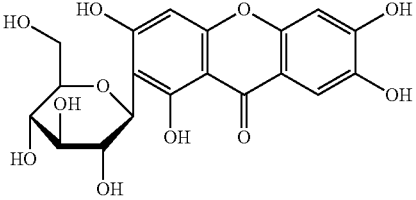 | A. Complexation solution:<br>Template: 0.120 g<br>3-APTES: 1272 μL<br>PheTES: 140 μL<br>DMSO: 6000 μL<br>B. Sol solution hydrolysis:<br>TEOS: 4400 μL<br>HCl (0.1M): 2040 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 5. | 2-Chlorophenol | 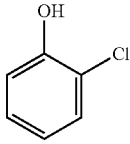 | A. Complexation solution:<br>Template: 0.2006 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 6. | Diclofenac Sodium | 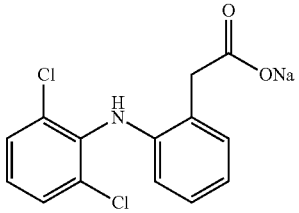 | A. Complexation solution:<br>Template: 0.1412 g<br>APTES: 340 μL<br>PheTES: 340 μL<br>Methanol: 3000 μL<br>B. Sol solution hydrolysis:<br>TEOS: 1500 μL<br>Methanol: 15740 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

| Sl. | Template Name | Chemical Structure | Sol Solution Composition |
|---|---|---|---|
| 7. | Sulfacetamide | [structure of sulfacetamide] | A. Complexation solution:<br>Template: 0.4011 g<br>3-APTES: 2850 μL<br>PheTES: 370 μL<br>DMSO: 3100 μL<br>B. Sol solution hydrolysis:<br>TEOS: 4100 μL<br>DMSO: 18000 μL<br>TFA (0.1M): 700 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 8. | 2,4-Dichlorophenol | [structure of 2,4-dichlorophenol] | A. Complexation solution:<br>Template: 0.2006 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 9. | Progesterone | [structure of progesterone] | A. Complexation solution:<br>Template: 0.2238 g<br>APTES: 340 μL<br>PheTES: 0 μL<br>Methanol: 3000 μL<br>B. Sol solution hydrolysis:<br>TEOS: 1500 μL<br>Methanol: 3000 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

| Sl. | Template Name | Chemical Structure | Sol Solution Composition |
|---|---|---|---|
| 10. | Pyrene | 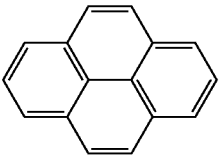 [SMILES: c1cc2ccc3cccc4ccc(c1)c2c34] | A. Complexation solution:<br>Template: 0.12788 g<br>PheTES: 480 μL<br>Isopropanol: 5000 μL<br>B. Sol solution hydrolysis:<br>TMOS: 1500 μL<br>Isopropanol: 6140 μL<br>HCl (0.1M): 750 μL<br>Gelation:<br>Both A and B solutions were incubated for 12 h followed by adding together.<br>Added NH₄OH (1M): 450 μL<br>The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 11. | Fluoranthene | 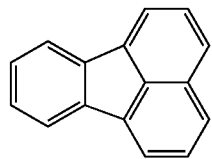 [SMILES: c1ccc2c(c1)-c1cccc3cccc-2c13] | A. Complexation solution:<br>Template: 0.1738 g<br>APTES: 0 μL<br>PheTES: 480 μL<br>2-propanol: 11400 μL<br>Tetrahydrofuran: 2000 μL<br>B. Sol solution hydrolysis:<br>TEOS: 1500 μL<br>2-propanol: 3000 μL<br>HCl (0.1M): 705 μL<br>Gelation:<br>Both A and B solutions were incubated for 12 h followed by adding together and subsequently, 450 μL of 1M NH₄OH was added to the mixture.<br>The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 12. | Bisphenol A | 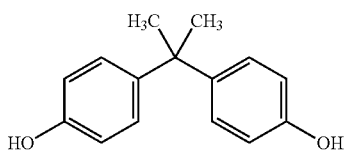 [SMILES: CC(C)(c1ccc(O)cc1)c1ccc(O)cc1] | A. Complexation solution:<br>Template: 0.075495 g<br>APTMS: 120 μL<br>PheTES: 160 μL<br>Isopropanol: 1000 μL<br>B. Sol solution hydrolysis:<br>TMOS: 500 μL<br>Isopropanol: 3000 μL<br>TFA (0.1M): 125 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

-continued

| Sl. | Template Name | Chemical Structure | Sol Solution Composition |
|---|---|---|---|
| 13. | 2-Nitrophenol | (2-nitrophenol structure: benzene ring with OH and NO₂) | A. Complexation solution:<br>Template: 0.0976 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 14. | Phenantherene | (phenanthrene structure) | A. Complexation solution:<br>Template: 0.1499 g<br>APTES: 0 μL<br>PheTES: 480 μL<br>2-propanol: 5700 μL<br>B. Sol solution hydrolysis:<br>TEOS: 1500 μL<br>2-propanol: 3000 μL<br>HCl (0.1M): 705 μL<br>Gelation:<br>Both A and B solutions were incubated for 12 h followed by adding together and subsequently, 450 μL of 1M NH₄OH was added to the mixture. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 15. | Nonylphenol | (nonylphenol structure: $C_9H_{19}$-phenyl-OH) | A. Complexation solution:<br>Template: 0.1520 g<br>APTES: 340 μL<br>PheTES: 180 μL<br>DMSO: 2000 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

| Sl. | Template Name | Chemical Structure | Sol Solution Composition |
|---|---|---|---|
| 16. | Ketoprofen | 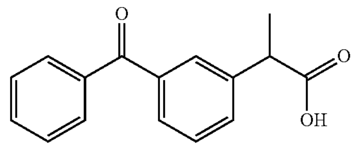 [SMILES: CC(C(=O)O)c1cccc(C(=O)c2ccccc2)c1] | A. Complexation solution:<br>Template: 0.1807 g<br>APTES: 340 μL<br>PheTES: 340 μL<br>Acetone: 5315 μL<br>B. Sol solution hydrolysis:<br>TEOS: 1500 μL<br>Acetone: 5315 μL<br>HCl (0.1M): 520 μL<br>Gelation:<br>Both A and B solutions were<br>incubated for 12 h followed by adding<br>together. The mixture form solid gel.<br>Processing the gel:<br>The gel was heated at 50° C. for 48 h<br>for completing the gelation process.<br>The gel was then dried in a vacuum<br>oven for 24 h at 80° C. The particles<br>are then crushed, ground and screened<br>to obtain particle size of 20-50 μm.<br>Finally, the templates removed using a<br>Soxhlet Extraction Unit/Accelerated<br>Solvent Extraction System. |
| 17. | Acetaminophen | 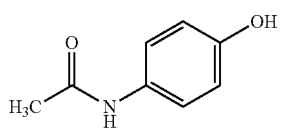 | C. Complexation solution:<br>Template: 0.1001 g<br>APTES: 620 μL<br>PheTES: 800 μL<br>Isopropanol: 5100 μL<br>D. Sol solution hydrolysis:<br>TMOS: 2010 μL<br>Isopropanol: 15300 μL<br>TFA (0.1M): 950 μL<br>Gelation:<br>Both A and B solutions were<br>incubated for 12 h followed by adding<br>together. The mixture form solid gel.<br>Processing the gel:<br>The gel was heated at 50° C. for 48 h<br>for completing the gelation process.<br>The gel was then dried in a vacuum<br>oven for 24 h at 80° C. The particles<br>are then crushed, ground and screened<br>to obtain particle size of 20-50 μm.<br>Finally, the templates removed using a<br>Soxhlet Extraction Unit/Accelerated<br>Solvent Extraction System. |
| 18. | Antipyrine | 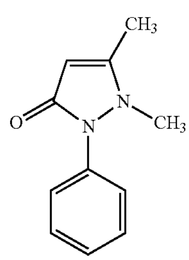 | A. Complexation solution:<br>Template: 0.2729 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were<br>incubated for 12 h followed by adding<br>together. The mixture form solid gel.<br>Processing the gel:<br>The gel was heated at 50° C. for 48 h<br>for completing the gelation process.<br>The gel was then dried in a vacuum<br>oven for 24 h at 80° C. The particles<br>are then crushed, ground and screened<br>to obtain particle size of 20-50 μm.<br>Finally, the templates removed using a<br>Soxhlet Extraction Unit/Accelerated<br>Solvent Extraction System. |

-continued

| Sl. | Template Name | Chemical Structure | Sol Solution Composition |
|---|---|---|---|
| 19. | Estrone | 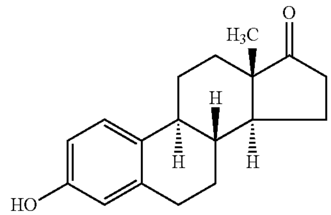 | A. Complexation solution:<br>Template: 0.2534 g<br>APTES: 340 µL<br>PheTES: 100 µL<br>DMSO: 5150 µL<br>B. Sol solution hydrolysis:<br>TEOS: 1500 µL<br>DMSO: 5150 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 20. | Naphthalene | 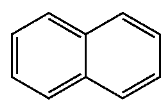 | A. Complexation solution:<br>Template: 0.1635 g<br>PheTES: 480 µL<br>Isopropanol: 5000 µL<br>B. Sol solution hydrolysis:<br>TMOS: 1500 µL<br>Isopropanol: 6140 µL<br>HCl (0.1M): 750 µL<br>Gelation:<br>Both A and B solutions were incubated for 12 h followed by adding together.<br>Added NH$_4$OH (1M): 450 µL<br>The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 21. | Trans-Androsterone | 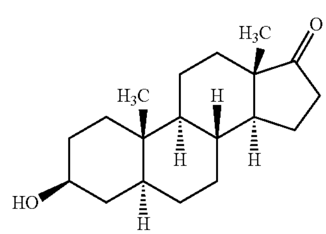 | A. Complexation solution:<br>Template: 0.3211 g<br>APTES: 340 µL<br>PheTES: 0 µL<br>Methanol: 3000 µL<br>B. Sol solution hydrolysis:<br>TEOS: 1500 µL<br>Methanol: 3000 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |

| Sl. | Template Name | Chemical Structure | Sol Solution Composition |
|---|---|---|---|
| 22. | 4-Nitrophenol | $O_2N$-C$_6$H$_4$-OH | A. Complexation solution:<br>Template: 0.1007 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 23. | Hexestrol | (structure of hexestrol) | A. Complexation solution:<br>Template: 0.1929 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 24. | Gemfibrozil | (structure of gemfibrozil) | A. Complexation solution:<br>Template: 0.1779 g<br>APTES: 340 μL<br>PheTES: 180 μL<br>Methanol: 3000 μL<br>B. Sol solution hydrolysis:<br>TEOS: 1500 μL<br>Methanol: 3000 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

| Sl. | Template Name | Chemical Structure | Sol Solution Composition |
|---|---|---|---|
| 25. | Estradiol | 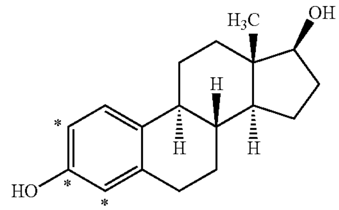 | A. Complexation solution:<br>Template: 0.1948 g<br>APTES: 340 μL<br>PheTES: 180 μL<br>Ethanol: 3500 μL<br>B. Sol solution hydrolysis:<br>TEOS: 1500 μL<br>Ethanol: 3500 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 26. | Diethylstilbestrol | 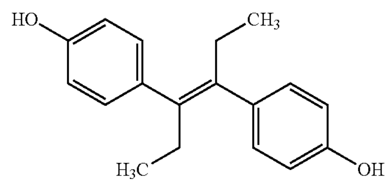 [SMILES: CC/C(=C(/CC)c1ccc(O)cc1)c1ccc(O)cc1] | A. Complexation solution:<br>Template: 0.1899 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 510 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 27. | Fluorene | 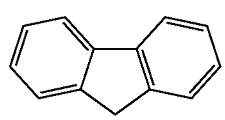 [SMILES: c1ccc2c(c1)Cc1ccccc1-2] | A. Complexation solution:<br>Template: 0.2089 g<br>PheTES: 480 μL<br>Isopropanol: 5000 μL<br>B. Sol solution hydrolysis:<br>TMOS: 1500 μL<br>Isopropanol: 6140 μL<br>HCl (0.1M): 705 μL<br>Gelation:<br>Both A and B solutions were incubated for 12 h followed by adding together.<br>Added NH$_4$OH (1M): 450 μL<br>The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

-continued

| Sl. | Template Name | Chemical Structure | Sol Solution Composition |
|---|---|---|---|
| 28. | Ibuprofen | (structure of ibuprofen) | A. Complexation solution:<br>Template: 0.1472 g<br>APTES: 340 μL<br>PheTES: 180 μL<br>Methanol: 1900 μL<br>B. Sol solution hydrolysis:<br>TEOS: 1500 μL<br>Methanol: 3000 μL<br>HCl (0.1M): 1520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 29. | Anthracene | (structure of anthracene) | A. Complexation solution:<br>Template: 0.0839 g<br>PheTES: 350 μL<br>MeOH: 6000 μL<br>B. Sol solution hydrolysis:<br>TEOS: 1500 μL<br>MeOH: 3000 μL<br>HCl (0.1M): 520 μL<br>Gelation:<br>Both A and B solutions were incubated for 12 h followed by adding together.<br>Added NH$_4$OH (1M): 450 μL<br>The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 30. | Estriol | (structure of estriol) | A. Complexation solution:<br>Template: 0.1397 g<br>APTES: 340 μL<br>PheTES: 100 μL<br>DMSO: 5150 μL<br>B. Sol solution hydrolysis:<br>TEOS: 1500 μL<br>DMSO: 5150 μL<br>HCl (0.1M): 510 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

| Sl. | Template Name | Chemical Structure | Sol Solution Composition |
|---|---|---|---|
| 31. | 17α-Estradiol | 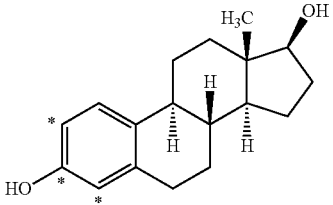 | A. Complexation solution:<br>Template: 0.0900 g<br>APTES: 340 μL<br>PheTES: 100 μL<br>DMSO: 5150 μL<br>B. Sol solution hydrolysis:<br>TEOS: 1500 μL<br>DMSO: 5150 μL<br>HCl (0.1M): 510 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 32. | Sulfadiazine | 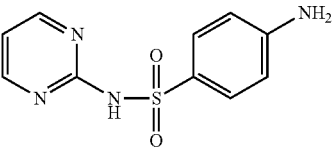 [SMILES: Nc1ccc(S(=O)(=O)Nc2ncccn2)cc1] | A. Complexation solution:<br>Template: 0.5011 g<br>3-APTMS: 2875 μL<br>PheTES: 490 μL<br>Isopropanol: 6000 μL<br>B. Sol solution hydrolysis:<br>TMOS: 3040 μL<br>Isopropanol: 18000 μL<br>TFA (0.1M): 900 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 33. | Sulfamethizole | 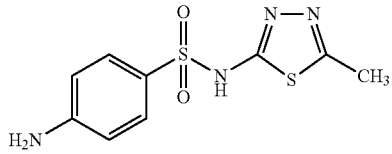 [SMILES: Cc1nnc(NS(=O)(=O)c2ccc(N)cc2)s1] | A. Complexation solution:<br>Template: 0.5022 g<br>3-APTMS: 2660 μL<br>PheTES: 450 μL<br>Isopropanol: 5700 μL<br>B. Sol solution hydrolysis:<br>TMOS: 2800 μL<br>Isopropanol: 17000 μL<br>TFA (0.1M): 840 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

| Sl. | Template Name | Chemical Structure | Sol Solution Composition |
|---|---|---|---|
| 34. | Sulfamethoxazole | 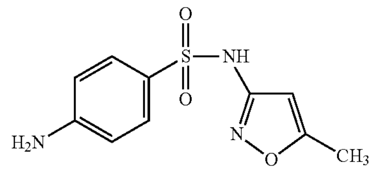 [SMILES: Cc1cc(NS(=O)(=O)c2ccc(N)cc2)no1] | A. Complexation solution:<br>Template: 0.1041 g<br>3-APEMS: 340 μL<br>PheTES: 100 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 35. | Caffeic acid | 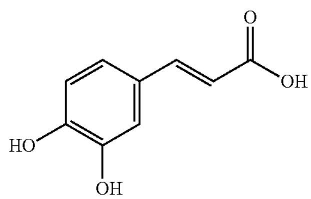 [SMILES: O=C(O)/C=C/c1ccc(O)c(O)c1] | C. Complexation solution:<br>Template: 0.0685 g<br>APTES: 340 μL<br>PheTES: 100 μL<br>DMSO: 5150 μL<br>D. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 36. | Saccharine | 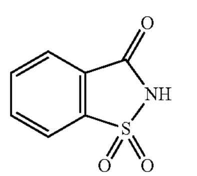 [SMILES: O=C1NS(=O)(=O)c2ccccc21] | A. Complexation solution:<br>Template: 0.1388 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 37. | Safrole | 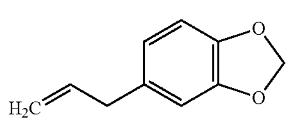 | A. Complexation solution:<br>Template: 0.116 g<br>APTES: 340 μL<br>PheTES: 350 μL<br>DMSO: 5150 μL<br>B. Sol solution hydrolysis: |

-continued

| Sl. | Template Name | Chemical Structure | Sol Solution Composition |
|---|---|---|---|
| | | | TEOS: 1500 µL<br>DMSO: 5150 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 38. | Isopropyl 4-hydroxybenzoate | 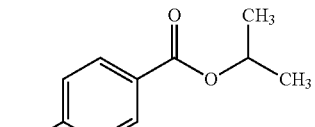 | A. Complexation solution:<br>Template: 0.1305 g<br>APTES: 340 µL<br>PheTES: 180 µL<br>DMSO: 5150 µL<br>B. Sol solution hydrolysis:<br>TEOS: 1500 µL<br>DMSO: 5150 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 39. | Butyl 4-hydroxybenzoate | 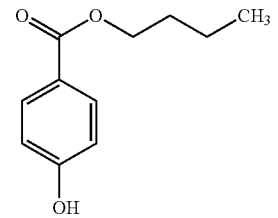 | A. Complexation solution:<br>Template: 0.139 g<br>APTES: 340 µL<br>PheTES: 180 µL<br>DMSO: 5150 µL<br>B. Sol solution hydrolysis:<br>TEOS: 1500 µL<br>DMSO: 5150 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 40. | Benzotriazole | 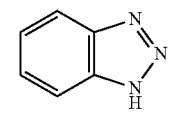 | A. Complexation solution:<br>Template: 0.085 g<br>APTES: 340 µL<br>PheTES: 180 µL<br>DMSO: 5150 µL<br>B. Sol solution hydrolysis:<br>TEOS: 1500 µL<br>DMSO: 5150 µL<br>HCl (0.1M): 520 µL<br>Gelation:<br>Both A and B solutions were incubated for 12 h followed by adding |

| Sl. | Template Name | Chemical Structure | Sol Solution Composition |
|---|---|---|---|
| | | | together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 41. | 2-Methyl-4,6-dinitrophenol (DNOC) | 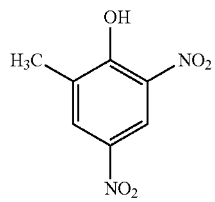 | A. Complexation solution: Template: 0.203 g APTES: 340 μL PheTES: 350 μL DMSO: 5150 μL B. Sol solution hydrolysis: TEOS: 1500 μL DMSO: 5150 μL HCl (0.1M): 520 μL Gelation: Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| | Phenol | | A. Complexation solution: Template: 0.1301 g APTES: 340 μL PheTES: 350 μL DMSO: 5150 μL B. Sol solution hydrolysis: TEOS: 1500 μL DMSO: 5150 μL HCl (0.1M): 520 μL Gelation: Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 42. | Ethyl 4-hydroxybenzoate | 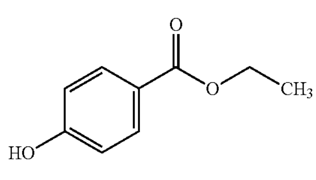 | A. Complexation solution: Template: 0.1202 g APTES: 340 μL PheTES: 180 μL DMSO: 5150 μL B. Sol solution hydrolysis: TEOS: 1500 μL DMSO: 5150 μL HCl (0.1M): 520 μL Gelation: Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles |

| Sl. | Template Name | Chemical Structure | Sol Solution Composition |
|---|---|---|---|
| | | | are then crushed, ground and screened to obtain particle size of 20-50 μm. Finally, the templates removed using a Soxhlet Extraction Unit/Accelerated Solvent Extraction System. |
| 43. | Nitrobenzene | 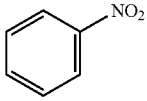 | A. Complexation solution:<br>Template: 0.1855 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 44. | Triclosan | 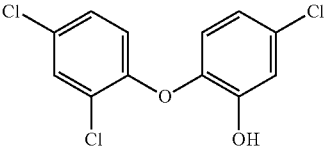 [SMILES: Oc1cc(Cl)ccc1Oc1ccc(Cl)cc1Cl] | A. Complexation solution:<br>Template: 0.4130 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 45. | Pentachlorophenol | 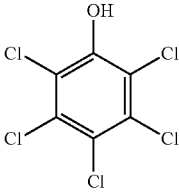 [SMILES: Oc1c(Cl)c(Cl)c(Cl)c(Cl)c1Cl] | A. Complexation solution:<br>Template: 0.3813 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

-continued

| Sl. | Template Name | Chemical Structure | Sol Solution Composition |
|---|---|---|---|
| 46. | Ciprofloxacin | 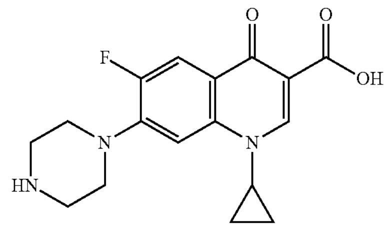 [SMILES: O=C(O)c1cn(C2CC2)c2cc(N3CCNCC3)c(F)cc2c1=O] | A. Complexation solution:<br>Template: 0.0963 g<br>APTES: 340 μL<br>PheTES: 140 μL<br>Acetone: 5315 μL<br>B. Sol solution hydrolysis:<br>TEOS: 1500 μL<br>Acetone: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 47. | 2,4,6-Trichlorophenol | 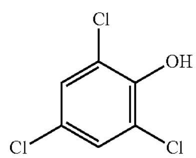 | A. Complexation solution:<br>Template: 0.2827 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 48. | Neohespirin | 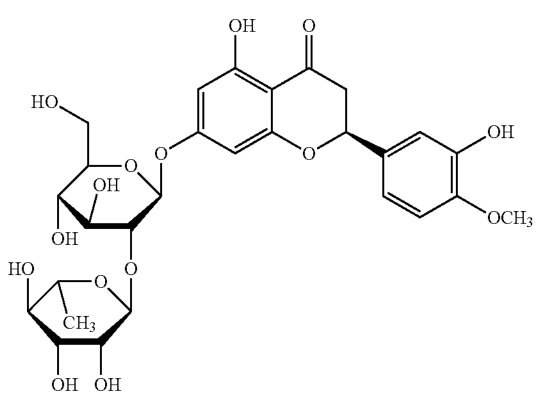 | A. Complexation solution:<br>Template: 0.0757 g<br>APTES: 340 μL<br>PheTES: 60 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

-continued

| Sl. | Template Name | Chemical Structure | Sol Solution Composition |
|---|---|---|---|
| 49. | Isobutyl 4-hydroxybenzoate | 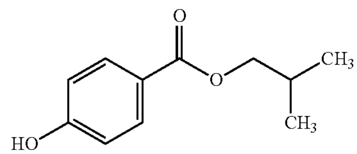 | A. Complexation solution:<br>Template: 0.139 g<br>APTES: 340 μL<br>PheTES: 180 μL<br>DMSO: 5150 μL<br>B. Sol solution hydrolysis:<br>TMOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 50. | Triclocarban | 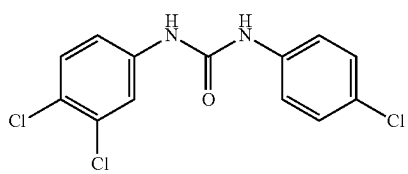 [SMILES: O=C(Nc1ccc(Cl)cc1)Nc1ccc(Cl)c(Cl)c1] | A. Complexation solution:<br>Template: 0.2263 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 51. | Methyl 4-hydroxybenzoate | 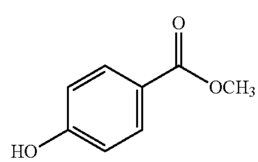 [SMILES: COC(=O)c1ccc(O)cc1] | A. Complexation solution:<br>Template: 0.1080 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

| Sl. | Template Name | Chemical Structure | Sol Solution Composition |
|---|---|---|---|
| 52. | 2,4-Dinitrotoluene | 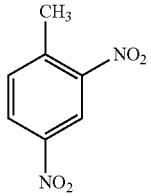 | A. Complexation solution:<br>Template: 0.1330 g<br>APTES: 340 µL<br>PheTES: 180 µL<br>DMSO: 5150 µL<br>B. Sol solution hydrolysis:<br>TEOS: 1500 µL<br>DMSO: 5150 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 53. | Acenaphthylene | 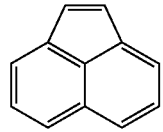 [SMILES: C1=Cc2cccc3cccc1c23] | A. Complexation solution:<br>Template: 0.1945 g<br>PheTES: 480 µL<br>Isopropanol: 5000 µL<br>B. Sol solution hydrolysis:<br>TMOS: 1500 µL<br>Isopropanol: 6140 µL<br>HCl (0.1M): 705 µL<br>Gelation:<br>Both A and B solutions were incubated for 12 h followed by adding together.<br>Added $NH_4OH$ (1M): 450 µL<br>The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 54. | Benzophenone-1 | 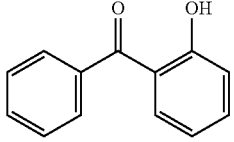 [SMILES: O=C(c1ccccc1)c1ccccc1O] | A. Complexation solution:<br>Template: 0.1022 g<br>APTES: 340 µL<br>PheTES: 240 µL<br>DMSO: 5150 µL<br>B. Sol solution hydrolysis:<br>TEOS: 1500 µL<br>DMSO: 5150 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |

| Sl. | Template Name | Chemical Structure | Sol Solution Composition |
|---|---|---|---|
| 55. | BP-2 | (2,2',4,4'-tetrahydroxybenzophenone structure) | A. Complexation solution:<br>Template: 0.070 g<br>APTES: 340 μL<br>PheTES: 140 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 56. | Sulfapyridine | (sulfapyridine structure) | A. Complexation solution:<br>Template: 0.4021 g<br>3-APTES: 2850 μL<br>PheTES: 370 μL<br>DMSO: 3100 μL<br>B. Sol solution hydrolysis:<br>TEOS: 4100 μL<br>DMSO: 18000 μL<br>TFA (0.1M): 700 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 57. | Sucrose | (sucrose structure) | A. Complexation solution:<br>Template: 0.0526 g<br>APTES: 340 μL<br>PheTES: 0 μL<br>DMSO: 5150 μL<br>B. Sol solution hydrolysis:<br>TEOS: 1500 μL<br>DMSO: 5150 μL<br>HCl (0.1M): 510 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 58. | SLC-011 | | A. Complexation solution:<br>Template: 0.2704 g<br>3-APTES: 1190 μL<br>PheTES: 630 μL<br>DMSO: 11025 μL<br>B. Sol solution hydrolysis: |

| Sl. | Template Name | Chemical Structure | Sol Solution Composition |
|---|---|---|---|
| | | | TEOS: 5250 µL<br>DMSO: 18025 µL<br>HCl (0.1M): 1820 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 59. | Butylated hydroxytoluene | 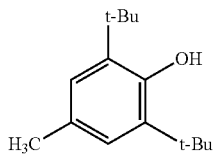 | A. Complexation solution:<br>Template: 0.4001 g<br>3-APTES: 850 µL<br>PheTES: 440 µL<br>Isopropanol: 2800 µL<br>B. Sol solution hydrolysis:<br>TEOS: 3810 µL<br>Isopropanol: 18000 µL<br>HCl (0.1M): 1700 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 60. | Butylhydroxianisole | 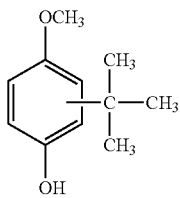 | A. Complexation solution:<br>Template: 0.4001 g<br>3-APTES: 1560 µL<br>PheTES: 540 µL<br>Isopropanol: 3400 µL<br>B. Sol solution hydrolysis:<br>TEOS: 4100 µL<br>Isopropanol: 22000 µL<br>HCl (0.1M): 2236 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 61. | Naproxen | 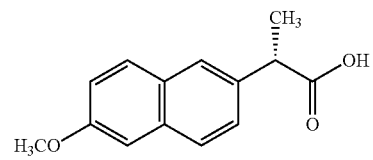 [SMILES: COc1ccc2cc([C@H](C)C(=O)O)ccc2c1] | A. Complexation solution:<br>Template: 0.1642 g<br>APTES: 340 µL<br>PheTES: 340 µL<br>DMSO: 5150 µL<br>B. Sol solution hydrolysis:<br>TEOS: 1500 µL<br>DMSO: 5150 µL<br>HCl (0.1M): 510 µL<br>Gelation:<br>Both A and B solutions were incubated for 12 h followed by adding |

| Sl. | Template Name | Chemical Structure | Sol Solution Composition |
|---|---|---|---|
| | | | together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 62. | Benzyl 4-hydroxybenzoate | 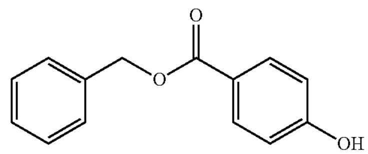 [SMILES: O=C(OCc1ccccc1)c1ccc(O)cc1] | A. Complexation solution: Template: 0.163 g APTES: 340 μL PheTES: 180 μL DMSO: 5150 μL B. Sol solution hydrolysis: TMOS: 2500 μL DMSO: 5150 μL HCl (0.1M): 520 μL Gelation: Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 63. | Chloramphenicol | 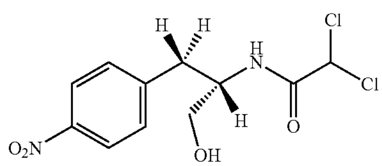 | A. Complexation solution: Template: 0.2505 g APTES: 800 μL PheTES: 800 μL Isopropanol: 5000 μL B. Sol solution hydrolysis: TMOS: 2500 μL Isopropanol: 20000 μL TFA (0.1M): 625 μL Gelation: Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 64. | D-Sorbitol | 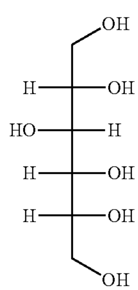 [SMILES: OCC(O)C(O)C(O)C(O)CO] | A. Complexation solution: Template: 0.043 g APTES: 340 μL PheTES: 0 μL DMSO: 5150 μL B. Sol solution hydrolysis: TMOS: 1500 μL DMSO: 5150 μL HCl (0.1M): 520 μL Gelation: Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles |

| Sl. | Template Name | Chemical Structure | Sol Solution Composition |
|---|---|---|---|
| | | | are then crushed, ground and screened to obtain particle size of 20-50 μm. Finally, the templates removed using a Soxhlet Extraction Unit/Accelerated Solvent Extraction System. |
| 65. | Sulfamethazine | 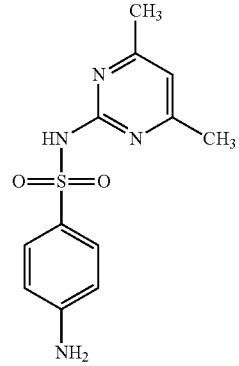 [SMILES: Cc1cc(C)nc(NS(=O)(=O)c2ccc(N)cc2)n1] | A. Complexation solution:<br>Template: 0.5032 g<br>3-APTMS: 2585 μL<br>PheTES: 440 μL<br>Isopropanol: 5550 μL<br>B. Sol solution hydrolysis:<br>TMOS: 2735 μL<br>Isopropanol: 16650 μL<br>TFA (0.1M): 810 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 66. | Sulfathiazole | 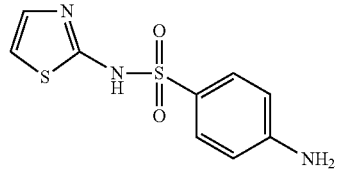 [SMILES: Nc1ccc(S(=O)(=O)Nc2nccs2)cc1] | A. Complexation solution:<br>Template: 0.5013 g<br>3-APTMS: 2815 μL<br>PheTES: 480 μL<br>Isopropanol: 6000 μL<br>B. Sol solution hydrolysis:<br>TMOS: 3000 μL<br>Isopropanol: 18000 μL<br>TFA (0.1M): 880 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 67. | Chlorogenic Acid | 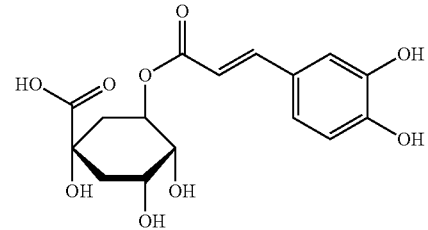 | A. Complexation solution:<br>Template: 0.1000 g<br>APTES: 990 μL<br>PheTES: 70 μL<br>Isopropanol: 1900 μL<br>B. Sol solution hydrolysis:<br>TMOS: 3210 μL<br>Isopropanol: 4900 μL<br>HCl (0.1M): 1520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |

-continued

| Sl. | Template Name | Chemical Structure | Sol Solution Composition |
|---|---|---|---|
| 68. | Caffeine | 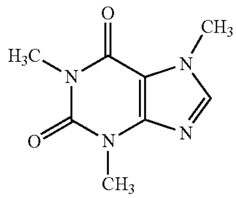 | A. Complexation solution:<br>Template: 0.1953 g<br>APTES: 340 µL<br>PheTES: 250 µL<br>DMSOl: 5150 µL<br>B. Sol solution hydrolysis:<br>TEOS: 1500 µL<br>DMSO: 5150 µL<br>HCl (0.1M): 520 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 69. | Diphenhydramine | 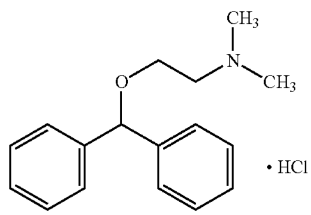 [SMILES: CN(C)CCOC(c1ccccc1)c1ccccc1 ; "· HCl"] | A. Complexation solution:<br>Template: 0.5058 g<br>APTES: 920 µL<br>PheTES: 960 µL<br>Methanol: 1600 µL<br>B. Sol solution hydrolysis:<br>TEOS: 4120 µL<br>MeOH: 10400 µL<br>Water: 1840 µL<br>TFA: 400 µL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm. Finally, the templates removed using a Soxhlet Extraction Unit/Accelerated Solvent Extraction System. |
| 70. | Six sulfa drugs<br>Sulfanilamide<br>Sulfacetamide<br>Sulfadiazine<br>Sulfathiazole<br>Sulfamerazine<br>Sulfamethizole | | A1. Complexation solution:<br>Sulfanilamide: 0.0414 g<br>APTES: 170 µL<br>PheTES: 60 µL<br>DMSO: 2575 µL<br>A2. Complexation solution:<br>Sulfacetamide: 0.0508 g<br>APTES: 170 µL<br>PheTES: 58 µL<br>DMSO: 2575 µL<br>A3. Complexation solution:<br>Sulfadiazine: 0.0462 g<br>APTES: 170 µL<br>PheTES: 60 µL<br>DMSO: 2575 µL<br>A4. Complexation solution:<br>Sulfathiazole: 0.0387 g<br>APTES: 170 µL<br>PheTES: 90 µL<br>DMSO: 2575 µL<br>A5. Complexation solution:<br>Sulfamerazine: 0.0504 g<br>APTES: 170 µL<br>PheTES: 85 µL<br>DMSO: 2575 µL<br>A6. Complexation solution:<br>Sulfamethizole: 0.0399 g<br>APTES: 170 µL<br>PheTES: 35 µL |

| Sl. | Template Name | Chemical Structure | Sol Solution Composition |
|---|---|---|---|
| | | | DMSO: 2575 μL<br>B. Sol solution hydrolysis:<br>TEOS: 4500 μL<br>DMSO: 15450 μL<br>HCl (0.1M): 1040 μL<br>Gelation:<br>Both A1-6 and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 71. | DEET | (structure of DEET) | A. Complexation solution:<br>Template: 0.137 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 510 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 72. | Tamoxifen | (structure of Tamoxifen) | A. Complexation solution:<br>Template: 0.2695 g<br>APTES: 340 μL<br>PheTES: 0 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 73. | Acetylsalicylic acid | (structure of Acetylsalicylic acid) | A. Complexation solution:<br>Template: 0.0858 g<br>APTES: 340 μL<br>PheTES: 120 μL<br>DMSO: 5150 μL<br>B. Sol solution hydrolysis:<br>TEOS: 1500 μL<br>DMSO: 5150 μL<br>HCl (0.1M): 520 μL<br>Gelation: |

| Sl. | Template Name | Chemical Structure | Sol Solution Composition |
|---|---|---|---|
| | | | Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 74. | Hydroquinone | 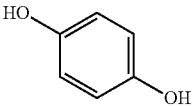 | A. Complexation solution:<br>Template: 0.0786 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 75. | 4-Octylphenol | 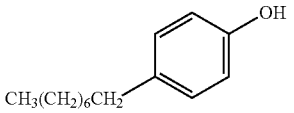 | A. Complexation solution:<br>Template: 0.295 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel. Processing the gel: The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 76. | Nonylphenol | 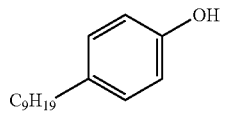 | A. Complexation solution:<br>Template: 0.315 g<br>APTES: 340 μL<br>PheTES: 180 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel. Processing the gel: The gel was heated at 50° C. for 48 h for completing the gelation process. |

| Sl. | Template Name | Chemical Structure | Sol Solution Composition |
|---|---|---|---|
| | | | The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 77. | Safrole | (structure of safrole) | A. Complexation solution:<br>Template: 0.116 g<br>APTES: 340 μL<br>PheTES: 350 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 78. | Sucralose | (structure of sucralose) | A. Complexation solution:<br>Template: 0.081 g<br>APTES: 340 μL<br>PheTES: 0 μL<br>DMSO: 5150 μL<br>B. Sol solution hydrolysis:<br>TEOS: 1500 μL<br>DMSO: 5150 μL<br>HCl (0.1M): 520 μL<br>Gelation:<br>Both A and B solutions were incubated for 12 h followed by adding together. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 μm. Finally, the templates removed using a Soxhlet Extraction Unit/Accelerated Solvent Extraction System. |
| 79. | BTEX | | A1. Complexation solution:<br>Benzene: 0.05 g<br>APTES: 0 μL<br>PheTES: 120 μL<br>DMSO: 1720 μL<br>A2. Complexation solution:<br>Toluene: 0.05 g<br>APTES: 0 μL<br>PheTES: 120 μL<br>DMSO: 1720 μL<br>A3. Complexation solution:<br>Ethylbenzene: 0.05 g<br>APTES: 0 μL<br>PheTES: 120 μL<br>DMSO: 1720 μL<br>A4. Complexation solution:<br>0-Xylene: 0.05 g<br>APTES: 0 μL<br>PheTES: 120 μL<br>DMSO: 1720 μL<br>A5. Complexation solution:<br>p-xylene: 0.05 g |

| Sl. | Template Name | Chemical Structure | Sol Solution Composition |
|---|---|---|---|
| | | | APTES: 0 µL<br>PheTES: 120 µL<br>DMSO: 1720 µL<br>A6. Complexation solution:<br>m-xylene: 0.05 g<br>APTES: 0 µL<br>PheTES: 120 µL<br>DMSO: 1720 µL<br>B. Sol solution hydrolysis:<br>TEOS: 3000 µL<br>DMSO: 10300 µL<br>HCl (0.1M): 1040 µL<br>Gelation:<br>Both A1-6 and B solutions were incubated for 12 h followed by adding together. Subsequently, 900 µL of NH$_4$OH (1M) was added. The mixture form solid gel.<br>Processing the gel:<br>The gel was heated at 50° C. for 48 h for completing the gelation process. The gel was then dried in a vacuum oven for 24 h at 80° C. The particles are then crushed, ground and screened to obtain particle size of 20-50 µm.<br>Finally, the templates removed using a Soxhlet Extraction Unit/Accelerated Solvent Extraction System. |

Example 15—One-Pot Synthesis of a Multi-Template Molecularly Imprinted Polymer for the Extraction of Six Sulfonamide Antibiotic Drugs Residues from Milk A highly selective molecularly imprinted polymer (MIP) sorbent was synthesized and employed for the simultaneous determination of six sulfonamide antibiotic drugs residues (sulfanilamide. sulfacetamide, sulfadiazine, sulfathiazole, sulfamerazine and sulfamethizole) in milk samples. Multi-analytes imprinted particles were applied as the sorbent in solid phase extraction (MIP-SPE). The analytes were determined quantitatively by an accurate and sensitive liquid chromatographic method, which was developed and validated according to the European Union Decision 2002/657/EC. The separation of sulfonamide drugs was performed on an HPLC analytical column (Merck-Lichrospher RP18e, 5 µm 250×4 mm), and the analytes were identified and quantified by diode array detection. Several experimental parameters such as the required loading of the MIP sorbent, mass of milk, volume and type of the elution solvent, as well as time for absorption and elution were investigated in order to obtain optimal experimental conditions. Furthermore, for comparison purpose, a non-imprinted polymer (NIP) was also applied under the optimum conditions. The validation study was based on the investigation of the following parameters: linearity, selectivity, stability, limits of detection and quantitation, decision limit, detection capability, trueness, precision and ruggedness according to the Youden's approach. The decision limit (CCa) and detection capability (CCb) values in the milk were achieved from 101.9 to 113.5 µg·kg$^{-1}$ and from 114.4 to 135.4 µg·kg$^{-1}$, respectively depending on the target sulfonamide drug.

Finally, the optimized protocol was successfully applied to milk samples from local markets in Thessaloniki, Greece as well as to human breast milk sample.

TABLE 6

General structure, molar mass, individual molecular structure and other relevant physicochemical characteristics of selected sulfonamide drugs

| Sulfonamide drug | Abbreviation | Molar mass g/mol | Molecular structure | log K$_{ow}$ |
|---|---|---|---|---|
| General structure | N/A | N/A | 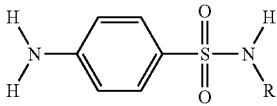 [SMILES: Nc1ccc(S(N)(=O)=O)cc1] | N/A |
| Sulfanilamide | SNM | 172.202 | 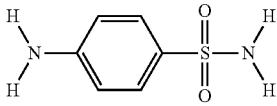 | −0.8 |

TABLE 6-continued

General structure, molar mass, individual molecular structure and
other relevant physicochemical characteristics of selected sulfonamide drugs

| Sulfonamide drug | Abbreviation | Molar mass g/mol | Molecular structure | log $K_{ow}$ |
|---|---|---|---|---|
| Sulfacetamide | SCM | 214.234 | 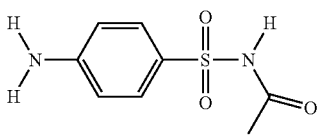 | −0.6 |
| Sulfadiazine | SDZ | 250.276 | 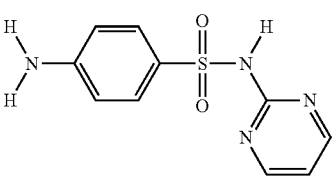 [SMILES: Nc1ccc(S(=O)(=O)Nc2ncccn2)cc1] | −0.2 |
| Sulfathiazole | STZ | 255.310 | 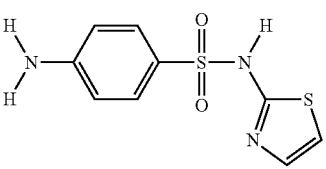 [SMILES: Nc1ccc(S(=O)(=O)Nc2nccs2)cc1] | 0.05 |
| Sulfamerazine | SMZ | 264.303 | 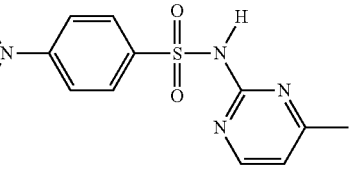 | 0.14 |
| Sulfamethizole | SMX | 270.325 | 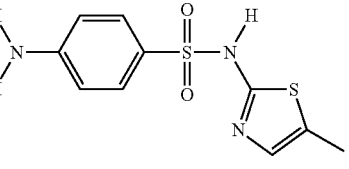 | 0.9 |

2. Experimental

2.1. Chemicals and Reagents

Sulfanilamide (SNM), Sulfacetamide (SCM), Sulfadiazine (SDZ), Sulfathiazole (STZ), Sulfamerazine (SMZ), Sulfamethizole (SMT), Sulfadimethoxine (SDMX), Sulfamethaxozale (SMTX), Sulfisoxazole (SIX), Thiamphenicol, Florfenicol (FFC), Floumekin (FLU) and Oxacillin (OXA) were purchased from Sigma-Aldrich (St. Louis, Mo., USA). Chloramphenicol (CAP) was purchased from Alfa-Aesar (Karlsruhe, Germany). HPLC grade methanol was obtained from Chem-lab NV (Zedelgem, Belgium), while acetonitrile was obtained from Fisher Scientific (Steinheim, UK). Acetic acid was purchased from Merck (Darmstadt, Germany), whereas formic acid was purchased from Chem-Lab NV (Zedelgem, Belgium). Moreover, isopropanol (2-propanol) was supplied by Chem-lab NV and acetone was supplied by Merk. Trisfluoroacetic acid was purchased from Merck and tris-HCl from Duchefa Biochemie (Amsterdam, The Netherlands). High purity water obtained by a Milli-Q purification system (Millipore, Bedford, Mass., USA).

Milk samples were purchased from local food markets (Thessaloniki, Greece). Different varieties of fresh milk were analyzed: (a) skimmed milk (0% fat); (b) semi-skimmed milk (1.5% fat), (c) full-fat milk (3.5% fat). Also, was used breast milk sample from a healthy volunteer. All milk samples were stored refrigerated (at 4° C.), except the breast milk sample which was kept at 0° C.

Equipment and Materials

A gradient HPLC-DAD system was used for the chromatographic analysis. The solvent lines were mixed in an FCV-10AL$_{VP}$ mixer from Shimadzu (Kyoto, Japan). An LC-10AD$_{VP}$ pump combined with a SCL-10AL$_{VP}$ System Controller, permitting fully automated operation, was used to deliver the mobile phase to the analytical column, both of them were purchased from Shimadzu Corporation. The chromatographic system includes a Rheodyne 7725i injection valve (Rheodyne, Cotati, Calif., USA), with a 20 µL loop. The chromatographic separation was based on a Lichrospher RP18e, 5 µm 250×4 mm analytical column by Merck, (Darmstadt, Germany). A SPD-M10A$_{VP}$ (photodiode array detector was applied for the detection of the target molecules. A data acquisition software Lab Solutions-LC solution was equipped by Shimadzu. Degassing of the mobile phase was achieved by helium sparging in the solvent reservoirs by a DGU-10B degassing unit.

A Glasscol small vortexer (Terre Haute, Ind., USA) and an ultrasonic bath Transonic460/H (Elma, Germany) were used for the pretreatment of all milk samples. Evaporations were achieved by a ReactiVap 9 port evaporator model 18780 by Pierce (Rockford, Ill., USA). Q-Max RR syringe filters (0.22 lm nylon membrane) were purchased from Frisenette (Knebel, Denmark). The solid phase extraction system with 12 seats for syringe barrels was applied is a model from Analytichem International (Harbor City, Calif., USA).

Chromatographic Conditions

The separation of six analytes was achieved on the Merck-Lichrospher RP18e (5 µm 250×4 mm) analytical column, that was operated at room temperature. The isocratic eluent program applied for the effective separation with a mobile phase consisted of 80% formic acid 0.1%, 3% ACN and 17% MeOH, at a flow rate 1.0 mL min$^{-1}$. The operating pressure was 167 bar, the wavelength was chosen at 265 nm and the total time of analysis was almost 15.30 min. Retention times were 2.801 min for SNM, 4.856 min for SCM, 5.967 min for SDZ, 7.318 min for STZ, 8.134 min for SMT and 13.387 min for SMT.

Preparation of Six Sulfonamide Drugs Imprinted Sol-Gel Sorbent

Preparation of Sulfonamide Drug-Sol-Gel Functional Precursors Complexes

The self-assembled complex between individual sulfonamide drug template and the sol-gel precursors, 3-APTMS and PTES were obtained by vigorously mixing: 414 mg of sulfanilamide, 170 µL of 3-APTES, 60 µL of PTES, and 2575 µL of dimethyl sulfoxide; 508 mg of sulfacetamide, 170 µL of 3-APTES, 58 µL of PTES, and 2575 µL of dimethyl sulfoxide; 446 mg of sulfadiazine, 170 µL of 3-APTES, 60 µL of PTES, and 2575 µL of dimethyl sulfoxide; 446 mg of sulfathiazole, 170 µL of 3-APTES, 90 µL of PTES, and 2575 µL of dimethyl sulfoxide; 470 mg of sulfamerazine, 170 µL of 3-APTES, 85 µL of PTES, and 2575 µL of dimethyl sulfoxide; 380 mg of sulfamethizole, 170 µL of 3-APTES, 35 µL of PTES, and 2575 µL of dimethyl sulfoxide together followed by sonication for 30 min. The mixture was incubated at room temperature for 6 hr so that a 3D complex with distinct stereochemical orientation between the template and the sol-gel precursors forms via hydrogen bonding and other intermolecular interactions.

Hydrolysis of the Crosslinking Agent

To initiate the hydrolysis of the crosslinking agent, TEOS, 4500 µL of it was added to 15450 µL of dimethyl sulfoxide and was thoroughly mixed by vortexing for 5 min. Subsequently, 1040 µL of 0.1 M HCl was added to the mixture and kept in a silicon oil bath at 50° C. for 12 hr to ensure complete hydrolysis of the sol-gel precursor.

Sol-Gel Condensation to Form 3D Molecularly Imprinted Polymer (MIP) Network

The complex mixture containing the template was then added to the hydrolyzed solution of the cross-linking reagent and was vortexed for another 5 min. The sol solution containing the sulfonamide template was kept at 50° C. in the silicon oil bath for 4 hr to form the transparent gel, followed by another 24 hr at the same temperature for aging and ripening of the network.

Removal of the Templates from Sol-Gel MIP Sorbent

Following the preparation of sol-gel MIP sorbent, the templates (sulfonamide drugs) have to be quantitatively removed from the polymer particles so that imprinted cavities complimentary to the size, shape, and functionality of the template molecules are left behind throughout the matrix of the particles. Experiments showed that methanol was suitable for quantitative removal of sulfonamide drugs from the sol-gel MIP sorbent after 10 cycles of sonication with 10 mL of methanol for 30 min. Alternatively, 10 times of centrifugation for 30 min with 10 mL MeOH at 1900 g may be used for exhaustive removal of the templates. Solvent mediated template removal continued until washing solution became free from sulfa drugs, which was checked by HPLC analysis.

The template-free particulates were then dried in an oven at 50° C. for 30 min. Non-imprinted sol-gel polymer sorbent (sol-gel NIP) was prepared following the same procedure established for imprinted polymer sorbent except that the sulfonamide drugs (template) removal step was omitted from the protocol.

Creation of Narrowly Dispersed Sulfonamide Imprinted Particles for Packing into Solid Phase Extraction Column The dried MIP and NIP sorbents were crushed and grinded in a ceramic mortar with a pestle to form fine particles. Subsequently, the particles were mesh screened to obtain particle size between 44 µm (325 mesh) and 53 µm (270 mesh). The particles were then packed in 5 mL empty solid phase extraction syringe barrels after placing a frit on the front end of the barrel to retain the particles.

Preparation of Standard Solutions and Treatment of Milk Samples for Fat and Protein Removal Stock standard solutions of each antibiotic drug (100 mg L$^{-1}$) were prepared in methanol and stored at 4° C. The standard solutions were found stable for five months. The working standard solutions were prepared by further dilution in the mobile phase mixture. The range of their concentrations is between 0.02 and 10 mg L$^{-1}$. These solutions were stable for six weeks in the temperature conditions that are mentioned above.

Different types of milk samples were purchased from local market and were applied according to the protocol. The milk samples included skimmed fresh milk with 0% fat; semi-skimmed fresh milk with 1.5% fat; full-fat fresh milk with 3.5% fat; and human breast milk. For the matrix adjusted milk calibration curve, spiked skimmed milk with 0% fat was used. The breast milk was obtained from a volunteer. For the steady performance of the experiments, all milk samples used in the study had undergone protein precipitation by adding 2 mL ACN to 1 g of every type of milk.

Optimization of Solid Phase Extraction Conditions

Extraction columns were prepared by packing 30 mg of MIP and NIP particles in 5 mL empty syringe barrels, one frit was placed to the bottom of the particles while the top was free of every stopper type. The frits were obtained from commercial SPE cartridges. These homemade cartridges were applied to the SPE system. As it is observed the conditioning of MIPSPE columns is not a necessary step, so it was avoided in order to minimize the time of the extraction procedure.

After every loading of a sample (standard or spiked milk sample), the syringe barrels were washed with 2 mL methanol in order to remove any contaminants and to be ready for the next extraction. In order to obtain optimum extraction conditions, several extraction parameters for the imprinted and non-imprinted polymer were thoroughly investigated. Fifteen elution systems were applied: methanol, acetonitrile, acetone, 2-propanol, MeOH-ACN 50:50 v/v, 0.1% formic acid-MeOH-ACN 90:5:5% v/v, 1% formic acid-MeOH-ACN 50:25:25% v/v, 1% acetic acid-MeOH-ACN 50:25:25% v/v, 1% acetic acid-MeOH-ACN 50:10:40% v/v, 1% acetic acid-MeOH-ACN 50:40:10% v/v, 1% acetic acid-MeOH-ACN 40:10:50% v/v, 1% acetic acid-ACN 50:50% v/v, 1% acetic acid-ACN 40:60% v/v, 1% acetic acid-ACN 60:40% v/v and 0.5% acetic acid-ACN 50:50% v/v. Sample loading time as well as extraction time were checked at 0, 2, 5, 10, 15 and 20 min. Moreover, the flow rate of sample solutions and elution solvent, was checked in 0.5 and 1 mL min$^{-1}$. The effect of the volume of eluent solution was checked in 0.5, 1 and 2 mL, by passing 500 mL of a 5 ng μL$^{-1}$ solution to a 30 mg sorbent and measuring the amount of sulfonamide drug eluted into the liquid phase by HPLC-DAD.

The MIP was applied on SPE as sorbent and on an epperndorf pipette tip (with and without sonication at sample loading and extraction step, respectively).

Method Validation According to European Decision/2002/657/EC

The developed MIPSPE method was validated according to the performance criteria of European Commission 2002/657/EC using spiked milk samples. These criteria were the following: selectivity, linearity, trueness, precision (repeatability and between-day precision), decision limit ($CC_a$), detection capability ($CC_b$) and ruggedness.

Linearity was evaluated by a triplicate analysis covering the whole working range for standard solutions as well as spiked milk samples. The results were checked by using constructing calibration curves. The least square linear regression analysis was utilized by calculating the slope, intercepting and coefficient of determination. Limits of detection (LOD) and quantification (LOQ) were calculated by the standard deviation of y-intercept of regression analysis (σ) and the slope (S). The calculations were done with the use of the equations LOD=3.3 σ/S and LOQ=10 σ/S respectively.

The decision limit ($CC_a$) was calculated as the mean measured concentration at the MRL for each compound plus 1.64-times the standard deviation (SD) of within-day precision at this concentration. The detection capability ($CC_b$) was calculated as $CC_a$ plus 1.64-times the SD of within-day repeatability at CCa. Statistical analysis was performed at the 95% confidence level and the number of replicate analyses was 6.

The deproteinized skimmed milk (0% fat) was spiked at 0.5 MRL, MRL and 1.5 MRL and analyzed in triplicate (n=3) in order to estimate the accuracy and the precision of the method. The precision of the method was evaluated by calculating the relative standard deviation (RSD) for the repeated measurements, and the accuracy of the standard deviation (SD) between nominal and measured concentrations. The accuracy of the method was checked by analyzing the three concentration levels of extracted sulfonamides. Within-day repeatability was tested from the three different concentrations on the same day. Between-day repeatability was calculated by performing triplicate analysis at the same concentration levels in four days.

The selectivity was determined by analyzing the blank milk samples for each type of milk, which are mentioned above. The purpose of these analyzes was to verify if the absence of interfering peaks was at the same time of examined sulfa drugs.

Standards stock and working solutions were found stable at 4° C. for four months and five weeks respectively. Moreover, the stability of the spiked milk samples was assessed in a previous study.

The ruggedness of the method was estimated by the Youden's approach. Seven different parameters were selected from the sample procedure. The operation of the method was tested when small and deliberate changes of these parameters were introduced at once. The introduced experimental design was described in the Decision 2002/657/EC. The following parameters were investigated: milk volume, mass of sorbent material, elution solvent, volume of elution solvent, extraction time, desorption time and pre-conditioning of the sorbent material. A, B, C, D, E, F, and G indicate the selected seven factors at their nominal level. The alternative values, which were deliberately changed from the nominal values, are given by the lower letters a, b, c, d, e, f, and g. These combinations correspond to eight experiments, which are illustrated as s, t, u, v, w, x, y and z (Table 7).

TABLE 7

Ruggedness tested by imposing seven small but deliberate changes in the operating parameters.

| Factor | Unit | Nominal level | Alternative value | Experiment number | | | | | | | |
|---|---|---|---|---|---|---|---|---|---|---|---|
| | | | | 1 | 2 | 3 | 4 | 5 | 6 | 7 | 8 |
| Mass of milk | g | 1 | 0.5 | A | A | A | A | a | a | a | a |
| MIP sorbent mass | mg | 30 | 40 | B | B | b | b | B | B | b | b |
| Volume of elution solvent | mL | 2 | 1 | C | c | C | c | C | c | C | c |
| Desorption time | min | 15 | 10 | D | D | d | d | d | d | D | D |
| Extraction time | min | 15 | 10 | E | e | E | e | E | e | E | e |
| Elution solvent | type | CH$_3$COOH:MeOH:ACN (50:10:40% v/v) | H$_2$O:MeOH:ACN (50:10:40% v/v) | F | f | f | F | F | f | f | F |
| Preconditioning of MIP sorbent | yes/no | no | yes | G | g | g | G | g | G | G | g |
| Results | | | | s | t | u | v | w | x | y | z |

2.2. Batch Rebinding Experiments 2.2.1. Selectivity Studies

The selectivity of MIP particles for the six sulfonamides was tested. For these experiments were used SPE cartridges packed with 30 mg of MIP and NIP particles respectively. Standard solutions containing 5 ng μL$^{-1}$ were passed through the SPE cartridges by holding imprinted or non-imprinted particles at a flow rate of 1 mL/min by the aid of a vacuum system. Several antibiotics have similar structure to the sulfonamides as well as antibiotics with different structure and functional groups were studied (chloramphenicol, thiamphenicol, florfenicol, flumequine, sulfisoxazole, sulfamethoxazole, sulfadimethoxine). The extraction on each antibiotic based on the optimum conditions and the extracted antibiotics were determined by the HPLC system. Imprinting factor (IF) of MIP particles was determined by the following equation:

$$IF = \frac{Kmip}{Knip}$$

where $K_{mip}$ and $K_{nip}$ are the partition coefficients of analyte for MIP and NIP, respectively which are determined by $K=C_b/C_u$ where $C_b$ is the amount of sulfonamides bound by MIP or NIP and $C_u$ is the concentration of free sulfonamides mixture remains in the solution.

2.2.2. Capacity Studies

In order to calculate the sorption capacity at equilibrium a SPE cartridge packed with 30 mg of MIP particles was used. Experiments under optimum conditions were carried out sequentially on the same SPE cartridge. In each subsequent test, the initial concentration was increased in a range 10-1000 ng $\mu L^{-1}$ and the final concentration was determined by HPLC-DAD. The amount of adsorbed (mg/g) was calculated by using the formula reported by Vanderborght and Van Griekenm:

$$Q = (Ci - Ce) * \frac{V}{m}$$

Were $C_i$ is the initial concentration (mg/L), $C_e$ is the equilibrium concentration (mg/L), V is the volume (L) and m is the mass (g) of the adsorbent.

3. Results and Discussion 3.1. Preparation Sol-Gel MIP and Sol-Gel NIP

The entire molecular imprinting process consists of four steps including: (a) complexation of sol-gel functional precursors, 3-APTES and triethoxyphenylsilane (PTES) with sulfonamide drug templates; (b) acid catalyzed hydrolysis of crosslinking sol-gel precursor; (c) simultaneous hydrolysis of functional precursor and condensation of hydrolyzed precursors to form a 3D sol-gel networks with encapsulated templates; (c) removal of the template from sol-gel 3D polymeric networks.

The success of sol-gel molecular imprinting largely depends on the judicious selection of the functional precursor(s), crosslinking precursor, solvent/porogen, catalyst, water and their relative molar ratio as well as the reaction and processing conditions. Due to the presence of benzene ring as well as a large number of hydrogen bond donor and acceptor in sulfonamide drugs, sol-gel precursors, triethoxyphenylsilane (to provide μ-μ interaction) and 3-APTES (to provide hydrogen bonding interaction) were chosen. During the complexation, both the precursors positioned themselves around the template utilizing their specific interaction capability. As such, a template-precursors complex was formed with a distinct 3D stereo-chemical orientation of the participating entities. To ensure uninterrupted interactions between the template and precursors, isopropanol, a relatively nonpolar solvent was used as the reaction medium.

Another important task in sol-gel MIP synthesis is to obtain complete hydrolysis of crosslinking sol-gel precursor that may ensure successful integration of the template complex into the 3D sol-gel network. Complete hydrolysis of the methoxy functional groups into hydroxyl functional groups was ensured by dissolving TEOS in an appropriate volume of solvent/porogen isopropanol and reacting with water in presence of HCl as a catalyst for a prolonged period of time under elevated temperature.

When the template-precursors complex is added to the sol solution containing the hydrolyzed crosslinking agent, simultaneous hydrolysis and condensation of the functional precursors as well as the condensation of the hydrolyzed crosslinking agent begin in presence of the acid catalyst and elevated reaction temperature condition. Soon, a 3D networks of sol-gel polymeric networks with entrapped template and solvent/porogen emerges. Aging and ripening of the sol-gel network for a prolonged period of time ensures that the condensation has progressed towards completion and therefore, the subsequent removal of the solvent and the template from the sol-gel networks would not disturbs its structural and morphological integrity, an important aspect of molecular imprinting.

3.2. Optimization of MIP-SPE Procedure

The following studies were performed in order to achieve the optimum conditions for the final protocol and to evaluate the effect of each parameter.

Firstly, the MIP sorbent was applied as SPE sorbent and on an eppendorf pipette tip (with and without sonication at sample loading and extraction step, respectively). These three approaches were investigated for standard solutions and milk samples. The results are represented on Table 8. According to the data the MIP as SPE sorbent has better recovery for standard and spiked milk samples. Consequently, this approach was selected for further experiments.

TABLE 8

Recovery results obtained from standard samples in deionized water and spiked milk samples (numbers in parenthesis).

| Compound | Recovery % | | |
|---|---|---|---|
| | SPE | Eppendorf | Eppendorf supported by sonication |
| Sulfanilamide | 13.6 (6.8) | 9.2 (4.2) | 11.3 (5.6) |
| Sulfacetamide | 17.5 (5.3) | 17.9 (5.8) | 24.0 (2.0) |
| Sulfadiazine | 14.2 (4.4) | 10.5 (3.4) | 10.1 (5.8) |
| Sulfathiazole | 12.5 (5.9) | 9.1 (3.6) | 12.8 (2.2) |
| Sulfamerazine | 13.1 (6.2) | 8.3 (4.2) | 9.5 (2.5) |
| Sulfamethizole | 44.7 (10.3) | 53.0 (10.5) | 38.8 (10.7) |

3.2.1. Effect of Sample Loading and Extraction Time

Figure 10A:
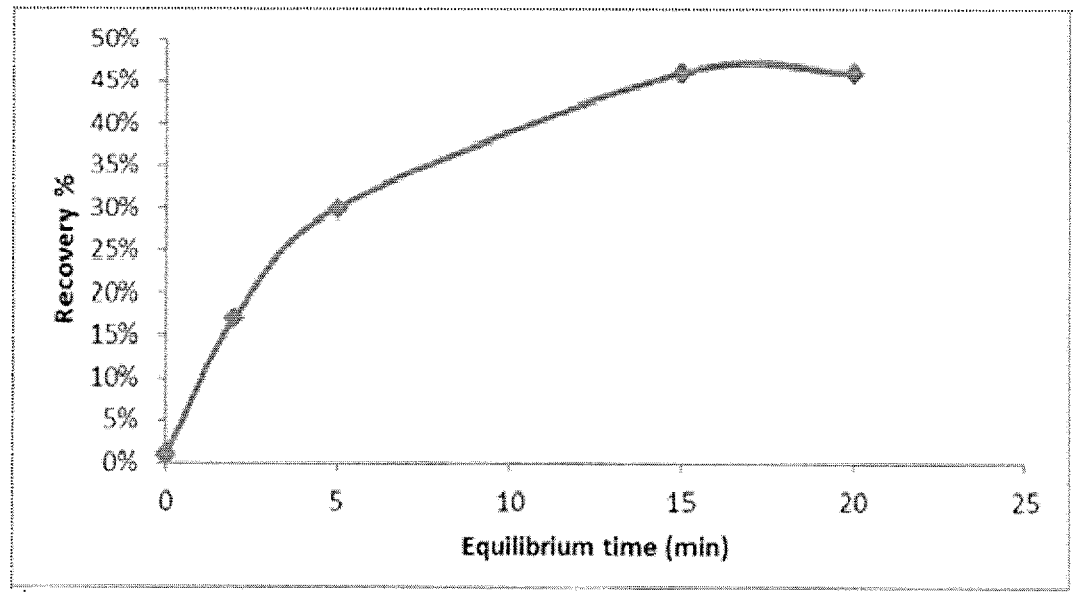
FIGS. 10A-10C show the impact of equilibration time (10A), extraction time (10B) and sorbent mass loading (10C) on the recovery of sulfonamide drugs.
Figure 10B:
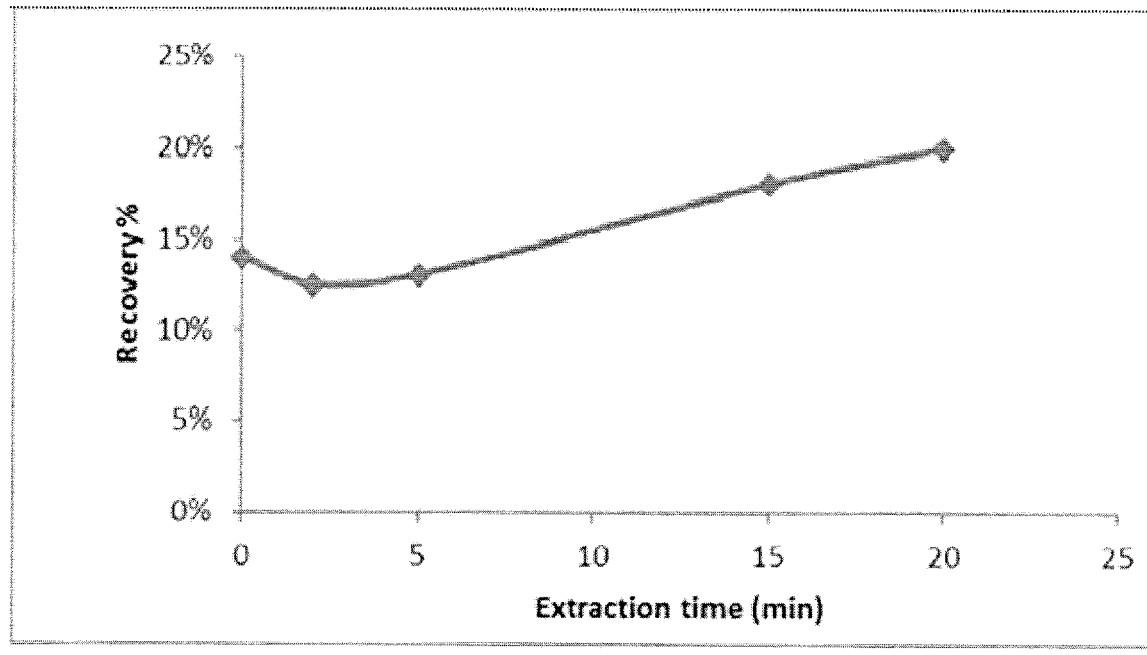

Standard and spiked solutions as well as the elution solvent were allowed to interact with the sol-gel MIP sorbent before passing through the column. During the sample loading and the elution, different times were evaluated at 0.2, 5, 15 and 20 min. Fifteen minutes were selected by the equilibrium and extraction time with the highest recovery, as it is shown by FIG. 10 (A, B).

Figure 10C:
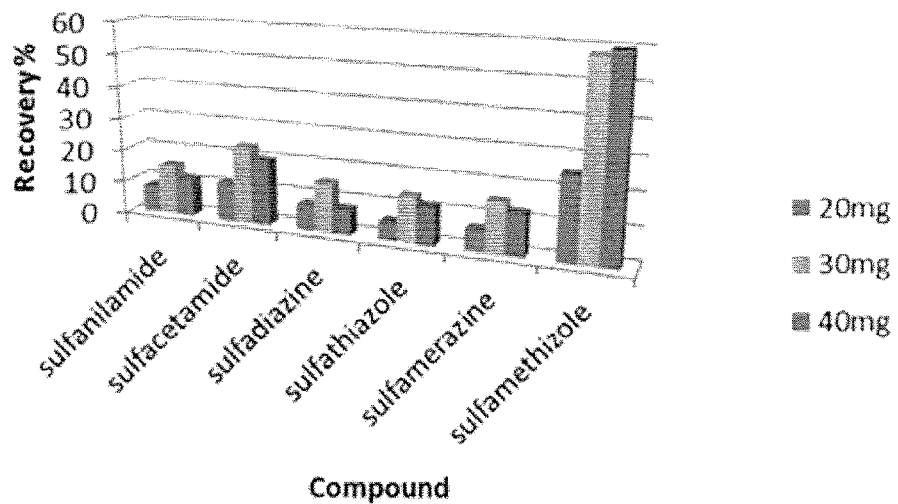

Furthermore, the amount of MIP particles was investigated with tests at 20, 30 and 40 mg, with their results shown on FIG. 10(C). Under the identical extraction conditions, 30 mg of sorbent loading provided the highest extraction recovery.

The aforementioned conditions (30 mg of MIP particles, 15 min equilibrium time, 15 min extraction time, 2 mL of 1% CH$_3$COOH-MeOH-ACN 50:10:40% v/v at a flow rate 1 mL min$^{-1}$) were applied to MIP-6 sulfa with small changes in order to obtain the final conditions at this absorbent. As mentioned above 2 mL of elution system were selected for the experiments at the complex absorbent material.

Figure 11A:
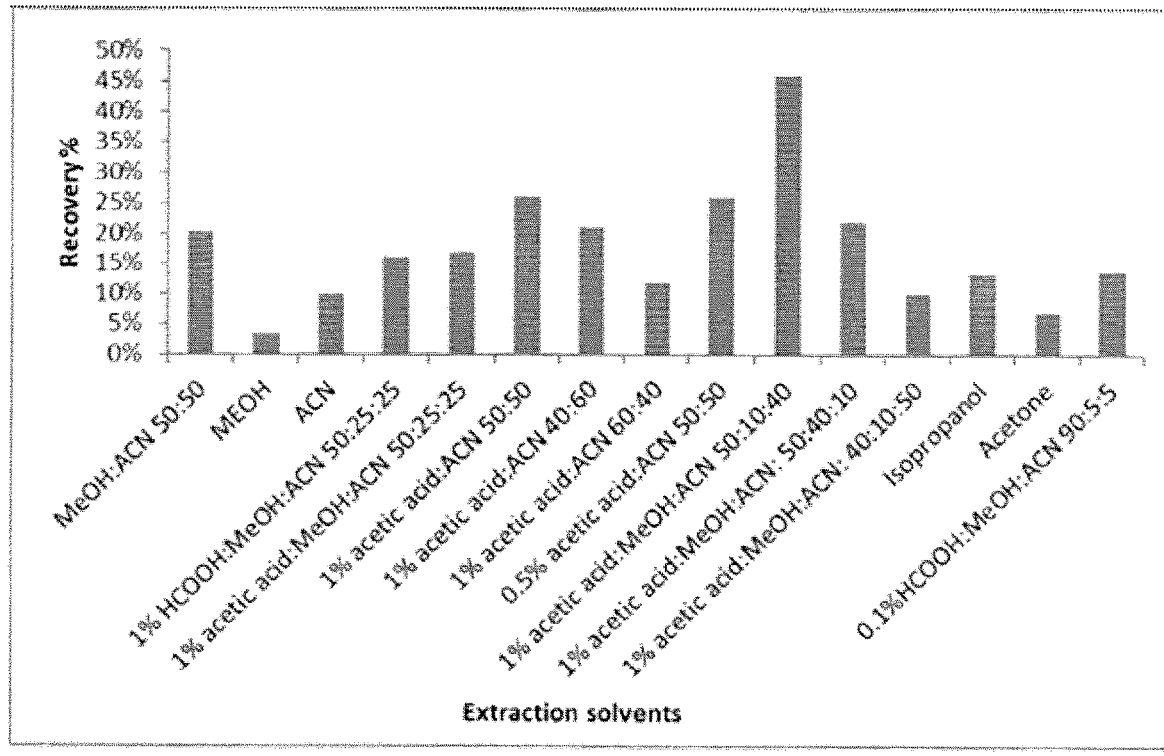
FIGS. 11A-11C show the impact of elution solvents on percentage recovery (11A), imprinting factor (11B) and elution solvent volume on percentage recovery (11C).
Figure 11B:
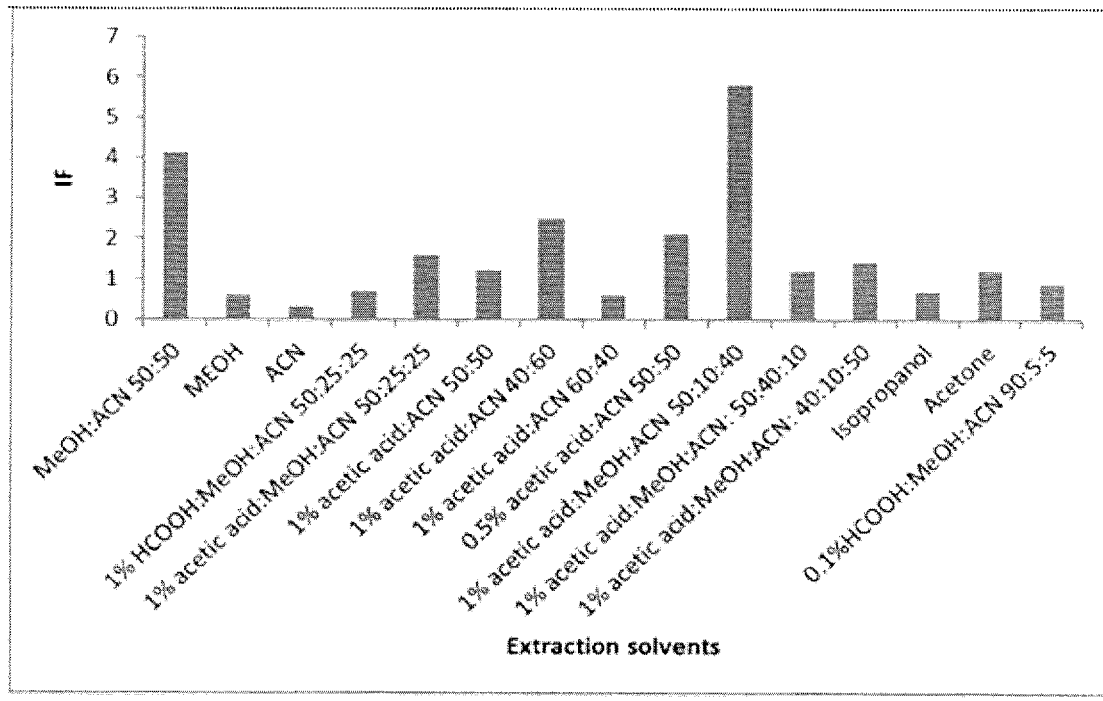

3.2.2. Effect of Type, Volume and Flow Rate of Elution Solvent System for the Extraction of Sulfonamide Drugs Taking into consideration the above description, various elution systems were applied and evaluated for the effective extraction of the sulfathiazole from the MIP particles. In FIG. 11, it is shown that 1% acetic acid-MeOH-ACN 50:10:40% v/v was provided the highest recovery. This elution solvent was chosen for further experiments which performed for the extraction of six SAs. The sorption of SAs to imprinted polymers was significantly higher than in the non-imprinted in all examined solvents. The given IFs of each elution system are represented in the FIG. 11 (B). The proposed elution system has better recovery for the STZ and highest IF value than the others.

Figure 11C:
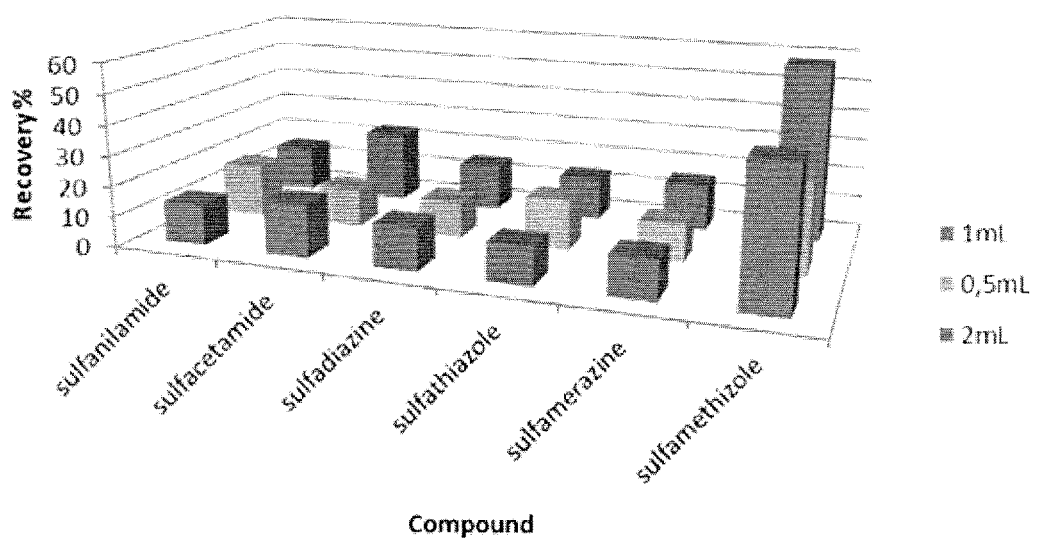

The volume of the elution system was checked to the MIP particles, at 0.5, 1 and 2 mL. Finally 2 mL, as it is shown in FIG. 11(C) provided the highest recovery.

The flow rate of sample solution and elution solvent was tested in 0.5 and 1 mL min$^{-1}$. The flow rate at 1 mL min$^{-1}$ was preferable because it had better reproducibility.

3.2.3. Fat and Protein Removal from Milk Samples

Deproteinization tests were applied in order to eliminate the impact of fat and proteins to recovery during the sample preparation procedure. Fats and proteins could interfere with the binding sites and block the performance of MIP particles. Precipitation was carried out with the use of acetonitrile, trifluoroacetic acid 10% v/v, tris-HCl 20% v/v and acetone. The results with the highest recovery and the best behavior during the centrifugation were received by using acetonitrile (Table 9).

Several amounts of 0.5, 1, and 2 g milk were investigated. The amount of 1 g had the best results and was selected for the experiments. It is worth noting that the entire method development and validation was carried out by the use of skimmed milk (0% fat) spiked with the six SAs.

TABLE 9

Impact of different protein and fat removing solvents on extraction recovery

| Protein precipitation agent | Recovery % | | | | | |
|---|---|---|---|---|---|---|
| | SNM | SCM | SDZ | STZ | SMZ | SMT |
| Acetonitrile | 6.8 | 5.3 | 4.4 | 5.9 | 6.2 | 10.3 |
| Trifluoroacetic acid 10% v/v | 1.2 | 2.0 | 4.4 | 2.4 | 2.5 | 7.3 |
| Trichloride 20% v/v | — | 2.0 | 1.5 | 1.7 | 2.5 | 2.5 |
| Acetone | 1.4 | 0.7 | 3.4 | 1.4 | 0.6 | 1.5 |

3.2.4. Optimum MIP-SPE Protocol

Optimized MIPSPE conditions include the use of 30 mg of MIP sorbent in 2 mL empty syringe barrels, without preconditioning before loading the samples. An aliquot of 1 g of skimmed milk was deproteinized by 2 mL acetonitrile. After loading the samples an equilibration time of 15 min is demanded. The effective elution of six target sulfonamides was carried out by 2 mL of 1% CH$_3$COOH-MeOH-ACN 50:10:40% v/v at a flow rate of 1 mL min$^{-1}$. The eluent is evaporated until dryness in stream of nitrogen. The measurements are completed on the HPLC-DAD system.

3.3. Maximum Adsorption Capacity of the Sol-Gel Molecularly Imprinted Sorbent

Figure 12:
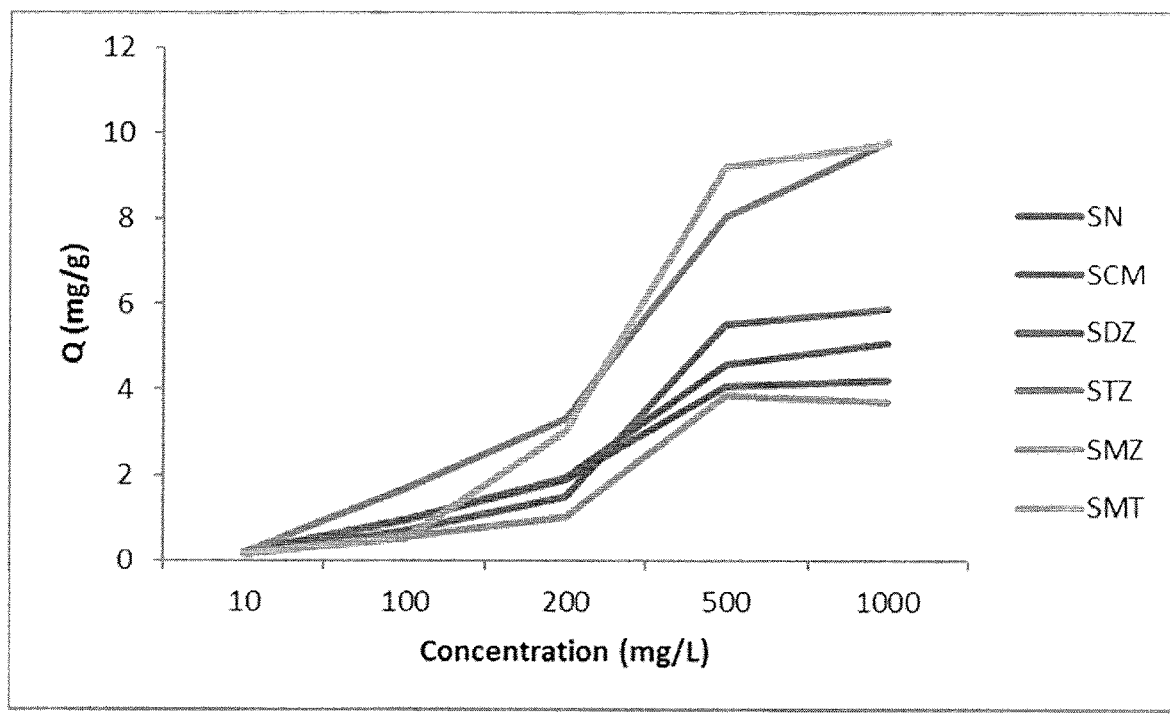
FIG. 12 shows the maximum adsorbent capacity of sol-gel MIP sorbent

In order to determine the sorption capacity of the sol-gel imprinted polymer (maximum amount of the template retained by 1 g of MIP), 30 mg of these polymer were saturated with target molecules under optimum conditions, by passing several amounts of 10, 50, 100, 200, 500 and 1000 mg/L mixture of 6 sulfa drugs solution subsequently. The final Ce concentrations were calculated on HPLC. The maximum capacity (Q, mg/g) for each of the six compounds was determined with the above equation. The results are represented in FIG. 12.

Validation of MIP-SPE Method 3.3.1. Linearity and Sensitivity

Samples were prepared by spiking blank milk sample matrix with a mixture of six sulfa drugs corresponding to concentrations of 50-500 mg/kg. Calibration curves for milk samples, the LOQs and LODs are given in the Table 10.

TABLE 10

Analytical figures of merit of MISPE/HPLC-DAD method

| Analyte | Calibration Curve | Coefficient of variance ($r^2$) | LOD (µg/kg) | LOQ (µg/kg) |
|---|---|---|---|---|
| Sulfanilamide | y = (10,733 ± 0.7945)x + (153.94 ± 124.04) | 0.9892 | 3.1 | 9.1 |
| Sulfacetamide | y = (4.8776 ± 0.3570)x + (683.48 ± 95.2884) | 0.9894 | 13.3 | 39.3 |
| Sulfadiazine | y = (32.32 ± 5.8319)x + (3700 ± 1537.48) | 0.9325 | 14.1 | 42.2 |
| Sulfathiazole | y = (4.1923 ± 0.1119)x + (980.69 ± 17.6956) | 0.9993 | 1.9 | 5.6 |
| Sulfamerazine | y = (7.1455 ± 0.4119)x + (1115.5 ± 117.4264) | 0.9934 | 8.9 | 26.6 |
| Sulfamethizole | y = (12.852 ± 0.5027)x + (1193.5 ± 47.6419) | 0.9969 | 12.6 | 37.8 |

3.3.2. Precision and Accuracy

The precision of the method was evaluated by within-day repeatability using spiked milk samples at 0.5 MRL, MRL and 1.5 MRL and the accuracy was estimated at the same concentrations by between-day repeatability. The results were evaluated by means of relative standard deviation (RSD) and are represented in the following tables. For within-day repeatability, RSDs were lower than 13.4%, while for between-day repeatability RSDs were lower than 9.9% (Table 11)

TABLE 11

Repeatability, intermediate precision and accuracy data of the MISPE/HPLC-DAD method

| | | Within-day repeatablity (n = 4) | | | Between-day repeatability (n = 3x4) | | |
|---|---|---|---|---|---|---|---|
| Analyte | Spiked (µg/kg) | Inter-assay found ± SD (µg/kg) | RSD % | R % | Inter-assay found ± SD (µg/kg) | RSD % | R% |
| SNM | 50 | 56.0 ± 4.2 | 7.5 | 112.0 | 53.9 ± 2.6 | 4.9 | 107.8 |
| | 100 | 90.8 ± 4.3 | 4.8 | 90.8 | 90.2 ± 3.9 | 4.4 | 90.2 |
| | 150 | 148.0 ± 4.0 | 2.7 | 98.7 | 150.0 ± 6.8 | 4.6 | 100.0 |
| SCM | 50 | 45.0 ± 1.4 | 3.2 | 90.0 | 49.5 ± 4.9 | 9.9 | 99.0 |
| | 100 | 97.1 ± 11.3 | 11.6 | 97.1 | 95.6 ± 7.8 | 8.1 | 95.6 |
| | 150 | 173.5 ± 8.1 | 4.7 | 115.7 | 160.5 ± 10.3 | 6.4 | 107.0 |
| SDZ | 50 | 42.9 ± 0.7 | 1.6 | 85.8 | 42.9 ± 0.9 | 2.3 | 85.8 |
| | 100 | 103.5 ± 0.5 | 0.5 | 103.5 | 101.9 ± 3.1 | 3.0 | 101.9 |
| | 150 | 137.9 ± 4.2 | 3.1 | 91.9 | 140.1 ± 3.2 | 2.2 | 93.4 |
| STZ | 50 | 52.3 ± 1.2 | 2.3 | 104.6 | 51.7 ± 0.8 | 1.6 | 103.4 |
| | 100 | 95.5 ± 6.3 | 6.6 | 95.5 | 98.9 ± 2.0 | 2.9 | 98.9 |
| | 150 | 155.1 ± 1.0 | 0.6 | 103.4 | 151.1 ± 3.9 | 2.6 | 100.7 |
| SMZ | 50 | 57.2 ± 7.6 | 13.4 | 114.4 | 54.6 ± 4.0 | 7.3 | 109.2 |
| | 100 | 102.7 ± 5.9 | 5.8 | 102.7 | 99.7 ± 4.1 | 4.1 | 99.7 |
| | 150 | 157.8 ± 1.6 | 1.0 | 105.2 | 151.3 ± 4.3 | 2.8 | 100.8 |
| SMT | 50 | 51.6 ± 3.2 | 6.1 | 103.2 | 49.9 ± 1.8 | 3.6 | 99.8 |
| | 100 | 106.0 ± 2.2 | 2.1 | 106.0 | 103.5 ± 1.4 | 1.3 | 103.5 |
| | 150 | 149.8 ± 2.2 | 1.4 | 99.9 | 151.3 ± 4.3 | 2.8 | 100.8 |

3.3.3. Selectivity

To examine the selectivity of a sol-gel MIP for the six analytes, a non-imprinted polymer (sol-gel NIP) was synthesized in the same way as sol-gel MIP with the absence of the six templates. Imprinting factor exhibits the tendency of the MIP to selectively recognize and bind the template. So, SPE was prepared for MIP and NIP. Imprinting factor (IF), which is an indicators, express the adsorption affinity of recognition sites to the imprinted sulfonamides. Table 12 summarizes the IF values for the examined sulfonamides when extraction was carried out from protein precipitated milk.

TABLE 12

Adsorption capacity and imprinting factor values for sulfonamide drugs.

| Sulfonamide Drug | Adsorption Capacity, Q(mg/g) | Imprinting Factor (IF) |
| --- | --- | --- |
| Sulfanilamide | 6.0 | 1.56 |
| Sulfacetamide | 5.1 | 2.70 |
| Sulfadiazine | 4.2 | 1.70 |
| Sulfathiazole | 9.8 | 3.90 |

TABLE 12-continued

Adsorption capacity and imprinting factor values for sulfonamide drugs.

| Sulfonamide Drug | Adsorption Capacity, Q(mg/g) | Imprinting Factor (IF) |
| --- | --- | --- |
| Sulfamerazine | 3.7 | 1.13 |
| Sulfamethizole | 9.8 | 4.52 |

Furthermore, in order to determine the selectivity of the material for the six target molecules, tests were carried out applying the optimum protocol for structurally similar and for different compounds. Tests were performed with 5 ng/µL of standard solutions. The tested compounds as well as the recoveries are given in Table 13. The results proved that MIP (6-sulfa) is not capable for recognizing the compounds with a completely different structure, but it appears to be selective for other sulfonamides beyond the six SAs, for which it is intended to be used. This happens because all sulfonamides have a common building structure.

TABLE 13

Comparison in recovery values between structurally similar and different compounds

| Compound | Molecular Structure | Recovery % |
| --- | --- | --- |
| Chloramphenicol | 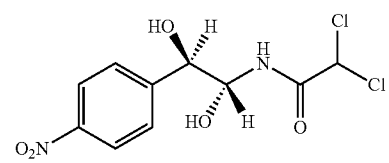 [SMILES: O=C(N[C@H](O)[C@H](O)c1ccc([N+](=O)[O-])cc1)C(Cl)Cl] | — |
| Thiamplenicol | 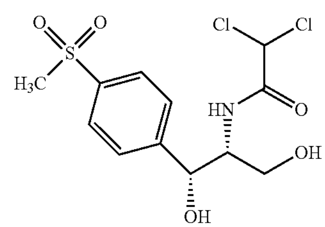 [SMILES: CS(=O)(=O)c1ccc([C@@H](O)[C@@H](CO)NC(=O)C(Cl)Cl)cc1] | — |
| Florfenicol | 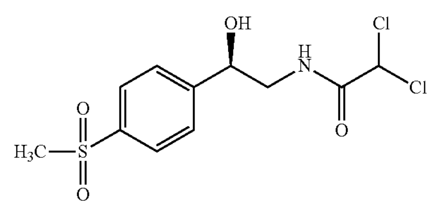 [SMILES: CS(=O)(=O)c1ccc([C@@H](O)CNC(=O)C(Cl)Cl)cc1] | — |
| Flumequine | 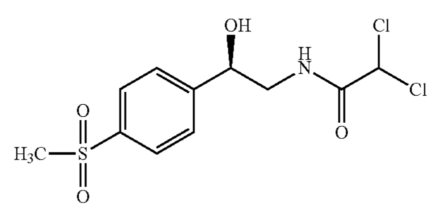 [SMILES: CS(=O)(=O)c1ccc([C@@H](O)CNC(=O)C(Cl)Cl)cc1] | — |

TABLE 13-continued

Comparison in recovery values between structurally similar and different compounds

| Compound | Molecular Structure | Recovery % |
|---|---|---|
| Oxacillin | [structure] | — |
| Sulfadimethoxine | [structure] | 18 |
| Sulfamethoxazole | [structure] | 25 |
| Sulfisoxazole | [structure] | 42 |

3.3.4. Decision Limit and Detection Capability

The determination of $CC_\alpha$ (decision limit) and $CC_\beta$ (capability detection) was demanded according to European Union Decision 2002/657/EE. Decision limit ($CC_\alpha$) values were calculated by spiking six blank milk samples at MRL level (100 μg/kg) and were 106.7 μg/kg for SNM, 113.4 μg/kg for SCM, 104.1 μg/kg for SDZ, 105.6 μg/kg for STZ, 101.9 μg/kg for SMZ and 102.9 for SMT. $CC_\beta$ values were estimated by analyzing six blank spiked milk samples at corresponding $CC_\alpha$ level for each analyte and were 120.7 μg/kg for SNM, 115.84 μg/kg for SCM, 129.9 μg/kg for SDZ, 135.4 μg/kg for STZ, 119.9 μg/kg for SMZ and 114.4 μg/kg for SMT.

3.3.5. Youden Ruggedness Test

The results from the ruggedness experiments are given in Table 14. From the data obtained, it is obvious that the SNM had a positive effect from the volume of the elution system, whereas had not negative effect from any parameter. The SCM was affected negative by the type of elution system. Furthermore, the mass of milk and the mass of the adsorbent had a greater positive effect in the SDZ. Respectively, the elution time and the preconditioning reacted negative to the STZ. The elution time and the eluent system appeared negative effect to the SMZ, while the volume of the elution solvent reacted positive. Finally, the loading time, the elution time, and the type of elution system had negative influence to the SMT. In general, the method is robust since all values were close to the method's values.

TABLE 14

Results of the Youden Ruggedness Test

| Compound | $A_A$ | $A_A^-$ / $A_a$ | $A_B^-$ / $A_b$ | $A_C^-$ / $A_c$ | $A_D^-$ / $A_d$ | $A_E^-$ / $A_e$ | $A_F^-$ / $A_f$ | $A_G^-$ / $A_g$ |
|---|---|---|---|---|---|---|---|---|
| SNM | 3930 | 3332 | 3267 | 3721 | 1964 | 1427 | 1293 | 2711 |
| SCM | 2298 | 1697 | 1212 | 1544 | 751 | 394 | −2090 | 344 |
| SDZ | 7337 | 6475 | 7066 | 4028 | 2693 | 2955 | 1492 | 2696 |
| STZ | 1366 | 257 | 413 | 796 | 1252 | −1480 | 148 | −10 |
| SMZ | 4614 | 3589 | 3710 | 4043 | 2257 | −3149 | −711 | 1857 |
| SMT | 7649 | 171 | 2257 | 2214 | −6241 | −5533 | −10204 | 1829 |

TABLE 15

Validation parameters of the MIPSPE method for the determination of sulfonamides in milk samples.

| Validation parameters | value |
| --- | --- |
| Linear range µg/kg | 50-500 |
| Linearity $R^2$ | >0.9325 |
| LOD = 3.3 S/N | 1.9-13.3 µg/kg |
| LOQ = 10 S/N | 5.6-42.2 µg/kg |
| $CC_a$ | 101.9-113.4 µg/kg |
| $CC_b$ | 114.4-135.4 µg/kg |
| Intra assay | 85.8-115.7% |
| precision at 3 concetrations levels, n = 4 | RSD % <13.4% |
| Inter assay | 85.8-109.2% |
| precision at 3 concetrations levels, n = 4 × 3 | RSD % <9.9% |
| Youden Test | Stable method |

3.4. Application of MIP-SPE/HPLC-DAD Method to Commercial Milk Samples

The developed MIPSPE method was applied for the determination of the six sulfonamides in commercial milk samples and in breast milk. Four random samples of three different types of milk including full-fat (3.5%) milk, semi-skimmed milk (1.5%) and skimmed (0%) were obtained from a local food store and were analyzed. None of the analyzed samples was found to contain sulfonamides at a concentration higher than the method limit of detection.

Furthermore, the MIPSPE method was applied to breast milk sample. According to the results there is no influence originated by the matrix. The proposed method could be applied to breast milk.

CONCLUSIONS

A novel one-pot sol-gel synthesis approach of multi-template molecularly imprinted polymer has been reported using six sulfonamide antibiotic drugs as templates. The multi-template MIP was used as the solid phase extraction sorbent for selectively isolating six sulfonamide antibiotic drug residues from milk.

The developed MIP-SPE/HPLV-DAD method was validated according to the European Union Decision 657/2002/EC. This method is capable of performing quantitative determination and the identification of sulfonamide drugs residues in milk samples which are often found at lower concentrations than the maximum residue limit of 100 µg/kg. The new method is highly selective, green, simple in use, adequately sensitive and provides fairly reproducible results. Therefore, this method deems suitable for the intended purpose and can be adopted in routine regulatory monitoring and quality assurance for milk and allied products.

REFERENCES FOR EXAMPLE 15

[1] Tasho R. P., Cho J. Y., Veterinary antibiotics in animal waste, its distribution in soil and uptake by plants: A review, Scien. of the Tot. Envir., 563-564, (2016), pp. 366-376. Doi: http://dx.doi.org/10.1016/j.scitotenv.2016.04.140

[2] Granja R. H. M. M., Andreia C., Alessandro G. S., Wansche C. B. A., Validation of a liquid chromatography with ultraviolet detection methodology for the determination of sulfonamides in bovine milk according to 2002/657/EC, Food Control, 28, (2012), pp. 304-308. Doi: 10.1016/j.foodcont.2012.05.018

[3] Samanidou V., Nisyriou S., Multi-residue methods for confirmatory determination of antibiotics in milk, J. Sep. Sci., 31, (2008), pp. 2068-2090. Doi: 10.1002/jssc.200700647

[4] Tolika, E. P., Samanidou, V. F., & Papadoyannis, I. N., Development and validation of an HPLC method for the determination of ten sulfonamide residues in milk according to 2002/657/EC. J. of Sep. Scien., 34, (2011), pp. 1627-1635. Doi: 10.1002/jssc.201100171

[5] Stephen H. Zinner, Kenneth H. Mayer, Sulfonamides and Trimethoprim Doi: 10.1016/B978-1-4557-4801-3.00033-3

[6] European Commission Regulation (EU) No 37/2010, Off. J. Eur. Union. (2010) L 15/1-72.

[7] European Commission Decision 2002/657/EC, Off. J. Eur. Commun. 221 (2002) 8-36.

[8] Dmitrienko S. G., Kochuk E. V., Tolmacheva V. V., Apyari V. V., Zolotov Y. A., Determination of the total content of some sulfonamides in milk using solid-phase extraction coupled with off-line derivatization and spectrophotometric detection. Food Chemistry, 188, (2015), pp. 51-56. Doi: http://dx.doi.org/10.1016/j.foodchem.2015.04.123

[9] Hou X. L., Zhu G. C. L., Yang T., Zhao J., Wang L., Wu Y. L., Development and validation of an ultra high performance liquidchromatography tandem mass spectrometry method forsimultaneous determination of sulfonamides, quinolones andbenzimidazoles in bovine milk. J. of Chrom. B, 962 (2014), pp. 20-29. Doi: http://dx.doi.org/10.1016/j.jchromb.2014.05.005

[10] Yu C., Hu B., C18-coated stir bar sorptive extraction combined with high performance liquid chromatography-electrospray tandem mass spectrometry for the analysis of sulfonamides in milk and milk powder. Talanta, 90, (2012), pp. 77-84. Doi: 10.1016/j.talanta.2011.12.078

[11] Huang X., Qiu N., Yuan D., Simple and sensitive monitoring of sulfonamide veterinary residues in milk by stir bar sorptive extraction based on monolithic material and high performance liquid chromatography analysis. J. of Chrom. A, 1216, (2009), pp. 8240-8245. Doi: 10.1016/j.chroma.2009.05.031

[12] Xu Z., Song C., Hu Y., Li G., Molecularly imprinted stir bar sorptive extraction coupled with high performance liquid chromatography for trace analysis of sulfa drugs in complex samples. Talanta, 85, (2011), pp. 97-103. Doi: 10.1016/j.talanta.2011.03 0.041

[13] Gao Q., Luo D., Ding J., Feng Y. Q., Rapid magnetic solid-phase extraction based on magnetite/silica/poly (methacrylic acid-co-ethylene glycol dimethacrylate) composite microspheres for the determination of sulfonamide in milk samples. J. of Chrom. A, 1217, (2010), pp. 5602-5609. Doi: 10.1016/j.chroma.2010.06.067

[14] Li Y., Xu W., Li Z., Zhong S., Wang W., Wang A., Chen J., Fabrication of CoFe2O4-grapheme nanocomposite and its application in the magnetic solid phase extraction of sulfonamides from milk samples. Talanta, 144, (2015), pp. 1279-1286. Doi: http://dx.doi.org/10.1016/j.talanta.2015.08.006

[15] Qin Y., Jatamunua F., Zhang J., Han Y., Zon N., Shan J., Jiang Y., Pac C., Analysis of Sulfonamides, Tilmicosin and Avermectins Residues in Typical Animal Matrices with multi-Plug Filtration Cleanup by Liquid Chromatography-Tandem Mass Spectrometry Detection. J. of Chrom. B, 1053, (2017), pp. 27-33. Doi: http://doi.org/10.1016/j.jchromb.2017.04.006

[16] Samanidou V., Kabir A., Furton G. K., Karageorgou E., Manousi N., Fabric phase sorptive extraction for the fast isolation of sulfonamides residues from raw milk followed by high performance liquid chromatography with ultraviolet detection. Food Chemistry, 196, (2016), pp. 428-436. Doi: http://dx.doi.org/10.1016/j.foodchem.2015.09.060.

[17] Fumes B. H., Silva M. R., Andrade F. N., Nazario C. E. D., Lanças F. M., Recent advances and future trends in new materials for sample preparation. Trends in Analytical Chemistry, 71, (2015), pp. 9-25. Doi: http://dx.doi.org/10.1016/j.trac.2015.04.011

[18] Luliński P., Molecularly imprinted polymers based drug delivery devices: a way to application in modem pharmacotherapy. A review. Materials Science and Engineering C, 76, (2017), pp. 1344-1353. Doi: http://dx.doi.org/10.1016/j.msec.2017.02.138

All patents, patent applications, provisional applications, and publications referred to or cited herein are incorporated by reference in their entirety, including all figures and tables, to the extent they are not inconsistent with the explicit teachings of this specification.

The description herein of any aspect or embodiment of the invention using terms such as "comprising," "having," "including" or "containing" with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of synthesizing a molecularly imprinted polymer (MIP) matrix, comprising:
    mixing a template analyte with more than one sol-gel precursor to form a template-precursor complex, the sol-gel precursors comprising silane groups;
    hydrolyzing the sol-gel precursors of the template-precursor complex and a cross-linking agent with a hydrolytic agent in the presence of a reaction catalyst;
    combining the hydrolyzed cross-linking agent with the template-precursor complex having hydrolyzed sol-gel precursors;
    adding a basic solution to the combination of the hydrolyzed cross-linking agent and the template-precursor complex to form a sol-gel polymer network surrounding the template analyte; and
    extracting the template analyte using a solvent, leaving behind molecular cavities in the sol-gel polymer network that are complementary in size, shape, and functionality to the template analyte.

2. The method according to claim 1, the template analyte being selected from drugs, cells, proteins, amino acids, toxins, and viruses.

3. The method according to claim 1, the template analyte being an antibiotic drug selected from chloramphenicol, thiamphnicol, florfenicol, ceftiofur, cefaclor, oxytetracycline, tetracycline, sulfamethazine, sulfanilamide, sulfacetamide, sulfadiazine, sulfathiazole, sulfamerazine, sulfamethizole, sulfadimethoxine, amoxicillin, ampicillin, ciprofloxacin, enrofloxacin, and analogous compounds thereof.

4. The method according to claim 1, the sol-gel precursors being 3-aminopropyltriethoxysilane and triethoxyphenylsilane.

5. The method according to claim 1, the cross-linking agent being tetramethyl orthosilicate.

6. The method according to claim 1, the reaction catalyst being an acid.

7. The method according to claim 6, the reaction catalyst being hydrochloric acid.

8. The method according to claim 1, the hydrolytic agent being water.

9. The method according to claim 1, the solvent being selected from methanol, ethanol, isopropanol, formic acid, acetonitrile, acetone, and mixtures thereof.

10. A sol-gel MIP sorbent material prepared using the method according to claim 1.

11. The material according to claim 10, said material being capable of detecting the template analyte in a sample but is indifferent to other species present in the same sample.

12. A method of detecting a template analyte in a fluid sample, comprising:
    providing a sol-gel polymer sorbent material imprinted molecularly with the template analyte, the sorbent material being prepared according to claim 1, dried, and packaged in an apparatus capable of performing solid-phase extraction;
    passing the fluid sample through the sorbent material; and
    quantifying the concentration of the template analyte in the eluent of the sorbent material.

13. The method according to claim 12, the apparatus capable of performing solid-phase extraction being selected from a syringe and a solid-phase extraction cartridge.

14. The method according to claim 12, the sample being selected from physiological fluids, forensic specimens, environmental pollutants, food samples, beverage samples, pharmaceutical samples, chemical samples, drug residues and metabolites thereof, and poison residues and metabolites thereof.

15. The method according to claim 12, the quantification of the concentration of the template analyte in the eluent being obtained using liquid chromatography.

16. A method of detecting one or more template analytes in a sample, comprising:
    providing a molecularly imprinted polymer (MIP) sorbent material, the sorbent material being prepared via a sol-gel process employing one or more sulfonamide drugs as the template analyte(s), 3-aminopropyltriethoxysilane and triethoxyphenylsilane as sol-gel precursors, tetramethyl orthosilicate as a cross-linking agent, hydrochloric acid as a reaction catalyst, water as a hydrolytic agent, and isopropanol and methanol as solvents;

packaging dried MIP sorbent material in an extraction apparatus selected from a syringe and a solid-phase extraction cartridge;

providing a fluid sample;

passing the fluid sample through the extraction apparatus; and quantifying the concentration of the template analyte(s) in the eluent of the MIP sorbent material.

17. The method according to claim 16, the eluent of the sorbent material being obtained using a solvent selected from methanol, ethanol, isopropanol, formic acid, acetonitrile, acetone, and a mixture thereof.

18. The method according to claim 16, the sample being selected from physiological fluids, forensic specimens, environmental pollutants, food samples, beverage samples, pharmaceutical samples, chemical samples, drug residues and metabolites thereof, and poison residues and metabolites thereof.

19. The method according to claim 16, the one or more sulfonamide drugs being selected from sulfanilamide, sulfacetamide, sulfadiazine, sulfathiazole, sulfamerazine, sulfamethizole, and analogous compounds thereof.

20. A method of synthesizing a molecularly imprinted polymer (MIP) matrix, comprising:

mixing a template analyte with a mixture of sol-gel precursors to form a template-precursor complex, the mixture of sol-gel precursors comprising 3-aminopropyltriethoxysilane and triethoxyphenylsilane;

hydrolyzing the sol-gel precursors of the template-precursor complex and a cross-linking agent with a hydrolytic agent in the presence of a reaction catalyst;

combining the hydrolyzed cross-linking agent with the template-precursor complex having hydrolyzed sol-gel precursors;

allowing a sol-gel polymer network to form surrounding the template analyte; and extracting the template analyte using a solvent, leaving behind molecular cavities in the sol-gel polymer network that are complementary in size, shape, and functionality to the template analyte.

* * * * *